US008205782B2

(12) United States Patent
Harari et al.

(10) Patent No.: US 8,205,782 B2
(45) Date of Patent: Jun. 26, 2012

(54) COMPRESSION ASSEMBLIES AND APPLICATORS FOR USE THEREWITH

(75) Inventors: Boaz Harari, Tel Aviv (IL); Leonid Monassevitch, Hadera (IL); Michael Arad, Tel Aviv (IL); Doron Kopelman, Caesarea (IL); Amir Perle, Haifa (IL); Boaz Shenhav, Tel Aviv (IL); Kobby Greenberg, Even Yehuda (IL)

(73) Assignee: Niti Surgical Solutions Ltd., Netanya (IL)

( * ) Notice: Subject to any disclaimer, the term of this patent is extended or adjusted under 35 U.S.C. 154(b) by 375 days.

(21) Appl. No.: 12/373,450

(22) PCT Filed: Jul. 12, 2007

(86) PCT No.: PCT/IL2007/000878
§ 371 (c)(1),
(2), (4) Date: Aug. 4, 2009

(87) PCT Pub. No.: WO2008/007377
PCT Pub. Date: Jan. 17, 2008

(65) Prior Publication Data
US 2009/0302089 A1 Dec. 10, 2009

Related U.S. Application Data

(63) Continuation-in-part of application No. 11/485,604, filed on Jul. 12, 2006, now Pat. No. 7,527,185.

(60) Provisional application No. 60/900,723, filed on Feb. 12, 2007.

(51) Int. Cl.
*A61B 17/04* (2006.01)

(52) U.S. Cl. ............... 227/180.1; 227/19; 227/181.1; 227/179.1

(58) Field of Classification Search .............. 227/19, 227/179.1, 180.1, 181.1
See application file for complete search history.

(56) References Cited

U.S. PATENT DOCUMENTS
4,055,186 A 10/1977 Leveen
(Continued)

FOREIGN PATENT DOCUMENTS
EP 0 326 757 B1 8/1989
(Continued)

OTHER PUBLICATIONS

C. Wullstein and E. Gross, "Compression anastomosis (AKA-2) in colorectal surgery: results in 442 consecutive patients", British Journal of Surgery, 2000, vol. 87, pp. 1071-1075.

*Primary Examiner* — Brian D Nash
(74) *Attorney, Agent, or Firm* — Pearne & Gordon LLP

(57) ABSTRACT

A compression assembly for use in compressing tissue comprising a first portion which includes a first compression element and a second portion which comprises a second compression element, at least one support element, and at least one spring element. Typically the spring element is formed of a shape-memory material. The at least one spring element is in compressive force contact with the second compression element and the tissue to be joined is positioned between the first and second compression elements. A plurality of needles on one of the support elements is operative to pierce the tissue and the first portion of the assembly, holding the first compression element to the second portion of the assembly. The invention is appropriate for joining severed tissue in anastomosis procedures or closing natural or surgically produced tissue perforations.

26 Claims, 48 Drawing Sheets

U.S. PATENT DOCUMENTS

| | | | |
|---|---|---|---|
| 4,304,236 A | 12/1981 | Conta et al. | |
| 4,476,863 A | 10/1984 | Kanshin et al. | |
| 4,505,272 A | 3/1985 | Utyamyshev et al. | |
| 4,567,891 A | 2/1986 | Kanshin et al. | |
| 4,752,024 A | 6/1988 | Green et al. | |
| 4,893,622 A | 1/1990 | Green et al. | |
| 4,903,697 A * | 2/1990 | Resnick et al. | 227/178.1 |
| 4,917,114 A * | 4/1990 | Green et al. | 227/179.1 |
| 4,957,499 A | 9/1990 | Lipatov et al. | |
| 5,171,252 A | 12/1992 | Friedland | |
| 5,197,648 A | 3/1993 | Gingold | |
| 5,205,459 A | 4/1993 | Brinkerhoff et al. | |
| 5,250,058 A * | 10/1993 | Miller et al. | 606/154 |
| 5,271,543 A | 12/1993 | Grant et al. | |
| 5,282,810 A | 2/1994 | Allen et al. | |
| 5,285,945 A | 2/1994 | Brinkerhoff et al. | |
| 5,312,024 A | 5/1994 | Grant et al. | |
| 5,336,233 A * | 8/1994 | Chen | 606/153 |
| 5,344,059 A | 9/1994 | Green et al. | |
| 5,346,501 A | 9/1994 | Regula et al. | |
| 5,411,508 A | 5/1995 | Bessler et al. | |
| 5,639,008 A | 6/1997 | Gallagher et al. | |
| 5,669,918 A | 9/1997 | Balazs et al. | |
| 5,758,814 A | 6/1998 | Gallagher et al. | |
| 5,951,576 A | 9/1999 | Wakabayashi | |
| 6,117,148 A | 9/2000 | Ravo et al. | |
| 6,171,321 B1 | 1/2001 | Gifford, III et al. | |
| 6,193,129 B1 | 2/2001 | Bittner et al. | |
| 6,402,765 B1 | 6/2002 | Monassevitch et al. | |
| 6,497,710 B2 * | 12/2002 | Yencho et al. | 606/153 |
| 6,503,259 B2 | 1/2003 | Huxel et al. | |
| 6,736,825 B2 * | 5/2004 | Blatter et al. | 606/153 |
| 6,884,250 B2 | 4/2005 | Monassevitch et al. | |
| 6,896,684 B2 | 5/2005 | Monassevitch et al. | |
| 6,899,718 B2 | 5/2005 | Gifford, III et al. | |
| 7,094,247 B2 | 8/2006 | Monassevitch et al. | |
| 2001/0001825 A1 | 5/2001 | Snow et al. | |
| 2002/0058955 A1 | 5/2002 | Blatter et al. | |
| 2002/0087175 A1 | 7/2002 | Gifford, III et al. | |
| 2002/0151914 A1 | 10/2002 | Gifford, III et al. | |
| 2004/0015178 A1 * | 1/2004 | Monassevitch et al. | 606/153 |
| 2004/0015179 A1 * | 1/2004 | Monassevitch et al. | 606/153 |
| 2005/0059997 A1 | 3/2005 | Bauman et al. | |
| 2005/0070934 A1 | 3/2005 | Tanaka et al. | |
| 2005/0184121 A1 | 8/2005 | Heinrich | |
| 2005/0283191 A1 | 12/2005 | Fontayne et al. | |
| 2006/0253141 A1 | 11/2006 | Ortiz et al. | |

FOREIGN PATENT DOCUMENTS

| | | |
|---|---|---|
| SU | 1186199 A | 10/1985 |
| WO | 81/00046 A1 | 1/1981 |

* cited by examiner

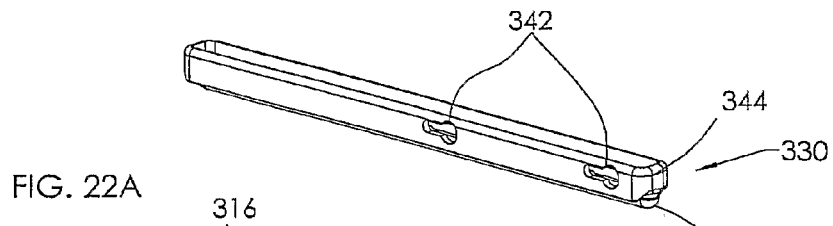
FIG. 22A
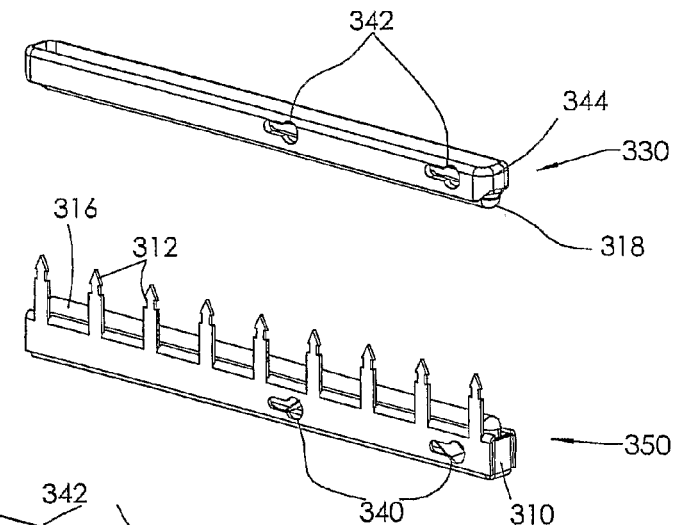
FIG. 22B
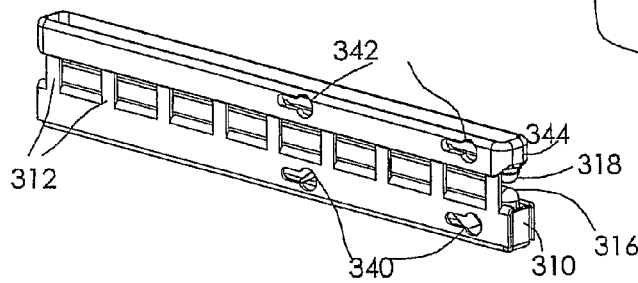
FIG. 22C
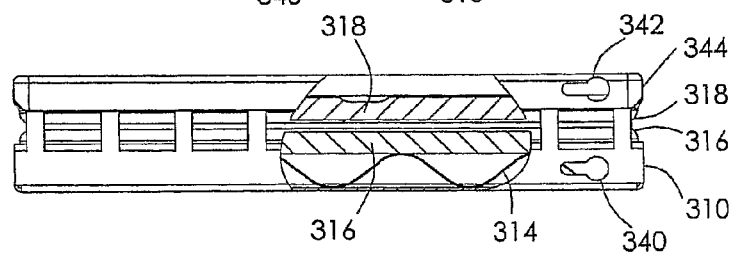
FIG. 22D
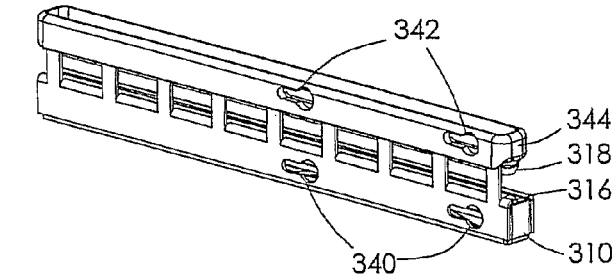
FIG. 22E
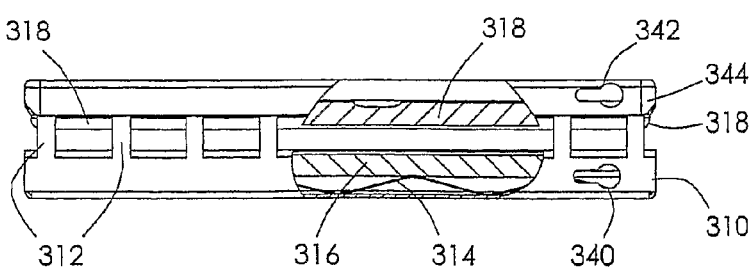

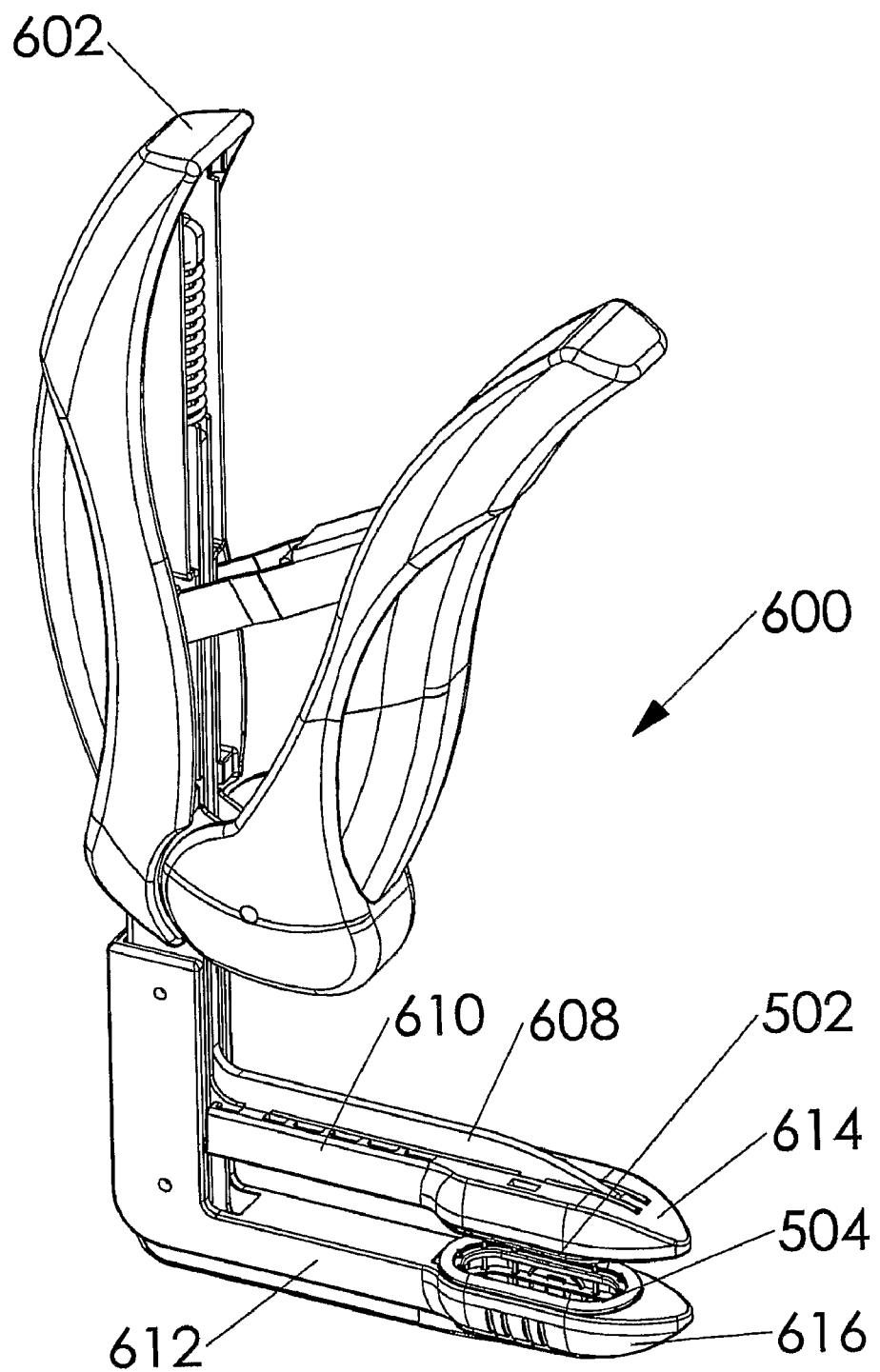
Fig·26A

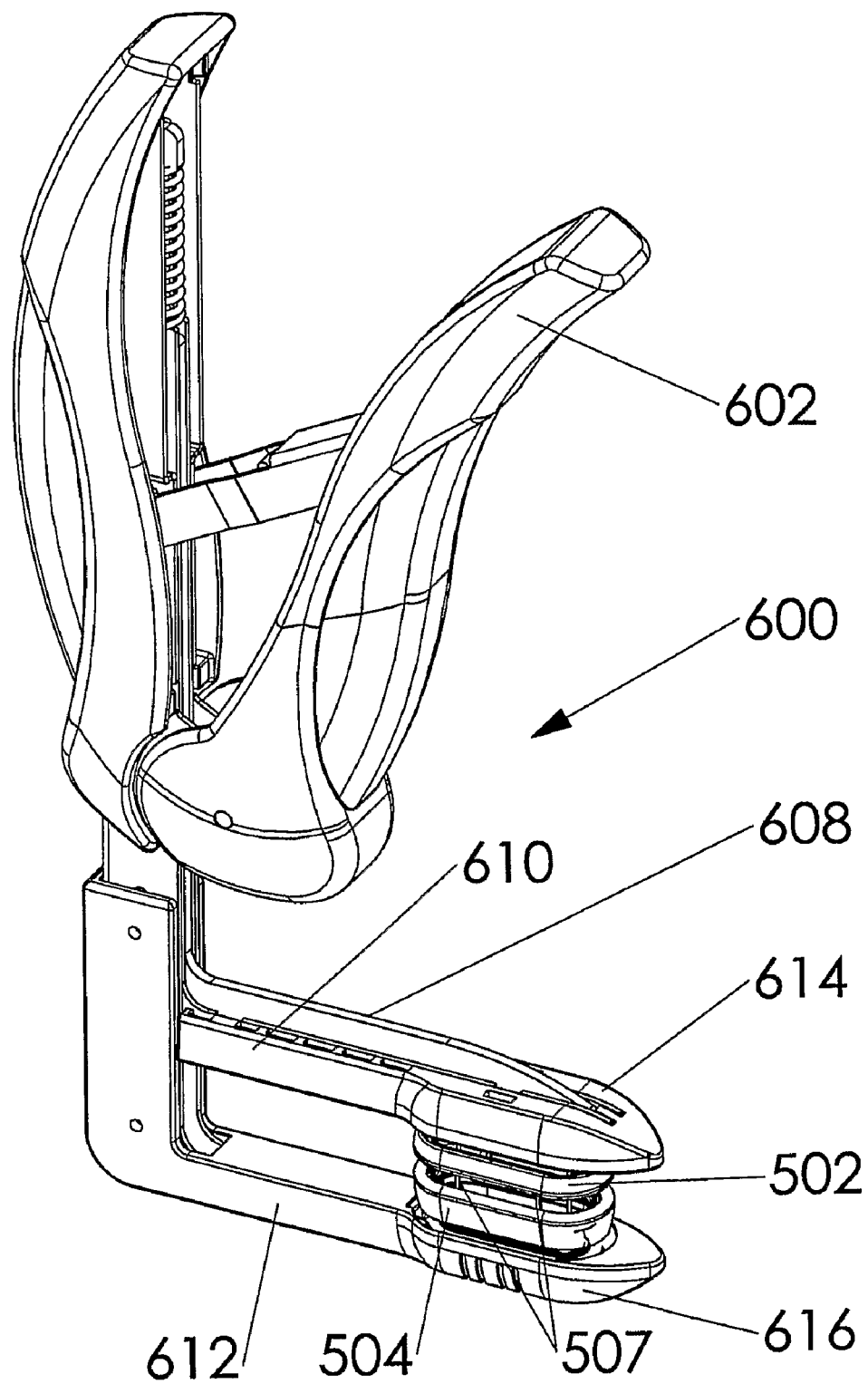
Fig·31A

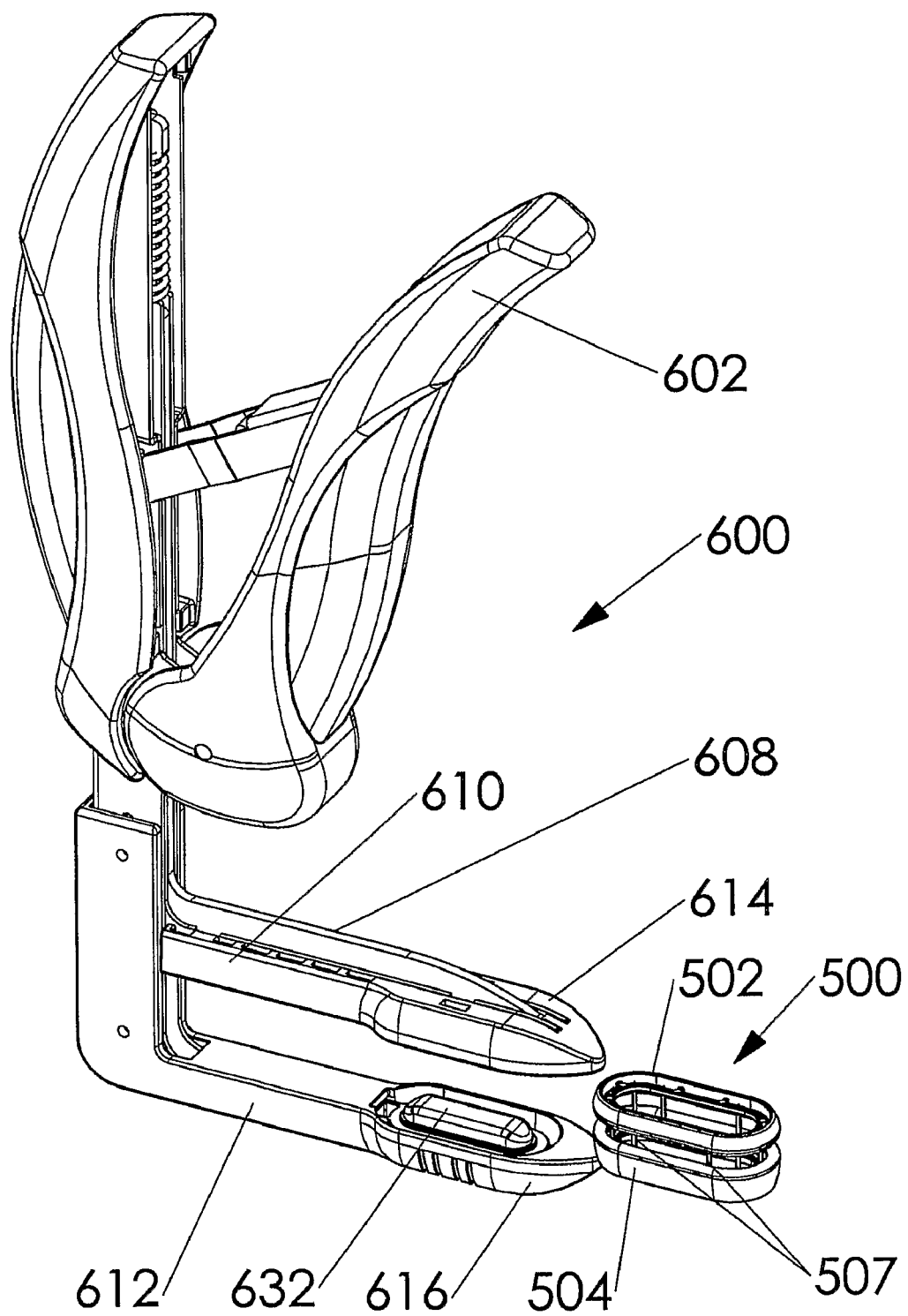
Fig·32A

COMPRESSION ASSEMBLIES AND APPLICATORS FOR USE THEREWITH

CROSS REFERENCE TO RELATED APPLICATIONS

This application is a continuation-in-part of U.S. patent application Ser. No. 11/485,604, filed Jul. 12, 2006, now U.S. Pat. No. 7,527,185, issued May 5, 2009, and U.S. Provisional Appl. No. 60/900,723, filed on Feb. 12, 2007.

FIELD OF THE INVENTION

The present invention relates to compression assemblies and applicators for use in anastomosis surgical procedures and other procedures requiring tissue compression.

DEFINITION

Except where indicated otherwise, the terms below will be used with the following meanings throughout the specification and claims:

Anastomosis: a surgical restoration of the continuity of a hollow organ which has been separated.

Proximal: situated close to the user.

Distal: situated distant or away from the user (relative to proximal).

BACKGROUND OF THE INVENTION

Excision of a segment of diseased colon or intestine and subsequent anastomosis of the cut portions is known in the art. Such excision and anastomosis can be carried out by entering the abdominal cavity using either open surgery or a laparoscopic procedure. Both end-to-end and side-to-side anastomosis procedures are known.

The integrity of the anastomosis must be sound so that there is no risk of the anastomosis rupturing or leaking into the abdominal cavity. As is well known, opening the bowel lumen and exposing the clean abdominal cavity to contamination increases the risk of postoperative infection.

In order to avoid opening the bowel lumen and exposing the clean abdominal cavity to endoluminal contents, intussusception of the colon or intestine may be employed. Intussusception enables an excision to be created within an apparatus thereby preventing contamination of the body cavity. Intussusception, anastomosis and resection of the intussuscepted segment are known in the art.

Many of the prior art methods for anastomosis utilize stapling of the portions of bowel or intestine to be joined. It would be advantageous to utilize a procedure and apparatus that did not rely on applying a plurality of staples or other connecting devices, which, of necessity, remain in the bowel and which, despite the utmost care by the surgeon, may produce a join that may leak or rupture.

Surgical fastening clips are known in the art. The clips apply a clamping force to a site, such as a blood vessel, thereby reducing its cross-sectional area. Surgical fastening clips known in the art are sometimes formed of a shape-memory alloy which deform to a closed configuration when heated. The clamping force applied by the clip increases as it is heated.

The surgical clip and the anastomosis clip applicator device, recited in U.S. Pat. Nos. 6,402,765 and 6,896,684 respectively, both to Monassevitch et al., relate to a shape-memory alloy clip insertable through apertures formed in the side-walls of a pair of adjacent hollow organ portions utilizing an anastomosis clip applicator device. Access to the hollow organ is generally extra-tubular, that is, achieved by means of open surgery or a laparoscopic procedure during which access to the organ parts results in the risk of exposure of the abdominal cavity to contamination from the excised or severed organ. Furthermore, the nature of the anastomosis often provides a join of the organ portions through adjacent side-walls. Generally, a join formed of the in-line excised ends is preferred. This arrangement avoids the possibility of resistance to or reduction in the flow through the anastomosed adjacent organ portions.

U.S. Pat. Nos. 6,884,250 and 7,094,247, both to Monassevitch et al., describe endoluminal intussusception and anastomosis devices which apply surgical clips to an intussuscepted and anastomosed region of a lumen with the clip being delivered endoluminally. The apparatuses described in these documents have, in practice, a limiting minimum external diameter which substantially restricts their application.

There still exists a need for a surgical compression apparatus which allows for endoluminal insertion into organ lumens, including transanal insertion, as well as insertion into small lumens, such as that of the esophagus. Such endoluminal insertion would obviate the need for additional surgical procedures, such as enterotomies, which are often accompanied by manual sutures. This would greatly assist in forming a smooth robust seal of the wound junction during the healing period, as well as preserve its elasticity during the post-operative period.

Additionally, various methods are known in the art for joining tissue portions at the site of organ resections, particularly gastrointestinal (GI) tract resections, or at the site of other types of tissue perforations or tissue openings. These methods include threads for manual suturing, staplers for mechanical suturing, tissue adhesives and compression rings, loops and clips.

Junctions using compression devices, such as rings, loops, and clips, ensure the best seal and post-operative functioning of the organs. However, typically, the force provided by the devices is dependent on the thickness of the tissue of the organ to undergo anastomosis. Accordingly, the resulting join which is formed is still weak or incomplete.

Furthermore, the compressive force exerted by clips generally is not equal at both ends of the clip because of the clips' typically asymmetric construction. Similarly, compression does not act along a line between the two compressing portions holding the tissue to be compressed. This can lead to the clip disengaging from the closure site before closure is complete and scar tissue matures. Also, typically, clips do not necessarily have a securing mechanism against slipping off the tissue being compressed.

SUMMARY OF THE INVENTION

It is an object of the present invention to provide compression assemblies for use in compressing and closing wounds.

It is an object of the present invention to provide compression assemblies for use in surgical anastomosis procedures including end-to-end, side-to-side or end-to-side anastomosis procedures.

It is yet another object of the present invention to provide a compression assembly wherein compression is provided by an element of the assembly formed of a shape-memory material. Other materials which do not adhere to Hooke's law may also be used. Materials contemplated in the present invention allow for a relatively slow rate of change of the force applied to the compressed tissue over at least the greater portion of the extension range used during the compression procedure.

It is a further object of the present invention to provide applicators and systems for applying the compression assemblies constructed as taught herein.

Another object of the present invention is to provide a method for applying the compression assemblies constructed as taught herein.

It is another object of the present invention to provide compression assemblies and associated applicators that can have reduced dimensions, thereby extending the range of application of the assemblies and applicators. Use of the assemblies taught herein increases the quality of the join formed during luminal anastomosis procedures or other surgical procedures use to join resected or otherwise perforated tissue. The join formed provides a substantially liquid-tight seal which promotes hemostasis while reducing opportunities for sepsis.

There is therefore provided in one aspect of the present invention a compression assembly. The assembly comprises a first and second portion. The first portion includes a first compression element. The second portion comprises a second compression element positioned substantially parallel to and spaced apart from the first compression element. The first and second compression elements are adapted to be brought together in the presence of a closure force applied between them. The assembly also includes one or more support elements, where one of the one or more support elements is a needle bearing support element. The needle bearing support element is positioned on a side of the second compression element distal from the first compression element and has a plurality of needles extending generally transversely toward the first compression element. The second portion of the assembly also includes one or more spring elements formed at least partially of a material which, when providing a restorative force, behaves in a manner other than that predicted by Hooke's Law over at least a portion of its expected extension range. The spring element is positioned on one of the one or more support elements and it is in compressive force transmissive contact with the second compression element. When the compression assembly is positioned so as to hold between the first and second compression elements tissue portions to be compressed, the needle bearing support is operative in response to the closure force to drive the plurality of needles through the tissue portions to be compressed and to anchor the plurality of needles in the first portion. When the first and second compression elements are brought together in the presence of the closure force holding the tissue portions, the restorative force provided by the at least one spring element is operative on the second compression element to compress the tissue portions.

In one embodiment of the compression assembly, the spring element has a force-extension graph composed of a first region, a second region and an intermediate region lying between the first and second regions. In the intermediate region, the Young's modulus of the material is substantially less than the Young's modulus of one or more of the two adjacent regions.

In another embodiment of the compression assembly, the material from which the spring element is at least partially formed has a recoverable strain of at least about 4%. In some instances of this embodiment, the material from which the spring element is at least partially formed has a recoverable strain of at least about 6%.

In yet another embodiment of the compression assembly, the material from which the spring element is at least partially formed is a shape memory material.

In still another embodiment of the compression assembly, the one or more spring elements are positioned on the needle bearing support element so as to be in compressive force transmissive contact with the second compression element.

In a further embodiment of the compression assembly, the first and second compression elements and the one or more support elements are all formed having the same shape, the shape being selected from the group of shapes consisting of: circular, elliptical, oval and linear.

In an embodiment of the compression assembly, the first portion further comprises an upper element support made from a rigid polymeric material with the first compression element affixed to the upper element support. The plurality of needles is operable to penetrate and pass through the tissue and the upper element support in response to a predetermined force applied to the needle bearing support element. In some embodiments, the upper element support includes a plurality of holes in apposition to and in registration with the plurality of needles allowing entry of the needles and passage through the tissue and the upper element support in response to a predetermined force applied to the needle bearing support element.

In another embodiment of the compression assembly, the one or more spring elements are brought to their compressed configuration, and the alloy from which they are formed to its martensitic state, by applying a compressive stress to the one or more spring elements.

In a further embodiment of the compression assembly, the one or more spring elements are brought to their compressed configuration, and the alloy from which they are formed to its martensitic state, by cooling and then applying a compressive stress to the one or more spring elements.

In still another embodiment of the compression assembly, the one or more support elements are two or more support elements, where one of the two or more support elements is the needle bearing support element and another of the two or more support elements is a compression flange positioned inside the second compression element. In some instances of this embodiment, the compression flange is positioned between the needle bearing support element and the second compression element, and the one or more spring elements are positioned on the compression flange so as to be in compressive force transmissive contact with the second compression element.

The embodiments of the compression assembly of the present invention may be constructed for use in side-to-side anastomosis surgical procedures. Alternatively, they may be constructed for use in end-to-end anastomosis surgical procedures. Alternatively, they may be constructed for use in end-to-side anastomosis surgical procedures. Alternatively, they may be constructed for use in compression closure of naturally or surgically produced tissue openings.

In yet another aspect of the present invention there is provided a compression system for compressing tissue. The system includes a compression assembly as in any of the embodiments described above and an applicator. The applicator is intended for applying the assembly to the tissue to be compressed. The applicator has a proximal and a distal end and comprises attachment means including a first connecting member for attachment to the first portion of the compression assembly and a second connecting member for attachment to the second portion of the compression assembly. The connecting members are operable to move the attached first portion toward the second portion of the assembly and vice versa. The applicator also comprises one or more deployment means positioned on the distal end of the applicator. The deployment means is operable to deploy the second portion of the compression assembly positioned thereon so that the plurality of needles may be brought to a position where they pierce the first portion and the tissue portions to be compressed mechanically connecting the first and second portions of the assembly. The applicator also comprises one or more activators operationally connected to the one or more deployment means and the attachment means for activating the attachment means and the deployment means.

In an embodiment of the compression system, the one or more spring elements are positioned on the needle bearing support element so as to be in compressive force transmissive contact with the second compression element.

In another embodiment of the compression system, the first and second compression elements and the one or more support elements are all formed having the same shape. The shape may be selected from the group of shapes consisting of: circular, elliptical, oval and linear.

In a further embodiment of the compression system, the first portion further comprises an upper element support made from a rigid polymeric material with the first compression element affixed to the upper element support. In some instances of this embodiment, the needles are operable to penetrate and pass through the tissue and the upper element support in response to a predetermined force applied to the needle bearing support element.

In yet another embodiment of the compression system, the one or more support elements are two or more support elements, where one of the two or more support elements is the needle bearing support element and another of the two or more support elements is a compression flange positioned inside the second compression element. In some instances of this embodiment, the compression flange is positioned between the needle bearing support element and the second compression element, and the one or more spring elements are positioned on the compression flange so as to be in compressive force transmissive contact with the second compression element.

In yet another embodiment of the compression system, the deployment means further comprises a load means so that when the one or more spring elements are deployed, the load means exerts a load on the one or more spring elements, thereby bringing them to their compressed configuration and the alloy from which they are formed to its martensitic state. In some instances of this embodiment, the one or more spring elements are cooled before the load means exerts a load on, and compresses, the one or more spring elements.

In still another embodiment of the compression system, the applicator further comprises a blade element positioned in a spaced relationship to the deployment means. The blade element is operable to cut through the first portion of the compression assembly. In some instances of this embodiment, the blade element is further operable to cut through the tissue portions held between the first and the second portions of the compression assembly.

In some instances of this embodiment of the compression system, the one or more support elements are two or more support elements, where one of the two or more support elements is the needle bearing support element and another of the two or more support elements is a compression flange positioned inside the second compression element. In some instances, the compression flange is positioned between the needle bearing support element and the second compression element, and the one or more spring elements are positioned on the compression flange so as to be in compressive force transmissive contact with the second compression element.

In other instances of this embodiment of the compression system, the first portion of the compression assembly is made from a rigid polymeric material, and has an outer part integrally formed with an inner core. In some instances, the blade element cuts through the first portion of the compression assembly, the first portion's outer part thereby being severed from the inner core and detached from the attachment means. The outer part remains mechanically connected to the second portion by the plurality of needles so that the outer part is in registration with, and serves as an anvil for, the second compression element when the one or more spring elements press on the second compression element compressing the tissue held therebetween.

In yet other instances of this embodiment of the compression system, the deployment means further comprises a load means so that when the one or more spring elements are deployed, the load means exerts a load on the one or more spring elements thereby bringing them to their compressed configuration and the alloy from which they are formed to its martensitic state. In some instances of this embodiment, the one or more spring elements are cooled before the load means exerts a load on, and compresses, the one or more spring elements. In yet another aspect of the present invention there is provided a method for compressing tissue. The method comprises the steps of:

positioning the tissue to be compressed between first and second portions of a compression assembly operable for compressing tissue;

moving the first portion of the assembly into close proximity to the second portion so as to hold the tissue therebetween; and compressing the held tissue between the first and second portions of the compression assembly with a force produced by one or more spring elements formed at least partially of a material which when the one or more spring elements provide a restorative force, they behave in a manner other than that predicted by Hooke's Law over at least a portion of their expected extension range.

In one embodiment of the method, the one or more spring elements have a force-extension graph composed of a first region, a second region and an intermediate region lying between the first and second regions. In the intermediate region, the Young's modulus of the material from which the spring elements are formed is substantially less than the Young's modulus of one or more of the two adjacent regions.

In another embodiment of the method of the present invention, the material from which the spring element is at least partially formed has a recoverable strain of at least about 4%. In some instances of this embodiment, the material from which the one or more spring elements are at least partially formed has a recoverable strain of at least about 6%.

In yet another embodiment of the method, the material from which the one or more spring elements are at least partially formed is a shape memory material. In some instances of this embodiment of the method, the method further includes the step of cooling the one or more spring elements so that the material from which they are formed is brought to its martensite state. In some instances of this embodiment, the method further includes the step of deploying the one or more shape-memory alloy spring elements when they are in their compressed configuration, and the alloy from which formed is in its martensitic state. In other instances of this embodiment, the martensitic state of the alloy of the deployed one or more spring elements is a martensitic state selected from a group of states consisting of the stress-retained martensitic state and the stress-induced martensitic state. In yet another instance of this embodiment, the method further includes the step of deploying the one or more spring elements in their non-compressed configuration, and the alloy from which the one or more spring elements are at least partly formed is in its austenite state.

In another embodiment of the method, the method further includes the step of cutting the compressed tissue and cutting through the first portion of the compression assembly prior to the step of compressing.

BRIEF DESCRIPTION OF THE DRAWINGS

The present invention will be more fully understood and its features and advantages will become apparent to those skilled in the art by reference to the ensuing description, taken in conjunction with the accompanying drawings, in which:

FIGS. 22A-22E show various views of the compression assembly of FIG. 21 including a view of separated upper and lower elements of the assembly (FIG. 22A); two views, including a partial cut-away view, of the assembly as it holds tissue (not shown) between its upper and lower elements (FIGS. 22B-22C); and two views, including a partial cut away view, of the assembly as it is moved together and closed around tissue (not shown) held between its upper and lower elements (FIGS. 22D-22E);

FIGS. 26A, 26B and 26C show isometric, side, and partially cut-away views, respectively, of the elliptical compression assembly shown in FIGS. 25A-25D positioned on an applicator constructed according to the present invention, the applicator in its open position;

FIGS. 31A and 31B show isometric and side views of the elliptical compression assembly being released from the jaws of the applicator after the cutting step has been effected; and FIGS. 32A and 32B show isometric and side views of the elliptical compression assembly being ejected from the applicator with tissue (not shown) positioned between the mechanically connected upper and lower portions of the assembly.

Similar elements in the Figures are numbered with similar numerals.

DETAILED DESCRIPTION OF THE INVENTION

Figure 1:
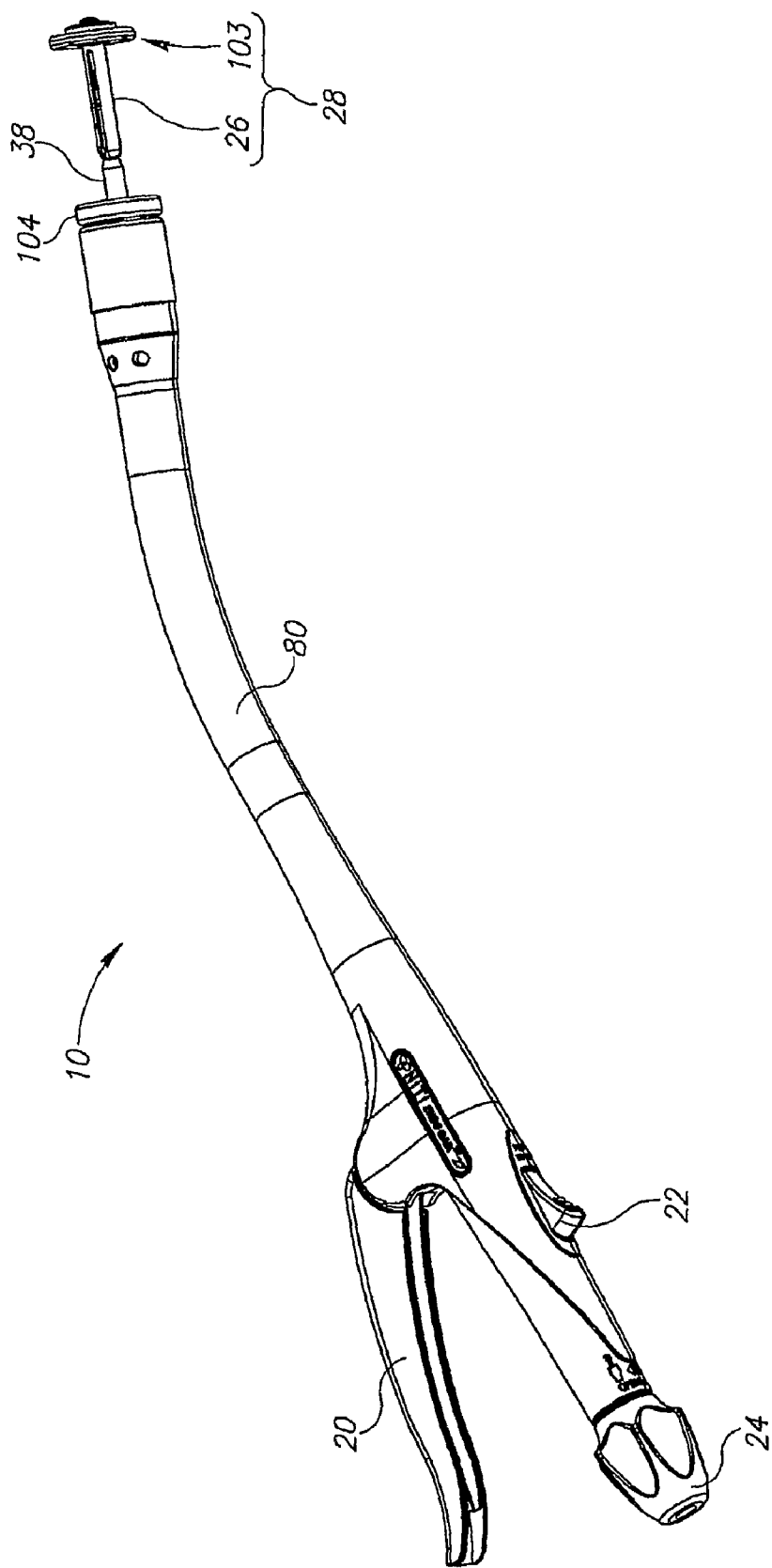
FIG. 1 illustrates a side view of a compression anastomosis ring (CAR) applicator usable with a CAR assembly constructed according to the present invention.

The present invention provides compression assemblies for anastomosis or other surgical tissue closure procedures. Systems, including applicators for applying the assemblies, are also described.

The compression assemblies include a first portion and a second portion where, in operation, an element of the latter is compressed against an element of the former. The first and second portions are initially not in mechanical connection with each other. They are brought into mechanical connection with each other when needle-like structures positioned on an element of the second portion are pushed through an element of the first portion. A finite gap between the two portions is formed when they are joined.

Compression is effected by spring elements acting on a compression element of the second portion displacing it toward a compression element of the first portion. During the compression process, tissue to be closed or joined, is positioned between the two compression elements.

The spring elements are formed from materials which do not behave according to Hooke's law. Their behavior is such that an extended region of the force versus distance graph has a slope substantially less than at least one of the regions adjacent to the extended region. This type of force versus stress curve permits optimizing the compression, and hence healing, process. Force is maximum at the beginning of the compression/healing process when hemostasis is required; force is relatively slowly decreasing in the healing process's extended intermediate region to allow for better joining of the tissue being compressed; and a small decreasing force is present towards the end of the healing process thereby minimizing tearing of the thin tissue being compressed by the needle-like structures and reducing the risk of early detachment of the assemblies. Without limiting the types of materials contemplated by the present invention, a typical such material is a shape-memory alloy such as a Ni—Ti alloy.

The spring element is positioned on an element of the second portion. The spring element is in mechanical communication with a compression element of the second portion. The compression assemblies detach from the site of compression when anastomosis or other tissue closure procedure is complete. The assembly is naturally expelled through the anus when the tissue undergoing anastomosis is bowel tissue.

The applicator delivering the assembly in anastomosis applications is often constructed so as to cut the central part of the ends of the resected bowel. Anastomosis is thereby effected cleanly ensuring patency and continuity of the joined bowel after healing. Assemblies and applicators of the present invention may be used to achieve anastomosis, either end-to-end, side-to-side or end-to side anastomosis, following either conventional or laparoscopic excision of a diseased intestinal portion.

The anastomosis systems of the present invention are described herein as being used to join bowel tissue from which an excised portion has been removed. It should be evident that the device of the present invention may, with little or no modification, be used with tissue of other organs as well. Such other organs include, but are not limited to, the esophagus and stomach.

It should be noted that the present invention provides linear assemblies, as well as assemblies of many other shapes. In addition to their use in anastomosis surgical procedures, these assemblies can be used to compress and effect closure of excisions, resections and other naturally occurring and surgically produced perforations.

Similarly, it should be readily apparent to one skilled in the art that the devices, assemblies and methods of the present invention can be used to effect anastomosis or general compression on tissue of animals as well as humans, particularly, but without being limiting, other mammalian species.

Reference is now made to FIG. 1 in which is shown an overview of a typical CAR applicator 10 suitable for applying a CAR assembly 100 (best seen in FIG. 7 below) constructed according to the present invention for use in anastomosis surgical procedures. It should be noted that the CAR assembly and the CAR applicator described herein are but one type of assembly and applicator described elsewhere in the text as compression assemblies and compression assembly applicators.

Applicator 10 consists of an elongated housing 80 at the proximal end of which is situated a control knob 24, a lever 20, and a cut trigger 22. At the distal end of CAR applicator 10 is situated an anvil assembly 28 which includes an anvil disk 103 of CAR assembly 100 and an anvil rod 26. Anvil assembly 28 connects to applicator 10 by a trocar 38. A bottom ring 104 of CAR assembly 100 is affixed directly to the distal end of CAR applicator 10.

Figure 2:
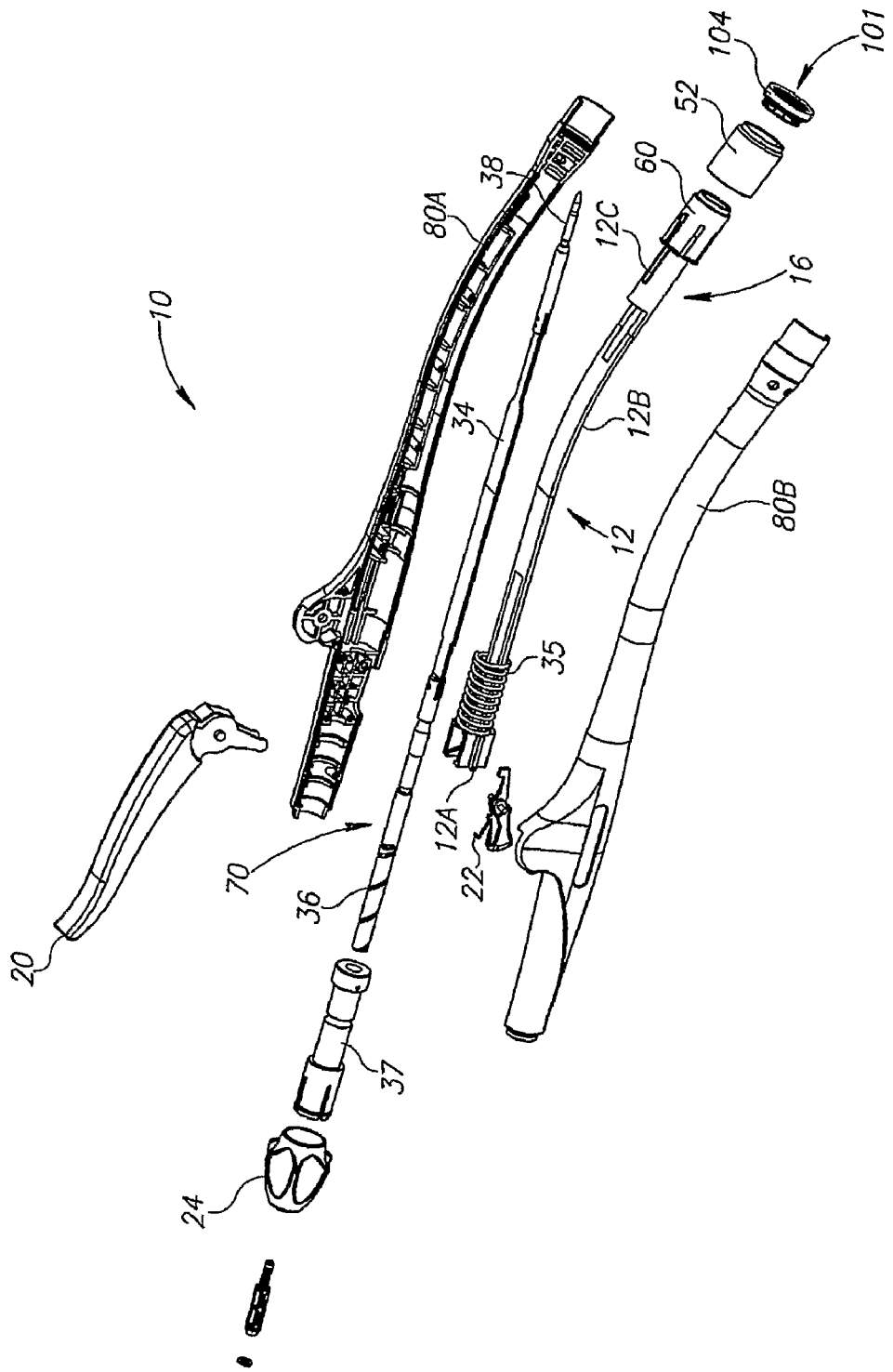
FIG. 2 shows an exploded view of the CAR applicator shown in FIG. 1.

An exploded view of applicator 10 is shown in FIG. 2 to which reference is now made. The exploded view shows a view of housing 80, its halves denoted as 80A and 80B. Additionally, central member 70 is shown, the member having control knob 24 positioned at its proximal end and trocar 38 at its distal end. Joined to trocar 38 is trocar connecting link 34 which in turn is in mechanical communication with helix 36 which itself is in mechanical communication with knob shaft 37. Shaft 37 is controlled by control knob 24 which allows for the advance or retraction of trocar 38.

Central member 70 is inserted into blade pusher assembly 16, the latter includes blade pusher 12. Blade pusher 12 has a proximal end 12A connected to its distal end 12C by linking section 12B. The proximal end 12A of blade pusher 12 is in mechanical communication with main spring 35. At the distal end 12C of blade pusher 12 are other elements of blade pusher assembly 16. At distal end 12C a step slider 60 is positioned and it is sized and configured to be inserted into ring support 52. Bottom ring 104 of CAR assembly 100 is configured and sized to fit onto ring support 52. Anvil assembly 28 which includes anvil disk 103 (not shown in FIG. 2 but shown in FIG. 1) of CAR assembly 100 is sized and configured to sit on trocar 38 when central member 70 is positioned inside blade pusher assembly 16 and when trocar 38 has been advanced past the distal end of blade pusher assembly 16.

For ease of understanding, housing 80 of FIG. 1 is shown as split into two halves 80A and 80B in FIG. 2. It should be noted that the two halves of housing 80 shown in FIG. 2 are in effect two parts that fit around blade pusher assembly 16 and central member 70 after the latter has been inserted into the former. After being connected, the two halves act as a single integrated part.

Operation of the elements described above will be described more fully below in conjunction with other Figures yet to be discussed.

Figure 3:
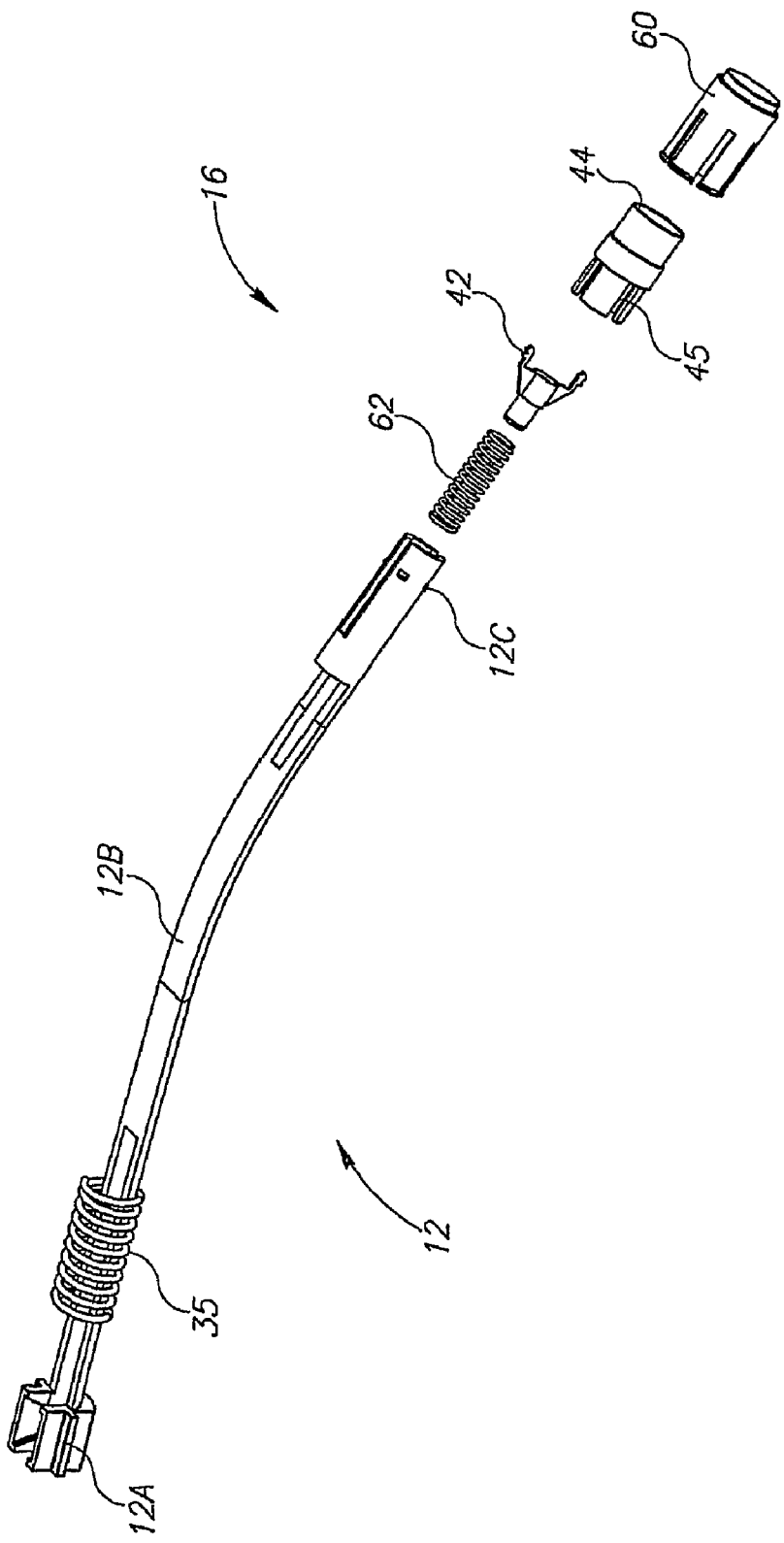
FIG. 3 shows an enlarged, partially exploded, view of the blade pusher assembly of the applicator shown in FIGS. 1 and 2.

Reference is now made to FIG. 3 in which an expanded view of blade pusher assembly 16 is shown. Blade pusher 12 allows for advancing or retracting blade element 44. Proximal end section 12A of blade pusher 12 of blade pusher assembly 16 is joined to its distal substantially cylindrical end 12C by linking section 12B. Blade pusher 12 of blade assembly 16 is comprised of a distal end section 12C which engages with a blade holder 45. When blade pusher 12 moves in the direction of its distal end, an anvil lock spring 62, positioned inside the substantially cylindrical distal end 12C of blade pusher 12 pushes against an anvil lock 42. The latter is positioned to lie against spring 62. Anvil lock 42 moves toward, and stops at, blade holder 45 which is mechanically and operationally in communication with blade element 44. Substantially cylindrical blade element 44 and blade holder 45 are positioned inside substantially cylindrical step slider 60 which in turn is positioned inside substantially cylindrical ring support 52 (shown for example in FIG. 2 above and 8B below) forming essentially concentric cylindrical shells centered on trocar 38 (FIG. 2). Further operation of the step slider 60, the blade element 44 and the blade holder 45 will be described below in conjunction with FIGS. 9A-13.

Figure 4:
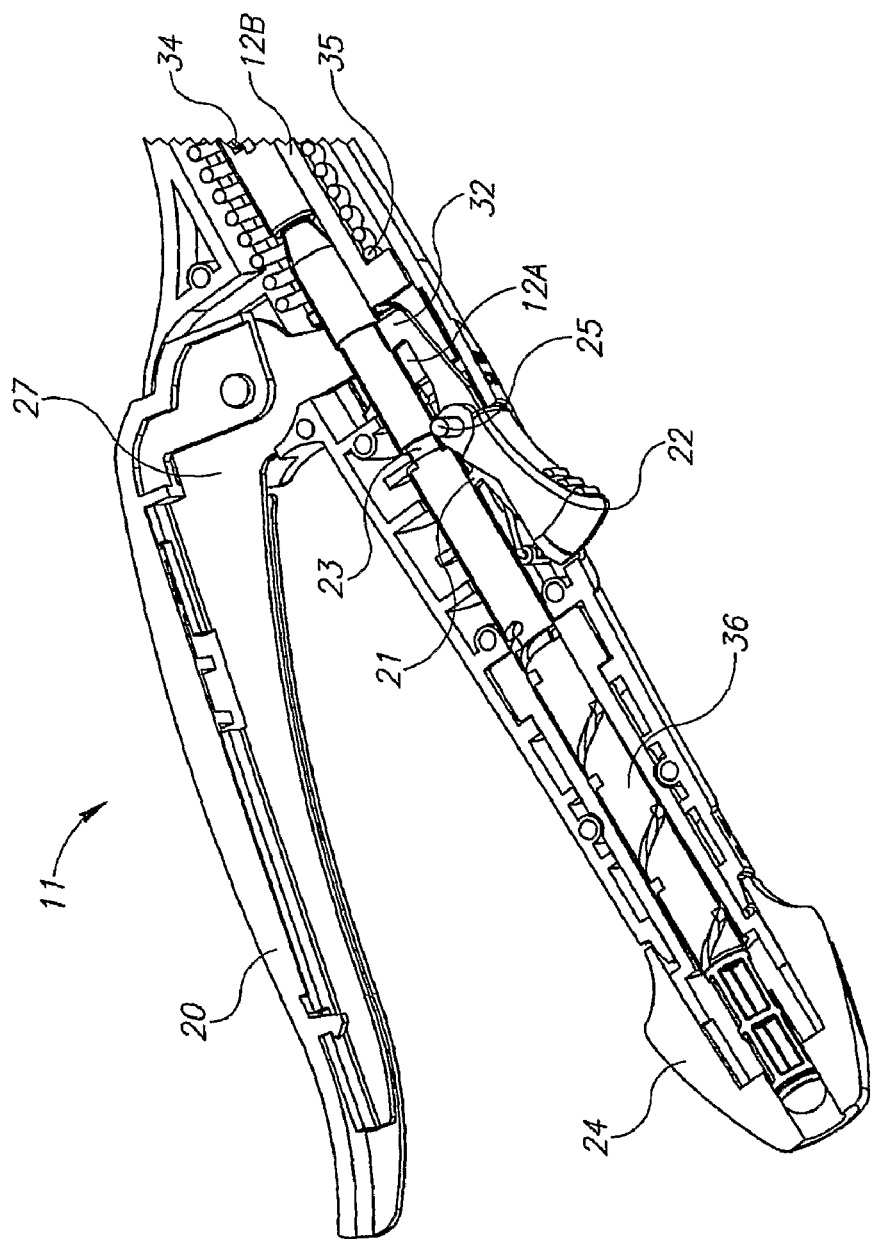
FIGS. 4 and 5 show a cut-away enlarged view of the proximal end of the CAR applicator shown in FIGS. 1 and 2 before and after activating the cut trigger of the applicator, respectively.
Figure 5:
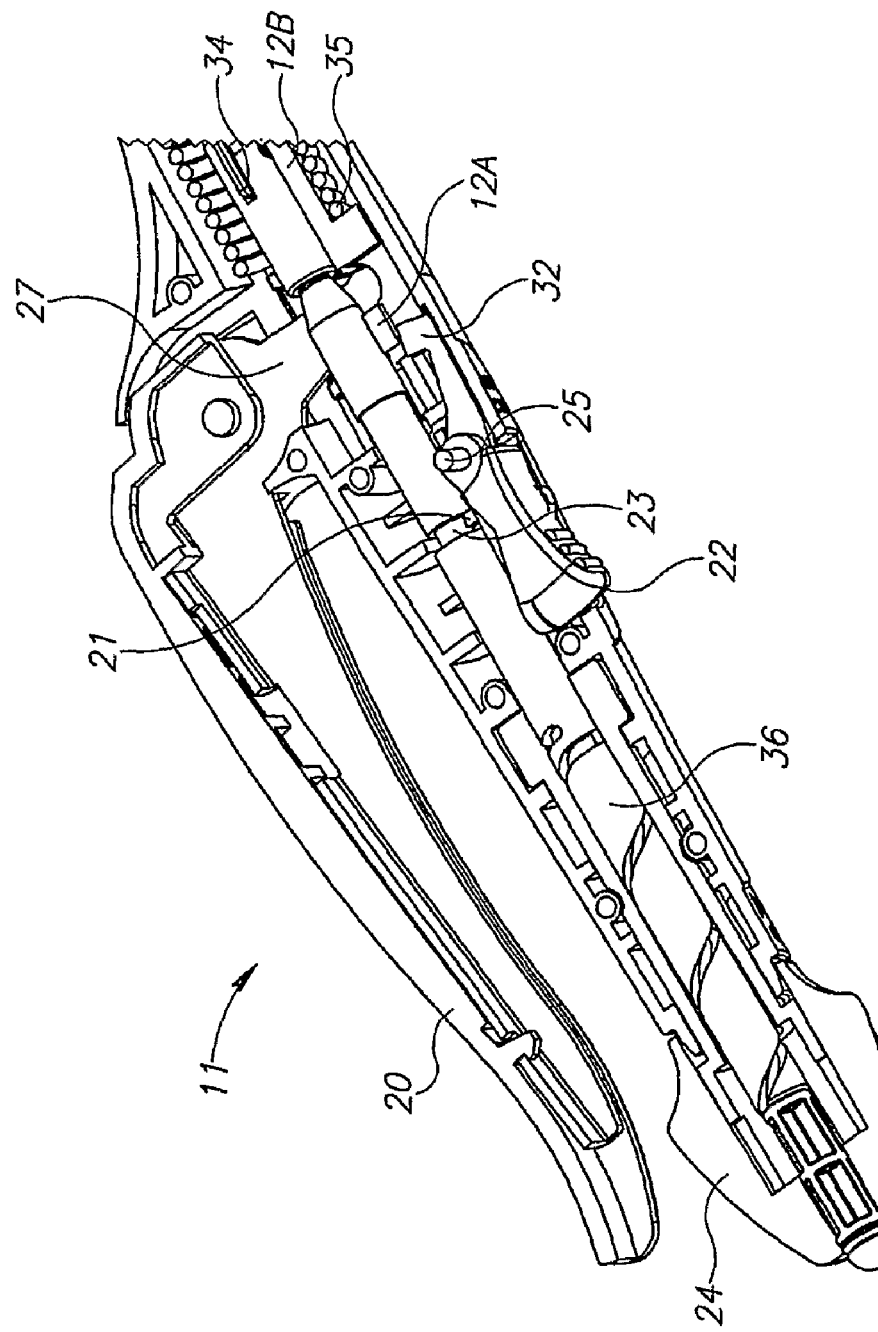

Reference is now made to FIGS. 4 and 5 in which the proximal end 11 of CAR applicator 10 is shown both before and after activation of cut trigger 22, respectively. The activation of cut trigger 22 and the squeezing of lever 20 allow blade element 44 (discussed in conjunction with FIG. 3 above and to be discussed again in conjunction with FIGS. 9A-13 below) to move up and cut tissue held between anvil disk 103 (FIG. 1) and bottom ring 104 (FIG. 1) of CAR assembly 100 to be described in greater detail in conjunction with FIGS. 6-7 below. When cut trigger 22 is pressed, cut trigger pin 21 moves out of cut slot 23 on helix 36. Cut trigger arm 32 moves downwardly away from the proximal end 12A of blade pusher 12 allowing lever 20 to be squeezed.

Lever 20 is in mechanical communication with the proximal end 12A of blade pusher 12 via lever arm 27. Arm 27 is positioned in and engages with the pocket formed at proximal end 12A of blade pusher 12. This pocket is best seen in FIG. 3. When lever 20 is squeezed, lever arm 27 rotates so that it moves and pushes blade pusher 12 (FIG. 3) bringing blade element 44 (FIG. 3) to its cutting position. As lever arm 27 pushes blade pusher 12 at its proximal end 12A, main spring 35 compresses. Compressed main spring 35 pushes proximal end 12A of blade pusher 12 in the direction of knob shaft 37 (best seen in FIG. 2) causing blade pusher 12 to return to its initial position after the cutting operation of CAR applicator 10 has ended.

Figure 6:
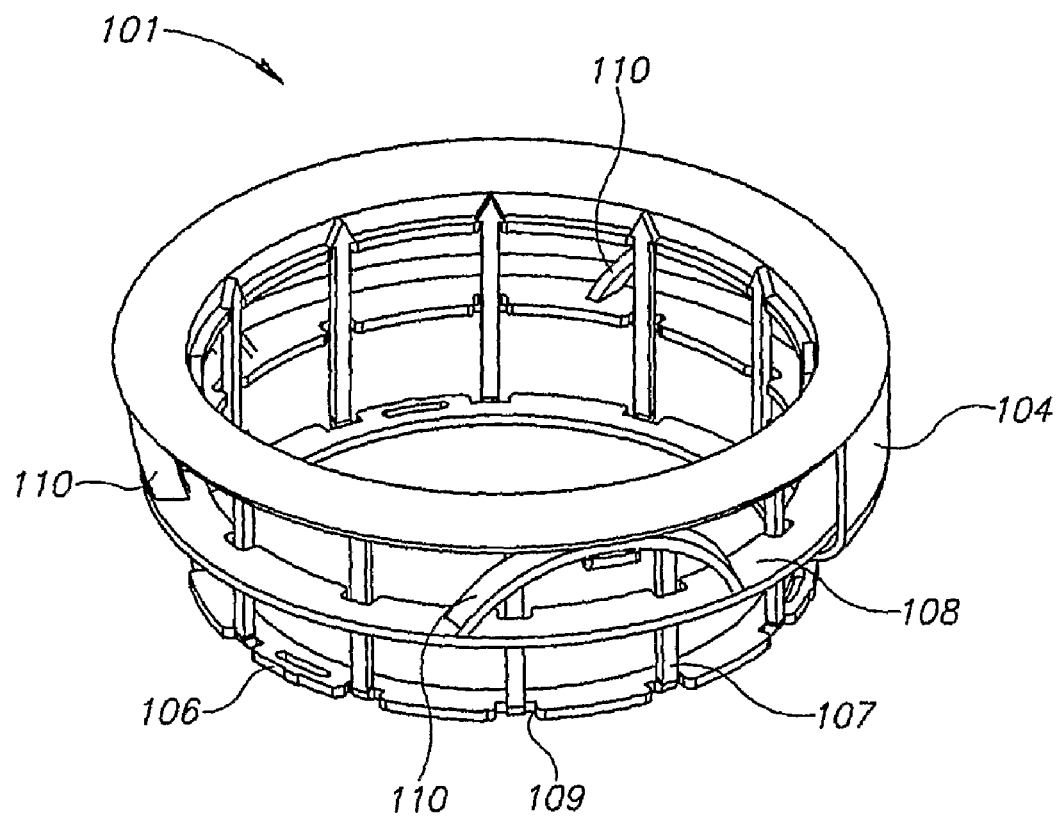
FIG. 6 shows an isometric view of the second portion of the CAR assembly constructed according to an embodiment of the present invention.
Figure 7:
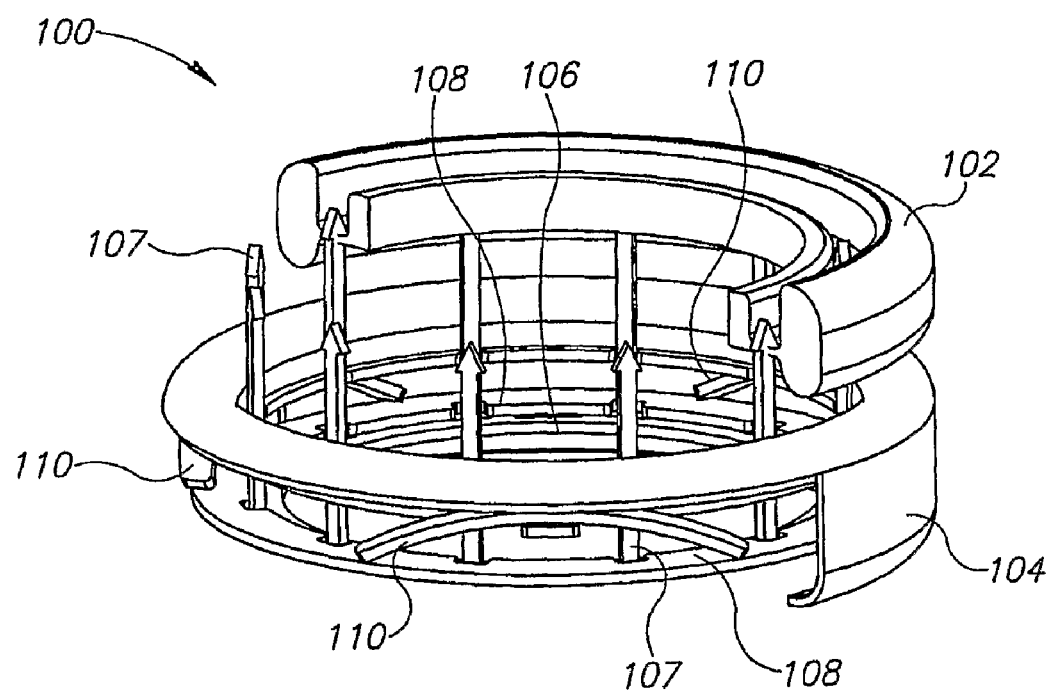
FIG. 7 shows an isometric view of the entire CAR assembly constructed according to an embodiment of the present invention.

Reference is now made to FIGS. 6 and 7 where partial cut-away side views of CAR assembly 100 are shown. FIG. 6 represents a cut away view of only the second portion 101 of CAR assembly 100. The entire CAR assembly 100 is shown in FIG. 7. CAR assembly 100 includes an anvil disk 103 (FIGS. 9A and 10A) formed of any of a large number of rigid plastics known to those skilled in the art and a bottom ring 104 which may be formed from any of a large number of plastics or metals known to those skilled in the art. Anvil disk 103 is formed to be comprised of an anvil ring 102 positioned on the disk's periphery and an anvil inner core 105 (the latter easily seen, for example, in FIGS. 9A and 10A). Anvil disk 103 may include holes into which the ends of needles 107, to be discussed below, may enter. Alternatively, no such holes need be included and needles 107 themselves pierce and enter plastic anvil disk 103 when a force of sufficient magnitude is exerted on them.

Bottom ring 104 girdles a needle ring 106 (partially obscured in FIG. 7 but readily visible in FIG. 6), CAR flange 108 and one or more spring elements 110. Needle ring 106 includes a plurality of barbed needles 107, each needle 107, typically but without intending to limit other possibilities, spaced substantially equidistant from its two nearest neighbors. Needles 107 are deployed in essentially a circular configuration to conform to the circumference of needle ring 106. Again such a configuration is exemplary only and not intended to be limiting.

Needles 107 may be formed integrally with needle ring 106. Alternatively, they may be joined to needle ring 106 by any of several methods known to those skilled in the art, such as welding, gluing, and pressure fitting. These methods are exemplary only and are not intended to be limiting. The shape of the barbs on the heads of needles 107 as shown in FIGS. 6 and 7 is exemplary only. Any generally penetrating shape may be used as the head of needles 107, even sharp heads without barbs.

CAR flange 108 is typically, but without intending to be limiting, formed from any of a large number of metals or plastics known to those skilled in the art. Needle ring 106 and the plurality of barbed needles 107 are typically, but without intending to be limiting, formed from any of a large number of metals or plastics known to those skilled in the art. The one or more spring elements 110 are made from a shape-memory alloy, typically, but again without intending to be limiting, nitinol. Also typically, but without intending to be limiting, spring elements 110, when in their unloaded austenite state, are arch-shaped. The spring elements are positioned to lie on CAR flange 108 between flange 108 and bottom ring 104. The top of the arch contacts the underside, that is the closest side, of bottom ring 104. When the shape-memory alloy from which spring elements 110 are formed is in its loaded stress-induced martensite state (or stress-retained martensite state), spring elements 110 lie substantially flat along CAR flange 108 below bottom ring 104. Spring elements 110 are positioned on CAR flange 108 so that their ends can move when going from the spring elements' uncompressed arched shape to the spring elements' flat compressed shape and vice versa.

Needle ring 106 is positioned below CAR flange 108. CAR flange 108 has indentations 109 along its inner generally circular circumference through which barbed needles 107 extend from needle ring 106 past CAR flange 108.

Spring elements 110 have been described herein as having an arched uncompressed configuration when not compressed and a flat configuration when compressed; these are essentially leaf springs. The present invention also contemplates other possible spring forms and configurations, including conventional coiled configurations.

In what has been described herein throughout, CAR assembly 100 has been described as having a separate CAR flange 108 and a needle ring 106. In other embodiments, there may be only a single element, essentially the needle ring with needles 107 affixed thereon. The CAR flange may be eliminated. In such an embodiment, spring elements 110 are positioned on the needle ring and they contact the bottom of bottom ring 104. The spring elements are movable on needle ring 106 and they are capable of moving from their compressed to uncompressed configurations/shapes and vice versa. In this latter embodiment, spring elements 110 are typically, but without intending to be limiting, deployed in their non-compressed austenitic state. When a CAR flange 108 is employed the spring elements 110 are typically deployed in their compressed martensitic state.

It should be noted that all ring or ring-shaped elements discussed herein, including the claims, with respect to the CAR assembly 100, contemplate, in addition to the use of circular-shaped elements, the possibility of using elliptical, oval or other shaped elements. The use of "ring" should not be deemed as shape limiting for the rings elements described and illustrated hereinabove. These ring elements include, but are not limited to, the needle ring 106, the CAR flange 108, and the bottom ring 104.

It should also be noted that the use of the term "bottom ring" as a term for element 104 should not be deemed as denoting anything about the specific spatial and functional relationship between this element and the other elements of the CAR assembly 100. The spatial and functional relationship of element 104 and the other elements of assembly 100 are defined by the description and the drawings.

Figure 8A:
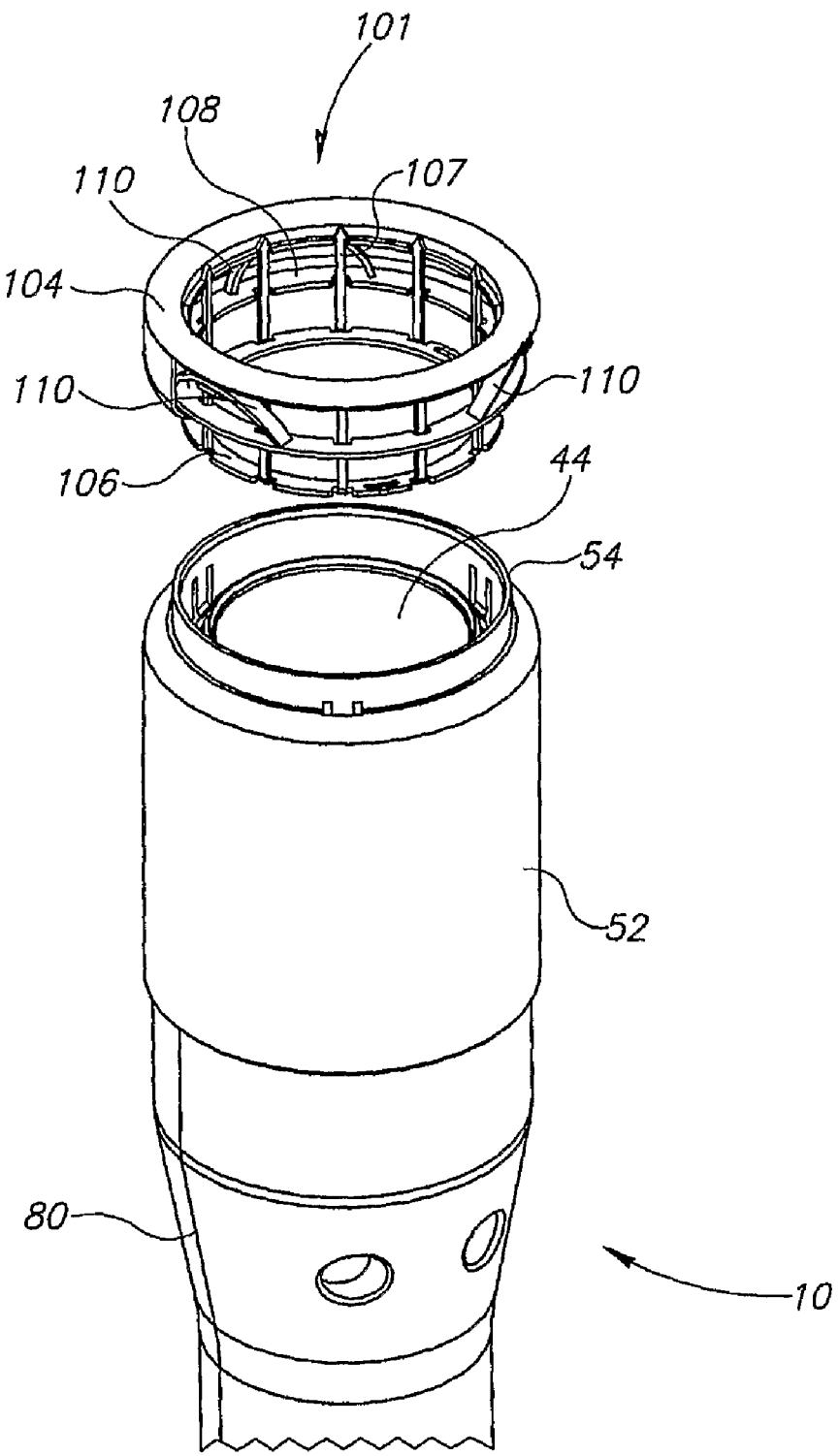
FIGS. 8A and 8B show a CAR assembly constructed according to the present invention being brought for positioning in a CAR applicator also constructed according to an embodiment of the present invention.
Figure 8B:
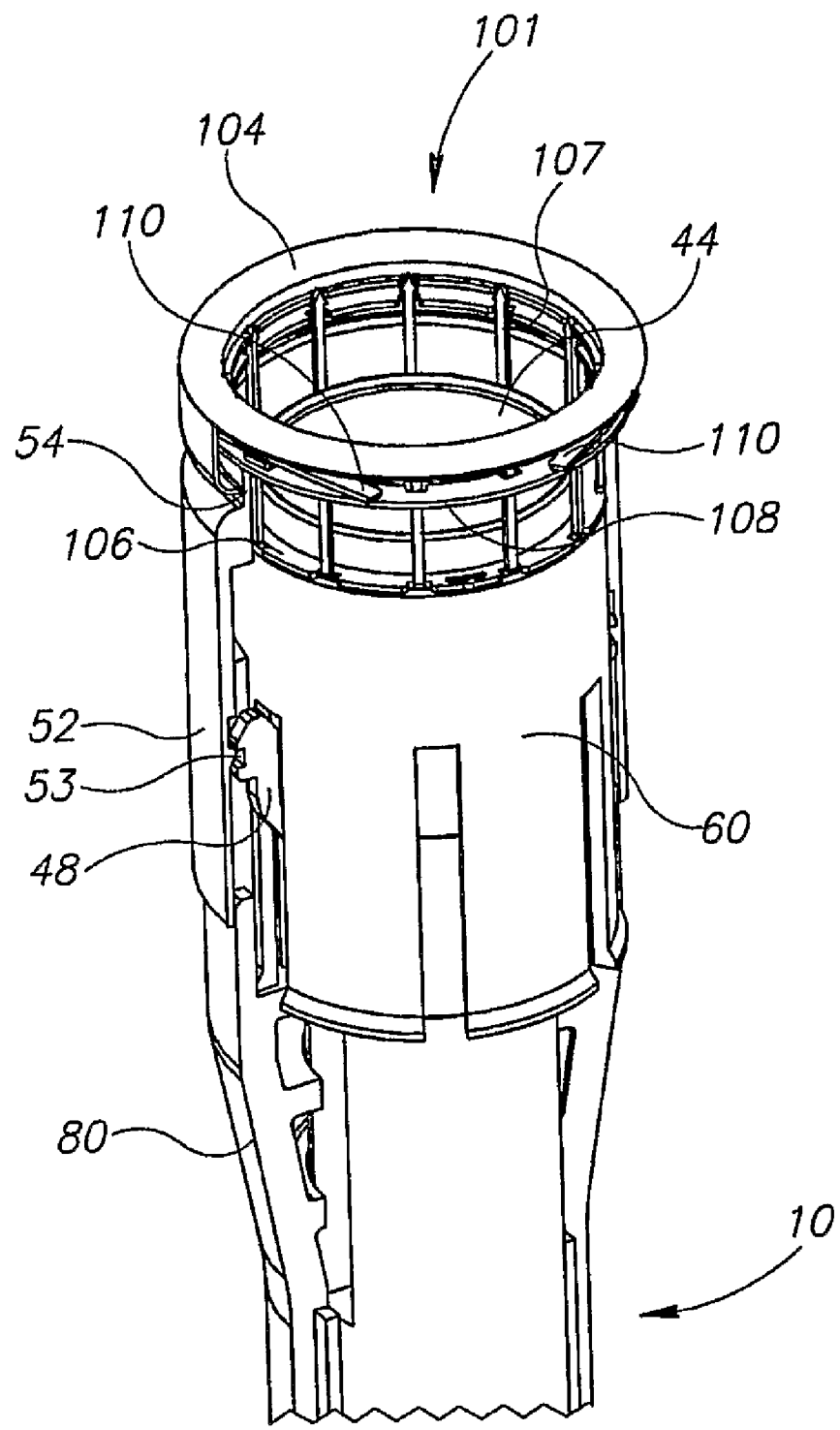

Reference is now made to FIGS. 8A and 8B which show two views of the second portion 101 of CAR assembly 100 in the process of being positioned and positioned on the distal end of CAR applicator 10, respectively. In FIGS. 8A and 8B, the rest of CAR applicator 10 is not shown. In FIG. 8A, CAR assembly 100 is shown with spring elements 110 in their non-compressed arched shape and with the shape-memory alloy from which they are formed in its non-stressed austenite phase. In FIG. 8B, spring elements 110 are compressed and flattened and the shape-memory alloy from which they are formed is in its stressed-induced martensite phase.

In FIGS. 8A and 8B, the second portion 101 of CAR assembly 100, as discussed previously, is shown to be comprised of a bottom ring 104, a CAR flange 108, a needle ring 106, a plurality of needles 107, here barbed needles, and a plurality of spring elements 110 formed of a shape-memory alloy. While somewhat obscured in FIG. 8B, there are in fact three spring elements located on CAR flange 108. This is intended to be an exemplary but non-limiting, number. In some instances there may even be a single spring element. Each spring element in FIGS. 8A and 8B is located an equidistance from its nearest neighbors on substantially circular CAR flange 108. Such an equidistant configuration is not intended to limit the use of other configurations and spacings.

The distal end of CAR applicator 10 includes a blade element 44, load lip 54, a ring support 52, applicator housing 80 and a step slider 60. Load lip 54 functions as a stress applier to spring elements 110 when loading the second portion 101 of CAR assembly 100 onto the distal portion of CAR applicator 10 as in FIG. 8B. When going from FIG. 8A to FIG. 8B, spring elements 110 have been flattened and the shape-memory alloy from which the spring elements are formed has been brought by load lip 54 to its stress-induced martensite state from its unstressed austenite state. The function of the other parts in these Figures and their interrelationship will be discussed in greater detail below in conjunction with FIGS. 9A through 13B.

As can readily be seen in FIG. 7, the circumference of the needle ring 106 is smaller than that of CAR flange 108. Accordingly, while CAR flange 108 is aligned with load lip 54, needle ring 106 is positioned and held inside ring support 52. Needle ring 106 rests against step slider 60 to be discussed below in conjunction with FIGS. 9A-13B.

In the Figures herein and in the accompanying discussion, a load lip 54 is described as providing the load that brings the alloy of spring elements 110 into its martensitic phase and the spring elements to their compressed flat configuration. It is readily understood that other load providing means, such as load teeth or load protrusions, positioned on the distal edge of ring support 52 at the distal end of the CAR applicator 10 may also be used. As will be described in greater detail in conjunction with FIG. 14 below, pre-loading, i.e. compressing, spring elements 110 allows direct use of only the bottom portion of the stress-strain hysteresis curve for the shape-memory alloy shown. Only when the CAR flange 108 is released is a force applied on the tissue.

While we have described the flattening of spring elements 110 as being stress-induced, it should be understood that they may also be induced by a combination of stress and cooling as is typical with shape-memory alloys.

FIGS. 9A-13B, to which reference is now made, illustrate the operation of CAR assembly 100 in effecting anastomosis.

Figure 9A:
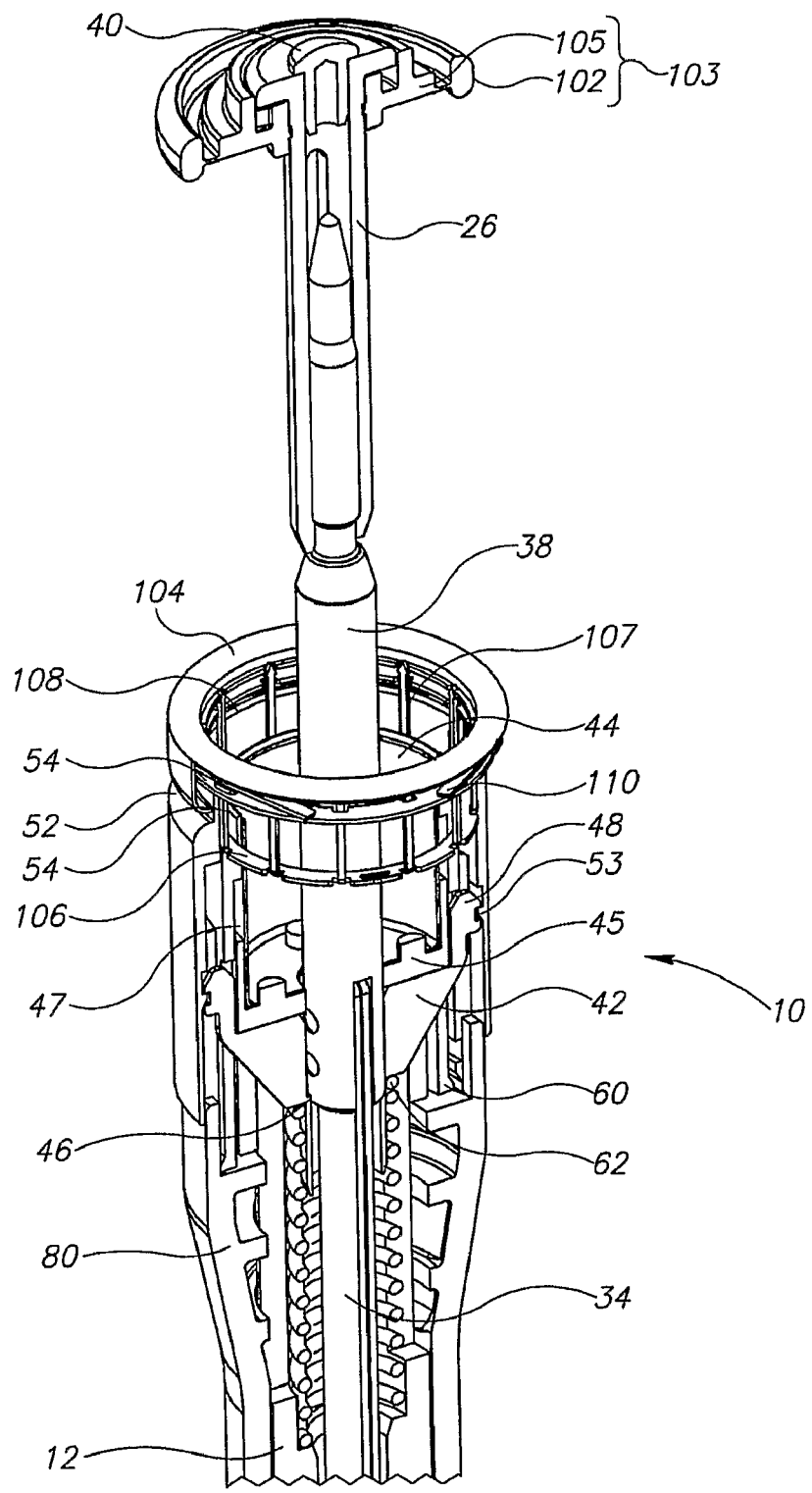
FIG. 9A shows a cut-away isometric view of the distal end of the CAR applicator and of the CAR assembly prior to applying the CAR assembly to the site requiring anastomosis.
Figure 9B:
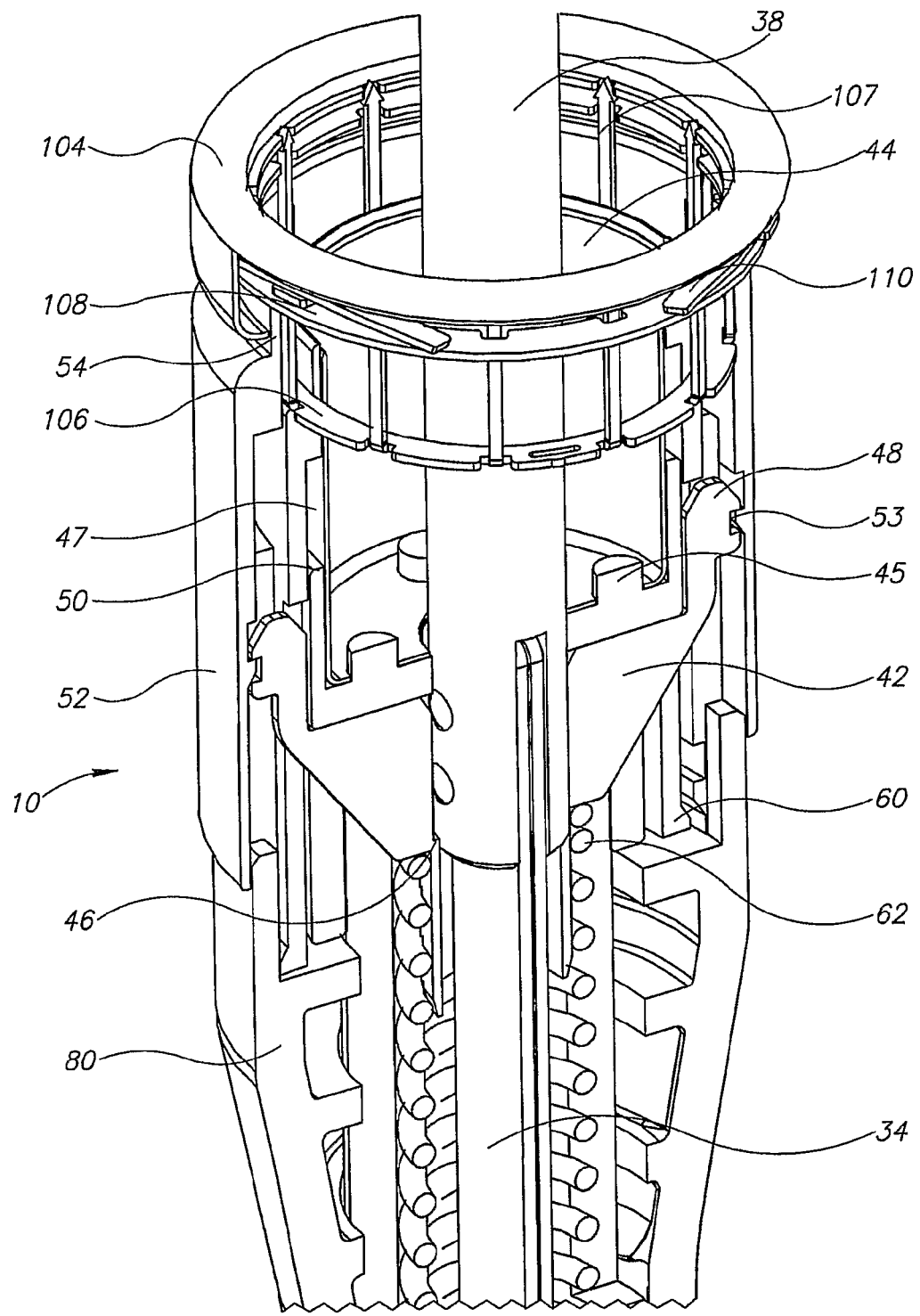
FIG. 9B is an enlarged view of the distal end of the CAR applicator and second portion of the CAR assembly shown in FIG. 9A.

FIGS. 9A and 9B show the initial step in the method of operation of CAR applicator 10 (best seen in FIGS. 2 and 3) and CAR assembly 100 (best seen in FIG. 7) after deploying the second portion 101 of CAR assembly 100 on the distal end of CAR applicator 10. The deploying procedure has been shown and discussed above in conjunction with FIGS. 8A and 8B. FIG. 9B is an expanded view of the lower portion of FIG. 9A. In both FIGS. 9A and 9B, shape memory alloy spring elements 110 have been compressed as previously discussed either by stress or cooling and stress.

Figure 9C:
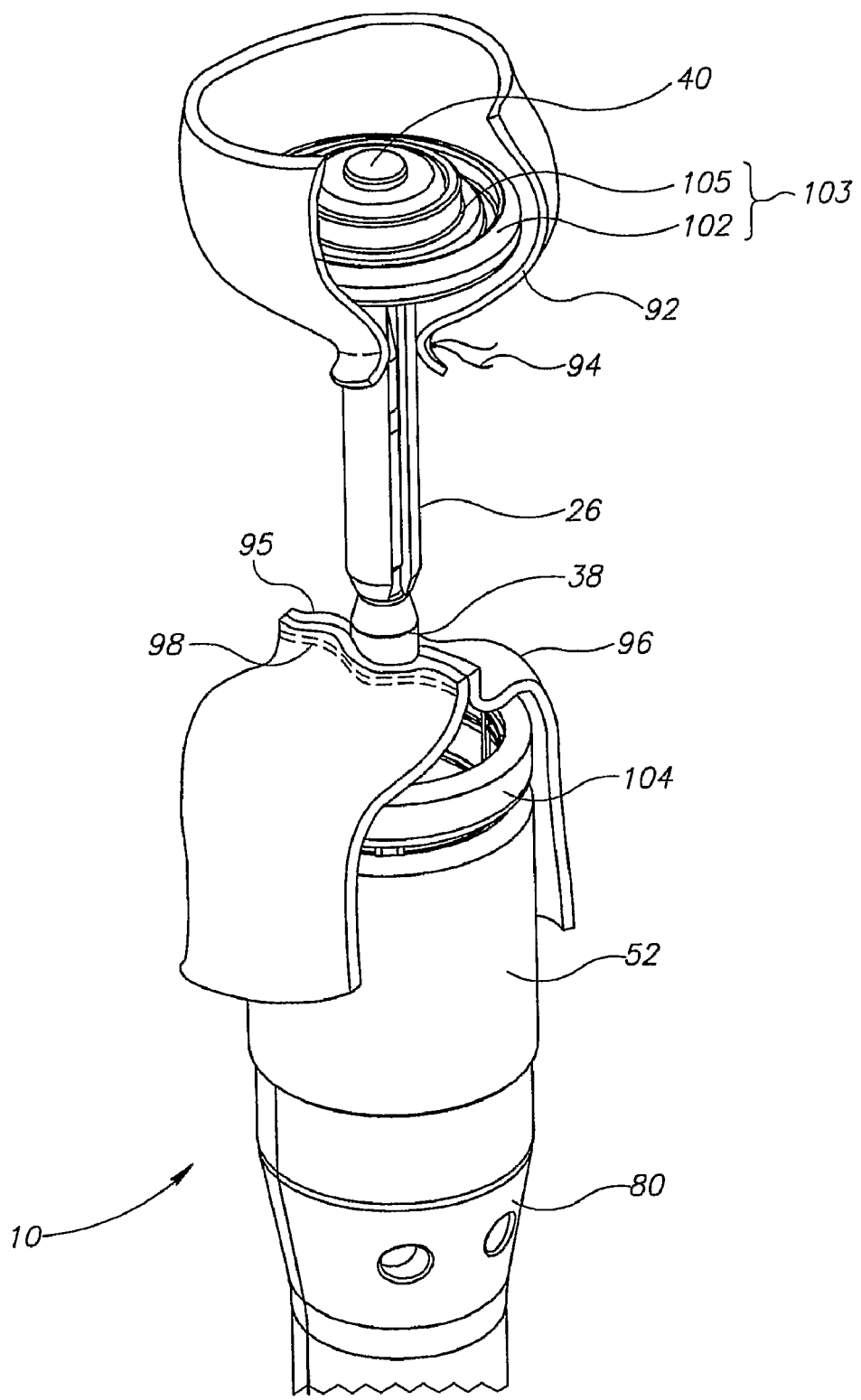
FIG. 9C shows the CAR assembly and CAR applicator of FIGS. 9A and 9B with tissue attached, the tissue intended to undergo anastomosis.

Turning control knob 24 (FIG. 1) on CAR applicator 10 (FIG. 1) extends trocar 38 past the distal end of applicator 10. Trocar 38 is joined by any of several means well-known to those skilled in the art to trocar connecting link 34 (best seen in FIG. 2). Anvil disk 103 is joined to trocar 38 by anvil rod 26. Rod 26 is tapered at its proximal end and extends into anvil disk 103 at its distal end. As shown in FIG. 9C, while trocar 38 is extended past the distal end of CAR assembly 10, a first cut end 92 of a cut body lumen is placed over anvil disk 103 and attached below disk 103 by a purse string suture 94. FIG. 9C is a full non-cut away view related to FIGS. 9A and 9B which includes the tissue sections to undergo anastomosis.

Prior to extending trocar 38 out of the distal end of CAR applicator 10, the applicator is inserted into the second part 96 of the severed lumen. This part has been sealed off at its end, herein called the second end 95, by any of several methods of suturing or stapling 98 known in the art. This sutured or stapled second end 95 is placed over the distal end of applicator 10, including over deployed bottom ring 104. When trocar 38 is advanced, it pierces this sutured or stapled second end 95 of the cut lumen. Pierced second end 95 effectively drapes over the distal end of applicator 10 and bottom ring 104 positioned thereon.

In addition to the elements previously discussed and numbered in previous Figures, additional elements are present at or near the distal end of CAR applicator 10 in FIGS. 9A and 9B. The distal end of CAR applicator 10 is encased in housing 80. As also noted previously, spring elements 110 at the second portion 101 of CAR assembly 100 are in their compressed/flattened configuration and the alloy from which the spring elements are formed are in their stressed-induced martensite state.

Figure 10A:
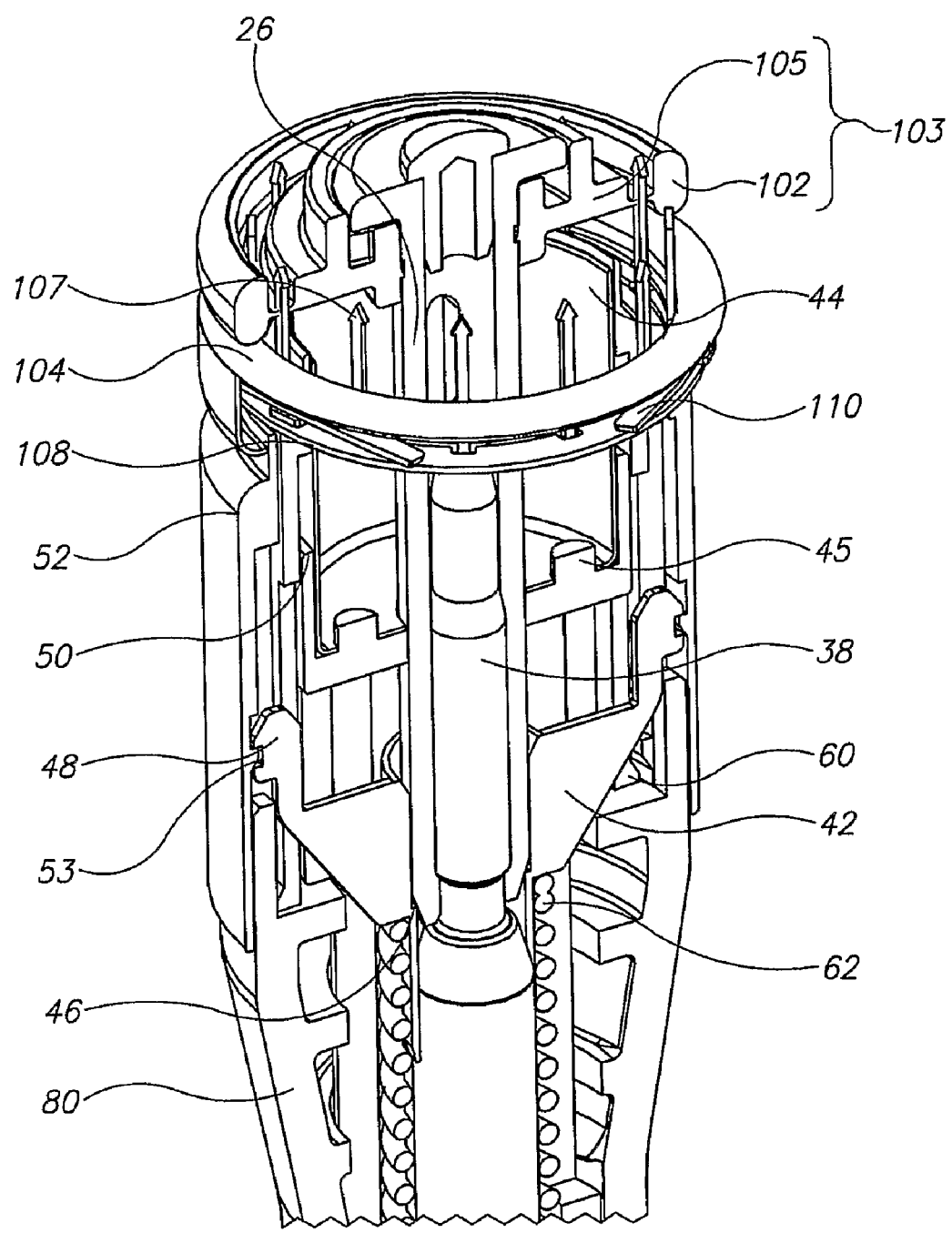
FIGS. 10A, 11A, 12 and 13A show the sequence of steps in the method of operation of the CAR assembly and CAR applicator shown in FIGS. 9A and 9B both constructed according to an embodiment of the present invention.

Shown in FIG. 9A is blade element 44 supported by blade holder 45 which is pushed by blade pusher 12. Anvil lock 42 (also shown in FIG. 3) lies above anvil lock spring 62 and has an anvil lock step 46 which locks anvil rod 26 when it is pulled back into housing 80 (FIG. 10A). Anvil lock 42 is also connected to ring support 52 by anvil lock arms 48 engaging with support ring flanges 53, forming an essentially single moving part therewith. Once anvil rod 26 engages anvil lock step 46 of anvil lock 42, rod 26 and lock 42 move downwards together in the direction of CAR applicator's 10 proximal end. Step slider 60, which rests on inside projections of housing 80, is separated from blade holder 45 by a gap 47 between step slider 60 and blade holder flange 50. The function of these parts will become evident and better illustrated in the course of the discussion which follows. The parts positioned at or near the distal end of CAR applicator 10 may be made from any of many metals or plastics known to those skilled in the art.

In FIG. 10A, to which reference is now made, anvil disk 103 has been brought close to bottom ring 104. The purse string attached tissue 92, attached to and surrounding anvil disk 103, and the stapled tissue 96, positioned over bottom ring 104 and the distal end of CAR applicator 10, are pierced by needles 107 of needle ring 106 as anvil disk 103 is brought towards bottom ring 104. Needles 107 enter and, as shown, pass through plastic anvil disk 103.

Moving anvil disk 103 to which the purse string attached tissue 92 has been affixed is effected by turning control knob 24 (FIG. 1). Knob 24 is in mechanical communication with trocar 38 inter alia by trocar connecting link 34, as has been discussed above in conjunction with FIG. 2. When moving from FIG. 9A to FIG. 10A, anvil disk 103, anvil rod 26 and trocar 38 are seen as being withdrawn toward and into housing 80, respectively.

In FIG. 10A, anvil rod 26 has engaged with anvil lock 42 at anvil lock step 46. Anvil rod 26, by engaging with anvil lock 42 pulls anvil lock 42 down as rod 26 is being retracted. This compresses anvil lock spring 62. Since anvil lock arms 48 engage with ring support flanges 53 on the internal side of ring support 52, support 52 also moves down. Bottom ring 104 moves downward along with ring support 52. As ring support 52 moves down it exposes needles 107 and releases its grip from needle ring 106 that holds bottom ring 104 in place. By piercing anvil disk 103, needles 107 help keep a constant gap between anvil ring 102 and bottom ring 104.

Figure 10B:
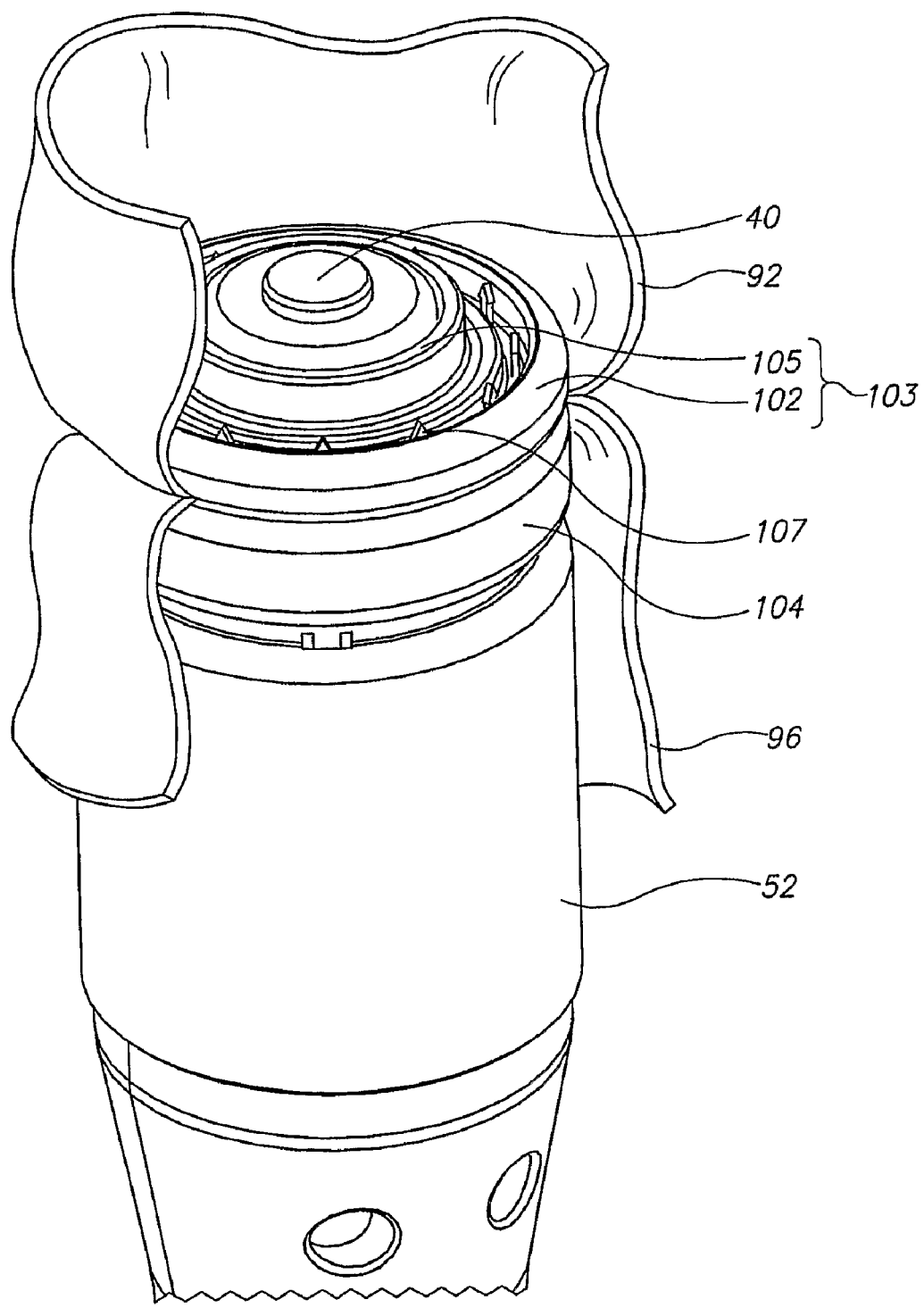
FIGS. 10B, 11B, and 13B show the position of the tissue to undergo anastomosis at the stages of operation shown in FIGS. 10A, 11A and 13A, respectively.

FIG. 10B shows a view of CAR assembly 100 and the distal end of CAR applicator 10 together with a cut-away view of the tissue to undergo anastomosis. FIG. 10B is presented at the same stage of operation as is shown in FIG. 10A. The purse string attached tissue 92 and the sutured or stapled tissue 96 are shown as being held between anvil ring 102 and bottom ring 104. The purse string 94 and suture/staples 98, shown in FIG. 9C, are obscured in FIG. 10B by bottom ring 104 and anvil ring 102.

Figure 11A:
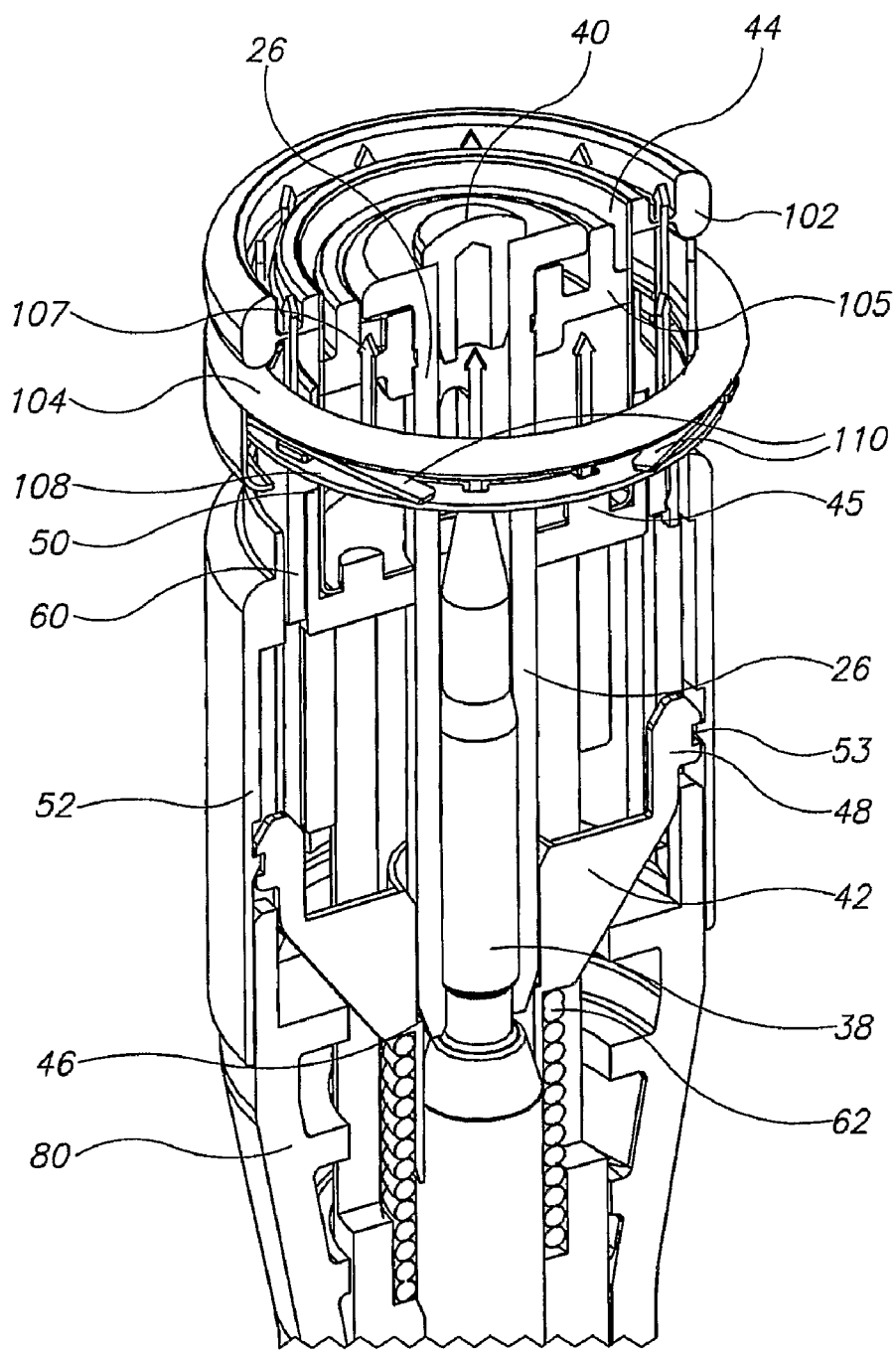

In FIG. 11A to which reference is now made, step slider 60 moves or "steps" up and gap 47 (best seen in FIGS. 9A and 9B) closes. Closure of this gap is effected when blade holder flange 50 engages with step slider 60. As blade element 44 moves up, it cuts both the purse string tied tissue 92 attached to anvil disk 103 and the tissue 96 draped over bottom ring 104. Additionally, plastic anvil disk 103 is cut into two concentric parts, an anvil ring inner core 105 which remains attached to anvil rod 26 and a free outer anvil ring 102. The latter remains detached from anvil rod 26 and is held in place by needles 107. Needle ring 106 is substantially stationary until anvil disk 103 is cut after which needle ring 106 is released from ring support 52.

When needles 107 penetrate anvil ring 102 they connect CAR bottom part 101 and anvil disk 103. At the same time needle ring 106 is released from ring support 52 so that the whole CAR assembly 100 is held only by anvil rod 26. Once anvil disk 103 is cut, CAR assembly 100 is actually held by blade element 44.

Figure 11B:
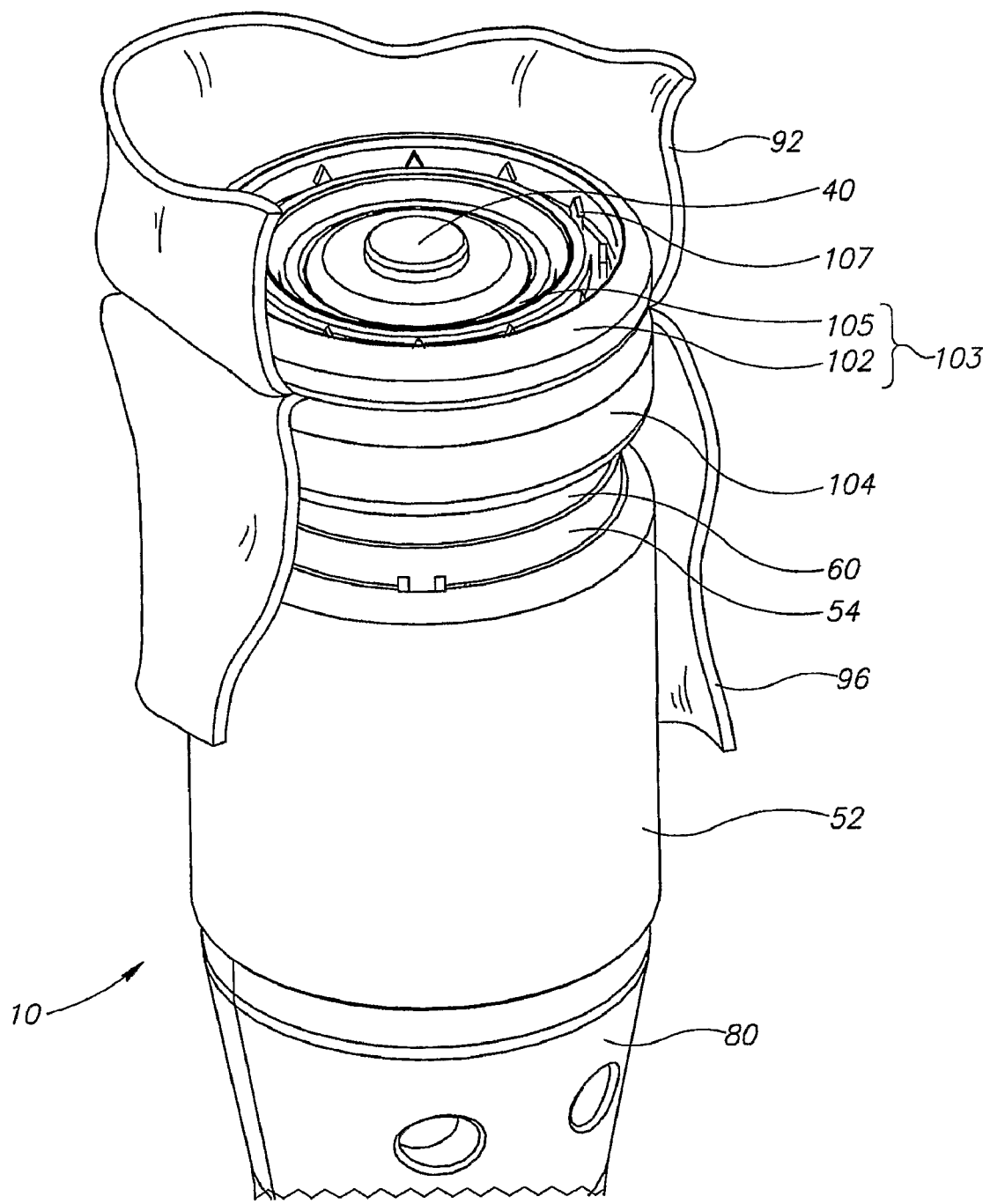

FIG. 11B shows a view of CAR assembly 100 and CAR applicator 10 together with a cut-away view of the tissue to undergo anastomosis. FIG. 11B is presented at the same stage of operation as is shown in FIG. 11A. FIG. 11B is very similar to FIG. 10B but the view of FIG. 11B shows the beginning of the separation of bottom ring 104 from the distal end of CAR applicator 10.

Figure 12:
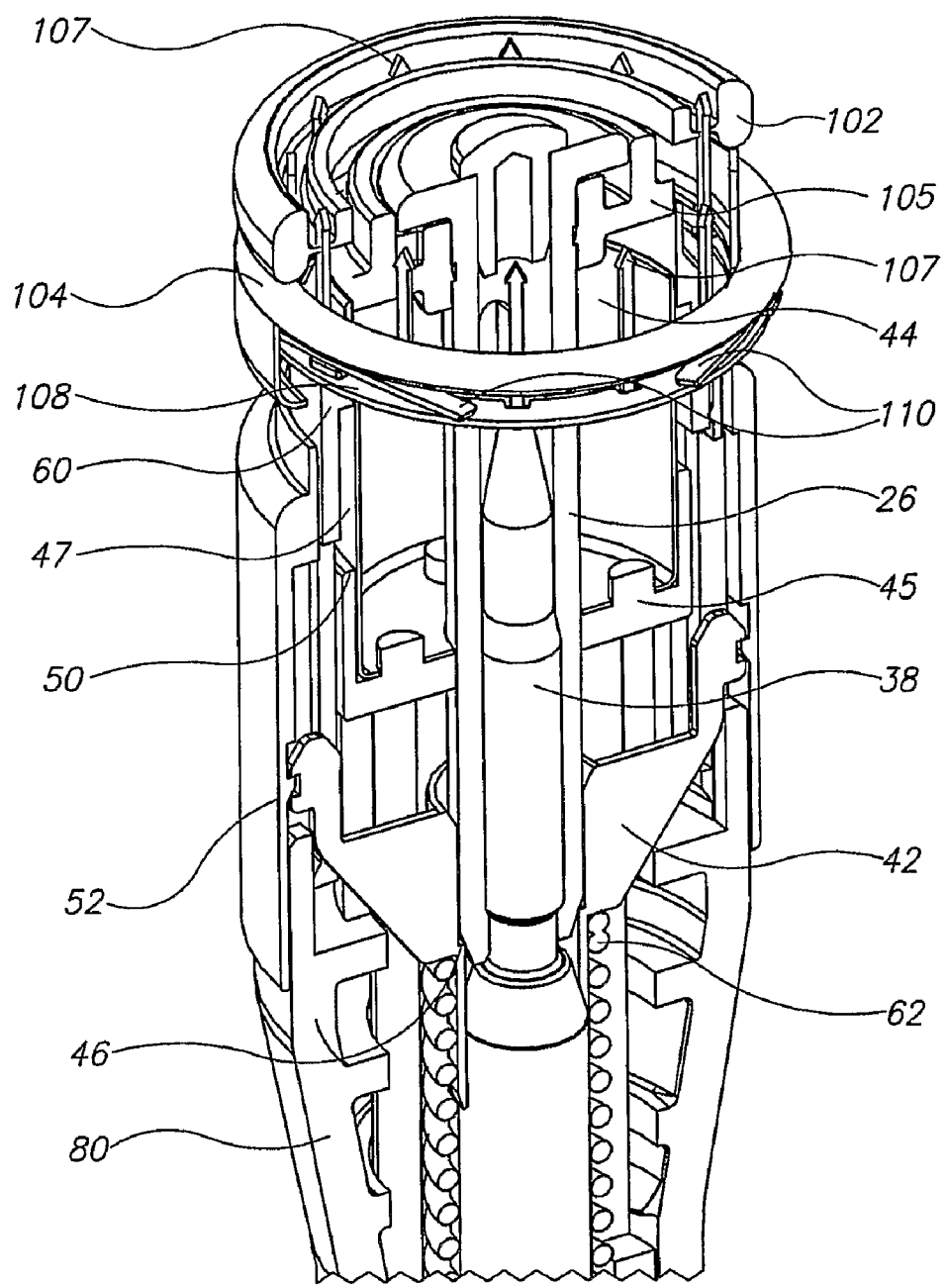

In FIG. 12, with the cutting operation completed, blade element 44 and blade holder 45 are pulled back by blade pusher 12 with which, as discussed in conjunction with FIG. 3 above, they are in mechanical connection. These parts are retracted by releasing lever 20 (FIG. 1). Meanwhile, bottom ring 104 of CAR assembly 100 detaches completely from step slider 60 allowing blade element 44 to release from anvil ring 102. When blade element 44 is pulled back, step slider 60 stops CAR assembly 100 and frees its bottom portion 101 from blade element 44. CAR assembly 100 is thus completely free from the distal end of CAR applicator 10.

Figure 13A:
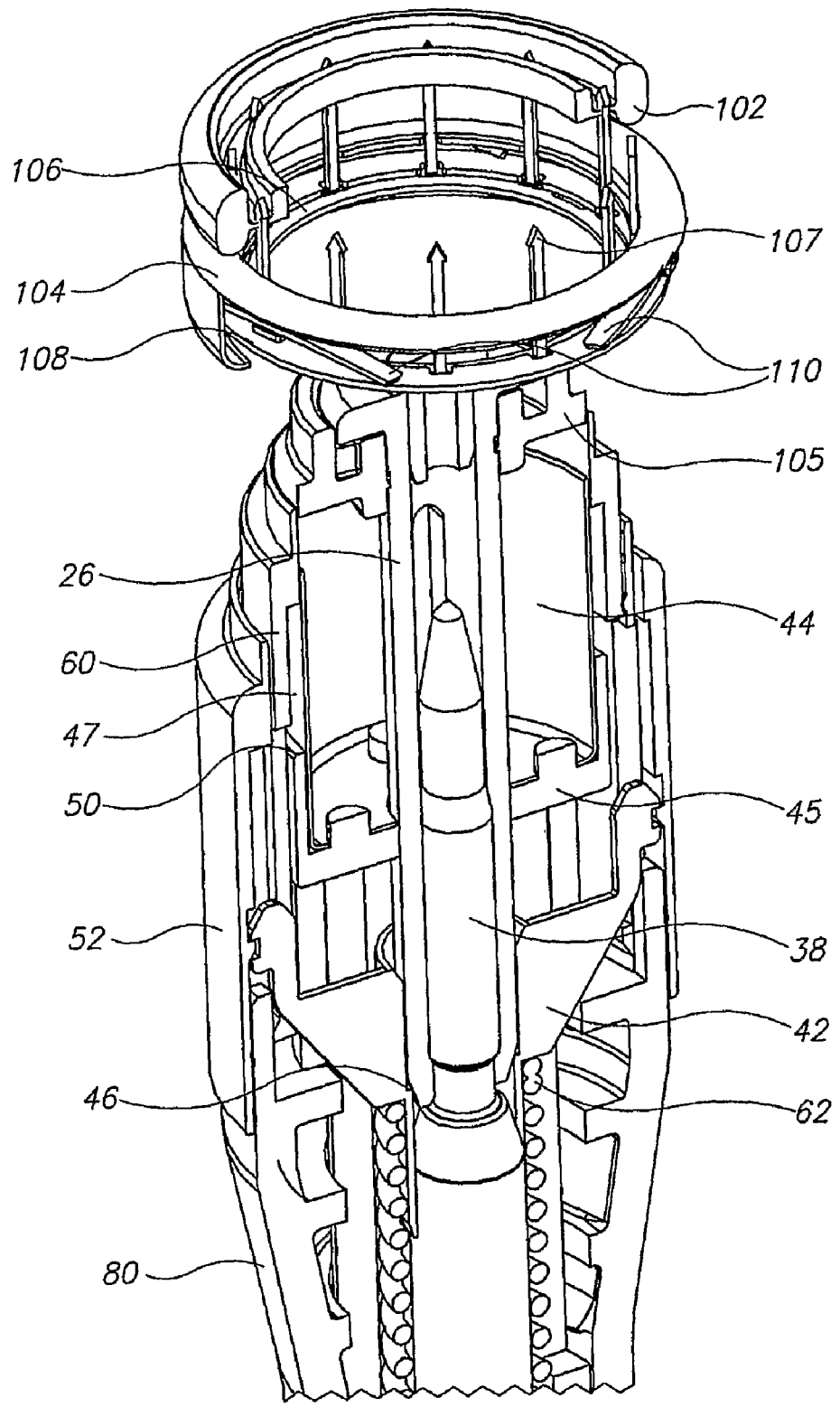

FIG. 13A, to which reference is now made, shows anvil and bottom rings 102 and 104, respectively, completely disengaged from CAR applicator 10. Still attached to anvil rod 26 is the inner circular core 105 cut from anvil disk 103 in FIG. 11A. In FIG. 13A, spring elements 110 begin to arch and abandon their flattened shape as they are no longer compressed by load lip 54. The arching spring elements 110, in force contact with bottom ring 104, exert a force that compresses the tissue sections held between disengaged bottom ring 104 and anvil ring 102.

Figure 13B:
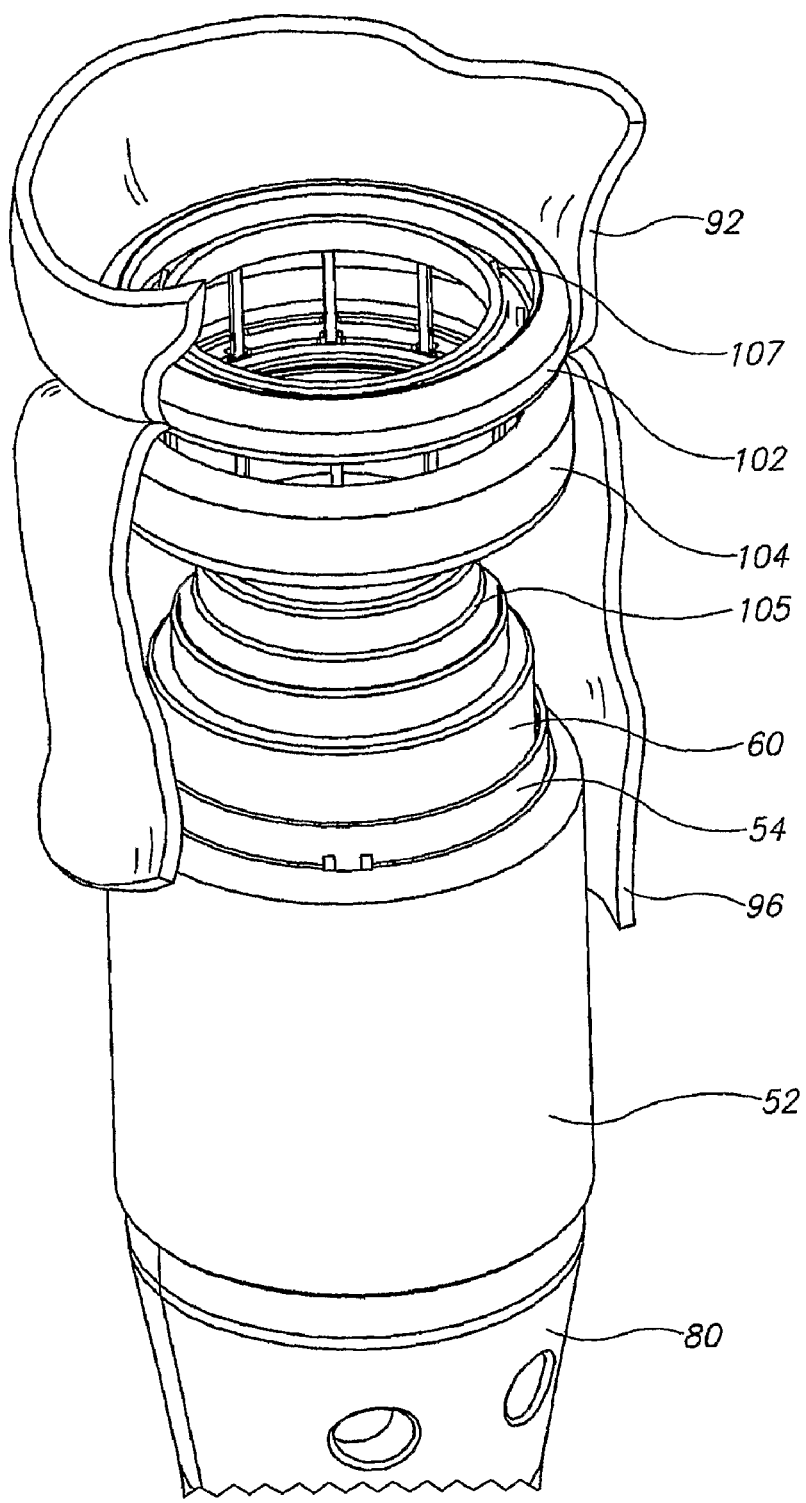

CAR applicator 10, anvil ring inner core 105, and anvil rod 26 are pulled away from the anastomosis site leaving the tissue as shown in FIG. 13B held between anvil ring 102 and bottom ring 104 to undergo anastomosis. After anastomosis, CAR assembly 100 is expelled from the body. In the case of anastomosis of the bowel, expulsion is through the anus.

While obscured in FIG. 13B, there are two donut shape pieces of cut tissue attached to retracted anvil rod 26. In FIG. 13B, anvil rod 26 and the attached donut-shaped pieces of tissue are inside blade 44 and therefore not visible.

It should be noted that in FIGS. 11A, 12A and 13A barbed needles are still inserted into anvil ring 102. The distance between anvil ring 102 and bottom ring 104 gradually closes as spring elements 110 arch. The compressive force on the tissue intended to effect anastomosis is generated by shape-memory alloy spring elements 110 acting on rings 102 and 104. As discussed further below this compressive force is essentially a constant compressive force.

It should also be borne in mind that the applicator 10 discussed herein with CAR assembly 100 is only exemplary and not intended to be limiting. Other applicators may also be designed by persons skilled in the art that may be used with CAR assembly 100.

In other places in this specification and claims, the following elements of CAR assembly 100 may be referred to in other terms: needle ring 106 may be referred to as needle bearing support, CAR flange 108 as flange, anvil ring 102 as first compression element, anvil disk 103 as upper portion, and bottom ring 104 as second compression element. Other elements in assembly 100 may similarly have different, but essentially equivalent, terminology.

Figure 14A:
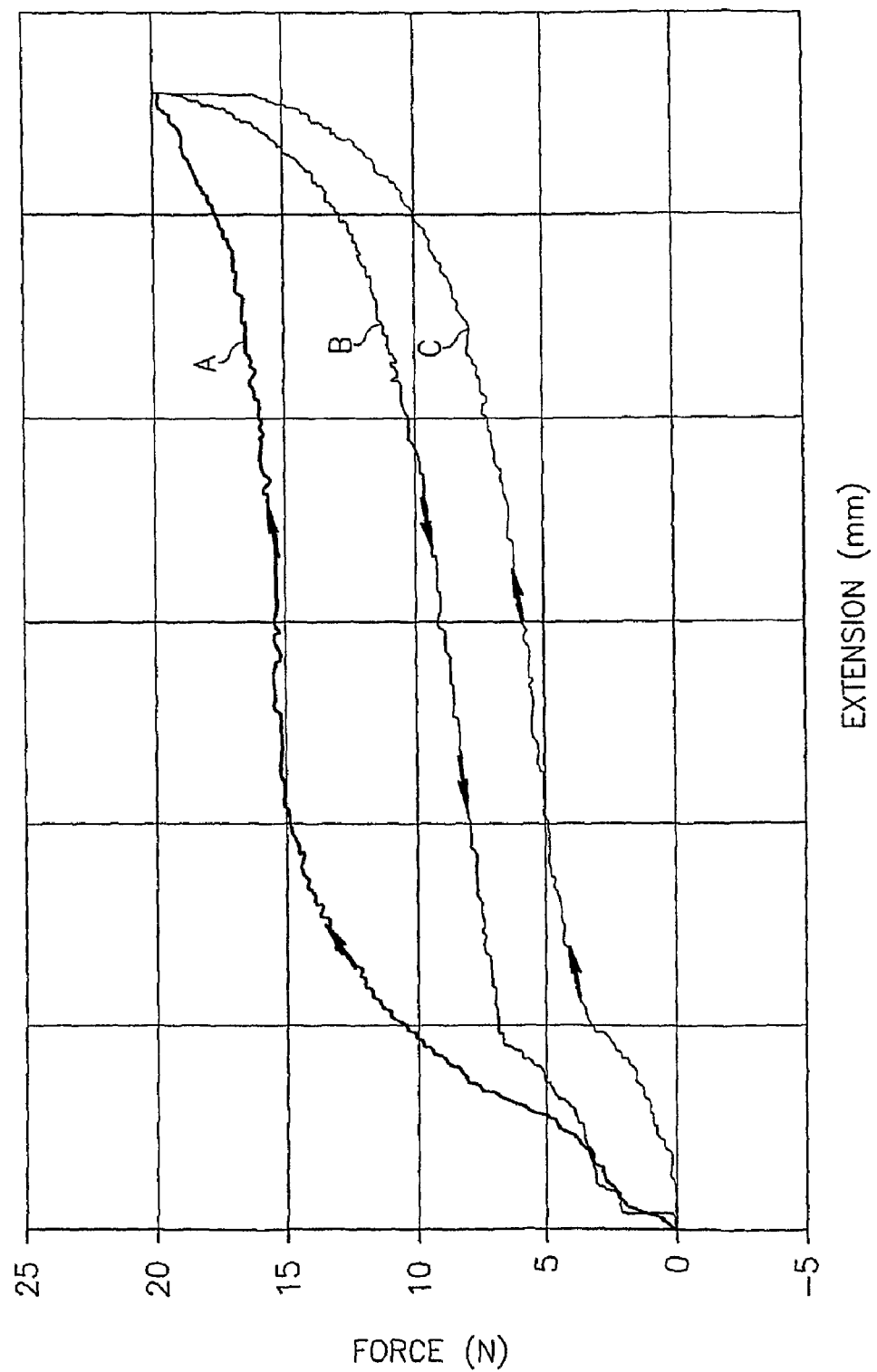
FIGS. 14A and 14B show typical shape-memory alloy stress-strain hysteresis loops produced by the shape-memory elements of a CAR assembly constructed according to an embodiment of the present invention.
Figure 14B:
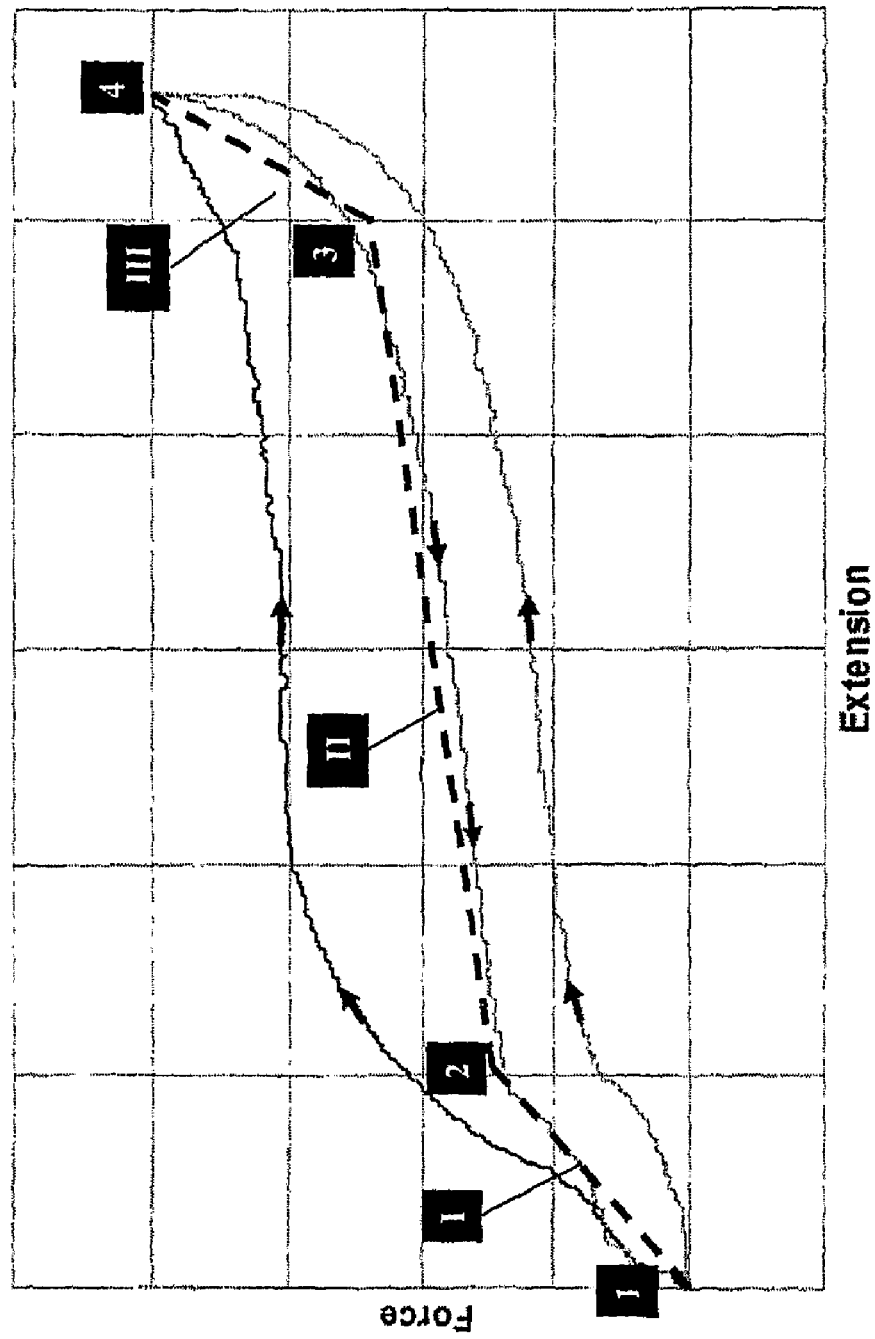

In FIGS. 14A and 14B, to which reference is now made, force-extension-compression hysteresis loops for the CAR assembly having spring elements formed of a shape-memory (SM) alloy, here nitinol, are shown. FIGS. 14A and 14B are essentially identical except for the additional annotation in FIG. 14B required for the discussion below.

As noted above, the spring elements 110 of the CAR assembly of the present invention are constructed of a shape-memory alloy, typically but without intending to be limiting, Ni—Ti alloy. They make use of the substantially "plateau-like" region in curve B of the hysteresis loops shown. Curve B represents the removal of the shape-changing stress from spring elements 110. "Plateau-like" region II in curve B (between points 2 and 3 in FIG. 14B) indicates that a slowly decreasing force is exerted on the tissue for which anastomosis is being effected over a defined extension range. While the rate of change of force (F) with respect to extension (x), i.e. dF/dx, in the "plateau-like" region II, is not truly zero, it is significantly smaller than the rate of change in the other regions (regions I and III) of curve B in FIG. 14B. Alternatively, the situation in FIGS. 14A and 14B can be discussed in terms of the material's Young's modulus as follows. The Young's modulus of the material in the "plateau-like" region (region II in FIG. 14B between points 2 and 3 in the curve shown there) is less than in at least one of the regions (I and III) of the graph adjacent to the "plateau" region. The "plateau" region, typically, extends over the greater part of the spring element's extension range contemplated to be used in a compression procedure. The broken line in FIG. 14B allows for better visualization of the changes in the slope of the force-extension curves.

The present invention has been described above as using stress-induced shape changes in spring elements 110. The hysteresis loop for such a situation is represented by curves A-B. The present invention also contemplates using shape changes induced by cooling and stress. A hysteresis loop, shown as curves C-B and having a similar "plateau" region in curve B, reflects the situation when such conditions are employed. Arrows on the hysteresis loops of FIGS. 14A and 14B show the direction in which the stress is applied and removed under each method of martensitic transformation.

It will be appreciated by persons skilled in the art, that in general, a compression assembly employing a spring, spring elements 110 in the present invention, constructed of a shape memory (SM) alloy may be used in one of two ways. The alloy may be deformed at room temperature in its austenite state thus transforming it into its martensite state, often known as stress-induced martensite (SIM) (curve A). This employs the alloy's superelastic behavior. While in its SIM state, the spring's SM alloy is restrained in its deformed shape by a restraining means. After positioning the compression assembly in the body and increasing the spring element's temperature to body temperature and removing the restraining means, the alloy returns to its austenite state and the spring to its original shape along a path represented by curve B. As the spring returns to its uncompressed configuration, it presses on the tissue with a relatively slowly decreasing force, i.e. small dF/dx ratio, over the greater part of its extension range thereby bringing about anastomosis.

In the second way of using a spring constructed from a shape memory (SM) alloy, the superelastic plasticity behavior of the alloy is employed. The alloy of the spring is first cooled transforming the alloy, at least partially, into its martensite state (curve C). The alloy is then deformed, i.e. the spring is then loaded, and retained using a special restraining means in its deformed martensite state. This martensite state is often referred to as the stress-retained martensite (SRM) state. The alloy/spring is then warmed to body temperature. When the spring, in the present invention spring elements 110, is released from the restraining means at body temperature, the alloy returns to its austenite state, and the spring returns to its original uncompressed shape (via curve B). As the spring returns to its original configuration, it presses on the tissue with a relatively slowly decreasing force, i.e. small dF/dx ratio, over the greater part of its extension range thereby bringing about anastomosis.

It should be noted that in both cases, the return to the austenite uncompressed, unloaded state from the compressed, loaded martensite state is along the same path, curve B. In both cases, the same slowly decreasing force, i.e. small dF/dx ratio, represented by the "plateau-like" region of curve B, is recovered.

FIGS. 14A and 14B show that a slowly decreasing force ("plateau-like" region II in curve B) is used in the present invention to bring about anastomosis. In prior art, on the other hand, any spring element used is constructed of regular, non-shape memory materials. Therefore, the force applied by these spring elements is in direct relation to displacement i.e. Hooke's law. Additionally, the maximum reversible strain of spring elements made from conventional metals is on the order of about 0.3%.

In view of the direct relationship to displacement in conventional spring materials, the compressive force to effect anastomosis is a function of tissue thickness. Additionally, in view of the small reversible strain, a large "gap", that is distance between the first and second portions of the CAR assembly, would be required to provide the necessary compressive force.

As already noted, the first factor, in effect, makes the anastomosis process using prior art devices a function of tissue thickness. However, in order to get good anastomosis with a strong seal at the join, approximately the same force should be applied throughout the process, and the force should be essentially the same irrespective of tissue thickness. It should be noted that too much force may lead to premature detachment of the CAR assembly, possibly even before healthy new scar tissue is formed. Too little force may result in the CAR assembly detaching only after a very long time. Additionally, it may not produce ischemia. Spring elements formed from shape-memory alloys, as in the present invention, provide a relatively slowly decreasing force independent of tissue thickness, in their "plateau-like" region without premature or excessively long detachment times. They also produce ischemia as required.

As also noted above, the second factor discussed above, that is the small reversible strain of regular spring materials, requires an increased size for the CAR assembly. The resulting increase in assembly size would inter alia impair the assembly's expulsion from the bowel after anastomosis has been completed.

The use of a shape memory alloy, typically nitinol, for forming a spring element, as in the present invention, allows for the use of a thin nitinol leaf as a spring element. The leaf, typically, but without intending to be limiting, may have a thickness of about 0.5 mm. When the leaf deforms, the CAR "gap", the distance between the first and second portions of the CAR assembly, increases. What is herein described as being a small leaf spring allows for the use of nitinol's relatively large reversible strain (~6%) as contrasted with a conventional metal's small reversible strain (~0.3%). With conventional spring metals similar deformations can not be achieved; a physically larger spring such as a coil spring must be used. This would lead to larger assembly sizes.

It therefore was realized by the inventors that a resilient element, here at least one spring element, formed from a shape memory material, such as nitinol, would maximize the efficiency of the element in speeding healing. In effect, use of shape memory materials allows for maximizing healing by taking into consideration the needs of the healing and necrotic processes as tissue thickness decreases during the processes.

At the far end of the X axis on the force-extension curves of FIGS. 14A and 14B, i.e. at the beginning of the compression/healing/necrotic process where tissue thickness (X) is greatest, nitinol elements allow for faster hemostasis by providing their greatest force in region III shown in FIG. 14B. As is generally known, greater pressure assists in hemostasis.

As healing continues and tissue thickness is reduced a relatively slowly decreasing force, regardless of tissue thickness (X), is more beneficial (region II shown in FIG. 14B). This is more advantageous because a slowly decreasing force as thickness (X) decreases, allows for a better seal between the tissues being compressed and joined. There is less chance for leakage and sepsis.

A usable figure of merit for determining the suitability of a material in forming the resilient elements, here spring elements, required in constructing the compression assemblies of the present invention would be $F_b/F_a \leq 2$ where F is the force generated by the spring element constructed of the given material at the high force end (point b) of region II and the low force end (point a) of region II ("plateau-like" region).

In FIG. 14B, the high force end of region II is represented by the force at point 3 and the low force end of region II by point 2.

Finally, at the end stage of the healing process, i.e. the necrotic phase, where tissue thickness X is smallest, a relatively controlled detachment of the compression assembly is required. The force drops to zero as tissue thickness (X) drops to zero (region I of FIG. 14B). This prevents the compression assembly from detaching before necrosis is complete. The compression assembly would tear through the thin tissue if the force did not decrease to zero, and detachment would otherwise occur before healing was complete.

The material from which the resilient elements, here the spring elements, of the present invention have been formed has been discussed in terms of shape memory alloys. It should be understood that the present invention also contemplates other materials which do not behave according to Hooke's law and which provide a relatively slowly decreasing force over a substantial portion of the spring element's expected range of extension as in FIGS. 14A and 14B. Therefore, dF/dx should be small over a substantial portion of the expected extension range; alternatively the Young's modulus of the material should be smaller over a substantial portion of the expected extension range than the adjacent portions of the graph.

It will be understood by a person skilled in the art that all materials having characteristics similar to those discussed above for Ni—Ti alloys and spring elements made from such alloys, may be used to form the resilient elements, here the spring elements, used in compression assemblies constructed according to the present invention. The use and discussion above of shape memory materials is not intended to limit the choice of materials that may be used for such resilient elements.

It will be appreciated by persons skilled in the art that there is a direct relationship between the size and thickness of the CAR assembly 100 and applicator 10 used in the surgical procedure disclosed above and the size, shape and type of organ to be treated. A CAR assembly 100 of a particular size is selected so as to achieve an aperture of a requisite size as appropriate to the situation and the hollow organ to be subjected to anastomosis. Clearly, a smaller size is appropriate for use in the upper bowel and a larger size in the lower bowel.

It should also be understood that the present invention also contemplates a case where spring elements 110 may be deployed in their unloaded, uncompressed, here arched, configuration. In such a configuration, the alloy from which the spring elements are formed is initially in its austenite state. After the second portion 101 of CAR assembly 100 is deployed (with its spring elements 110 in their unloaded austenite state) on the distal end of CAR applicator 10, a load can be applied to CAR flange 108. Such a load can be applied by a load lip, load teeth or load protrusions. After bringing spring elements 110 to their loaded martensite state, anvil disk 103 of the CAR assembly 100 is brought towards the second portion 101 of CAR assembly 100 with tissue to be anastomosized held therebetween. When the tissue is held sufficiently securely by anvil disk 103 and second portion 101, spring elements 110 are unloaded and they begin to arch causing bottom ring 104 of CAR assembly 100 to compress the tissue held against anvil disk 103 and anastomosis can occur. In this embodiment, as in prior embodiments, spring elements 110 may be positioned on CAR flange 108 and in contact with bottom ring 104. Alternatively, when no CAR flange is present spring elements 110 may be positioned on needle ring 106 so that it is in contact with bottom ring 104.

As noted previously, all ring or ring-shaped elements discussed herein with respect to the CAR assembly 100, contemplate, in addition to the use of circular-shaped elements, the possibility of using elliptical, ovoid or other shaped elements. The use of "ring" should not be deemed as shape limiting for the ring elements described and illustrated hereinabove. These ring elements include, but are not limited to, the needle ring, the CAR flange, and the bottom ring. Among the other shapes contemplated for use with elements of the present invention are hexagonal, octagonal and other closed curve shapes. Additionally, substantially linear elements may also be used. Assemblies including linear elements are not necessarily contemplated for use in anastomosis procedures but may be used in compression closure of resections, excisions, perforations and the like.

It should also be borne in mind that the applicator discussed herein with assembly 100 is only exemplary and not intended to be limiting. Other applicators may also be designed by persons skilled in the art that may be used with CAR assembly 100.

FIGS. 15-20, to which reference is now made, illustrate a linear compression assembly constructed according to an embodiment of the present invention.

Figure 15:
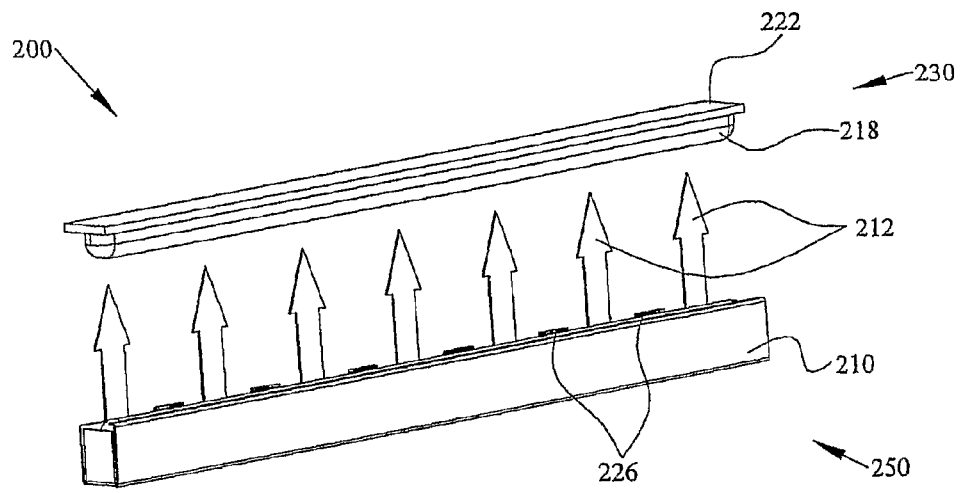
FIG. 15 shows a schematic isometric view of a linear CAR assembly in its open configuration, the assembly constructed according to an embodiment of the present invention.
Figure 16:
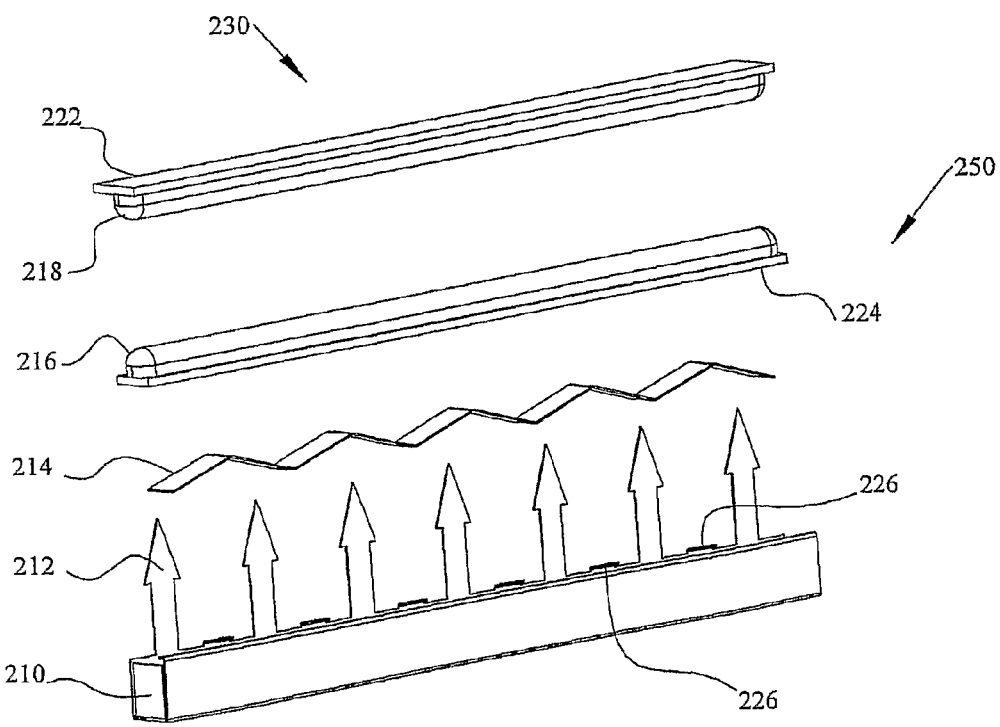
FIG. 16 shows a substantially exploded view of the assembly shown in FIG. 15.
Figure 17:
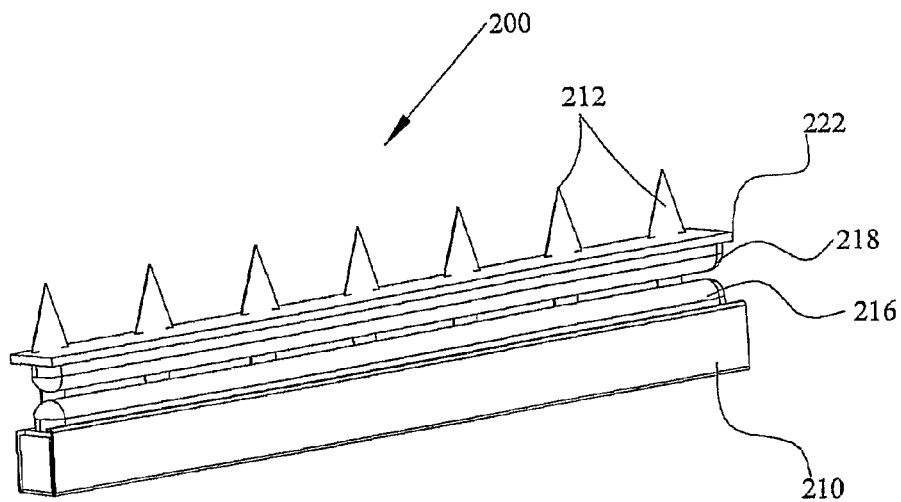
FIGS. 17 and 18 show schematic isometric views of the assembly of FIG. 15 in its substantially closed configuration with FIG. 18 showing a partially cut-away view of this configuration.

FIG. 15 shows a linear compression assembly 200 in its open configuration while FIG. 16 shows an exploded view of linear compression assembly 200. Linear compression assembly 200 includes an upper element 230 formed, at least partially, of any of a large number of rigid plastics known to those skilled in the art and a lower element 250 which may be formed from any of a large number of plastics or metals known to those skilled in the art. Upper element 230 is formed to be comprised of a compression element 218 affixed to an upper element support 222. Compression element 218 may be made of any of a number of rigid plastics or metals while support 222 is formed of any of a number of rigid plastics. Upper element 230 may include holes into which the ends of needles 212, to be discussed below, may enter. Alternatively, no such holes need be included and needles 212 themselves pierce and enter plastic upper element support 222 when a force of sufficient magnitude is exerted on them.

Lower element 250 is comprised of a needle support 210, one or more spring elements 214 (in FIGS. 15-20, a single spring element) and a compression element 216 affixed to lower element support 224. In FIGS. 15 and 16, the single spring element has an elongated rippled shape and is positioned substantially on the floor of U-shape needle support 210. Needle support 210 includes a plurality of barbed needles 212, each needle 212, typically but without intending to limit other possibilities, spaced substantially equidistant from its nearest neighbors. Needles 212 are deployed in essentially a linear configuration to conform to the linearity of needle support 210. The needle configuration shown in FIGS. 15-20 is exemplary only and not intended to be limiting. In some embodiments, needles 212 will extend from both long lateral walls of needle support 210 along the entire length of these walls.

Lower element support 224, upon which is affixed compression element 216, is positioned above spring element 214. Compression element 216 may be made of any of a number of rigid plastics or metals while support 224 is formed of any of a number of rigid plastics or metals. The positioning of the constituent elements of lower element 250 is illustrated in FIGS. 17-20, to which the reader is directed. Lower element support 224 upon which is affixed compression element 216 is held within needle support 210 by a plurality of securing catches 226 best seen in FIGS. 15, 16 and 20. The sides of needle support 210 perpendicular to its long axis may be open or closed. The positioning of needles 212, while shown in FIGS. 15-20, is best presented in FIG. 20.

Needles 212 may be formed integrally with needle support 210. Alternatively, they may be joined to needle support 210 by any of several methods known to those skilled in the art, such as welding, gluing, and pressure fitting with the method of joining depending upon the materials from which needles 212 and needle support 210 are constructed. These methods are exemplary only and are not intended to be limiting. The shape of the barbs on the heads of needles 212 as shown in FIGS. 15 and 16 is exemplary only. Any generally penetrating shape may be used as the head of needles 212, even sharp heads without barbs.

Figure 18:
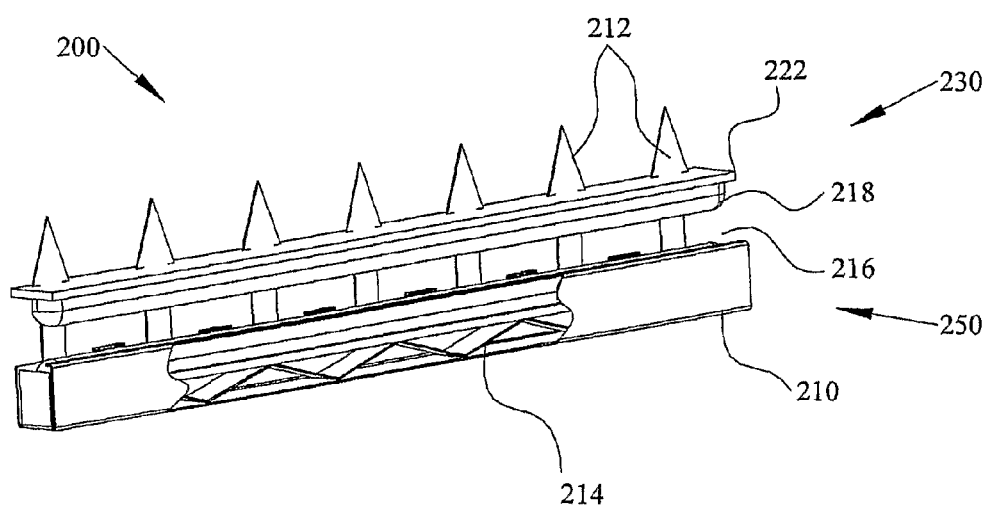
Figure 19:
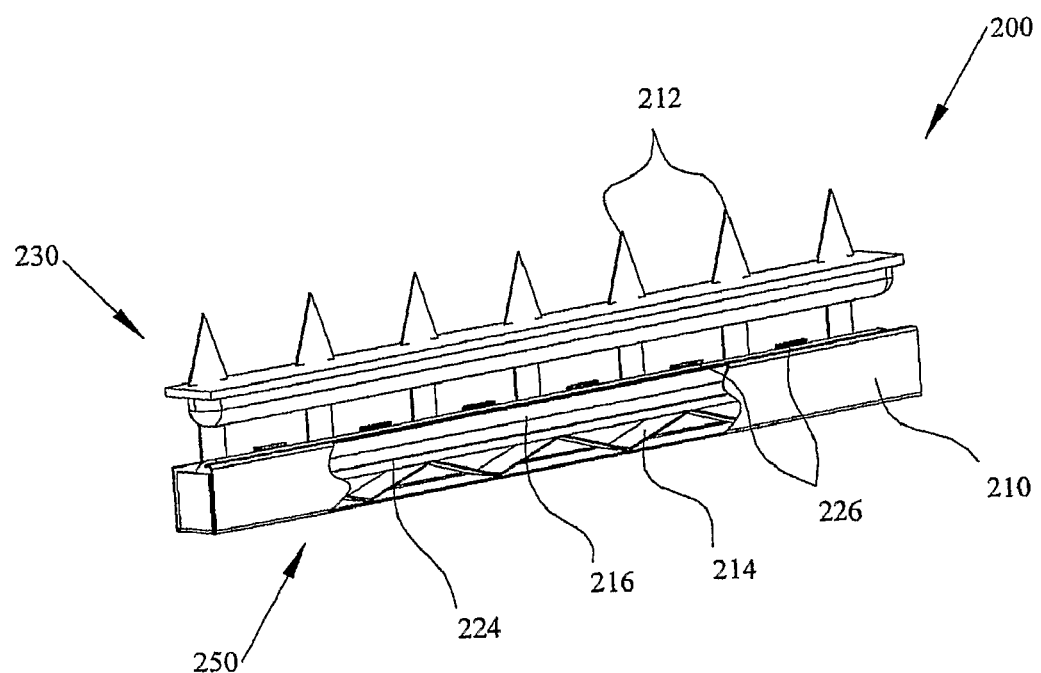
FIG. 19 shows another schematic isometric partially cut-away view of the assembly of FIG. 15 while moving to the substantially closed configuration of FIGS. 17 and 18.
Figure 20:
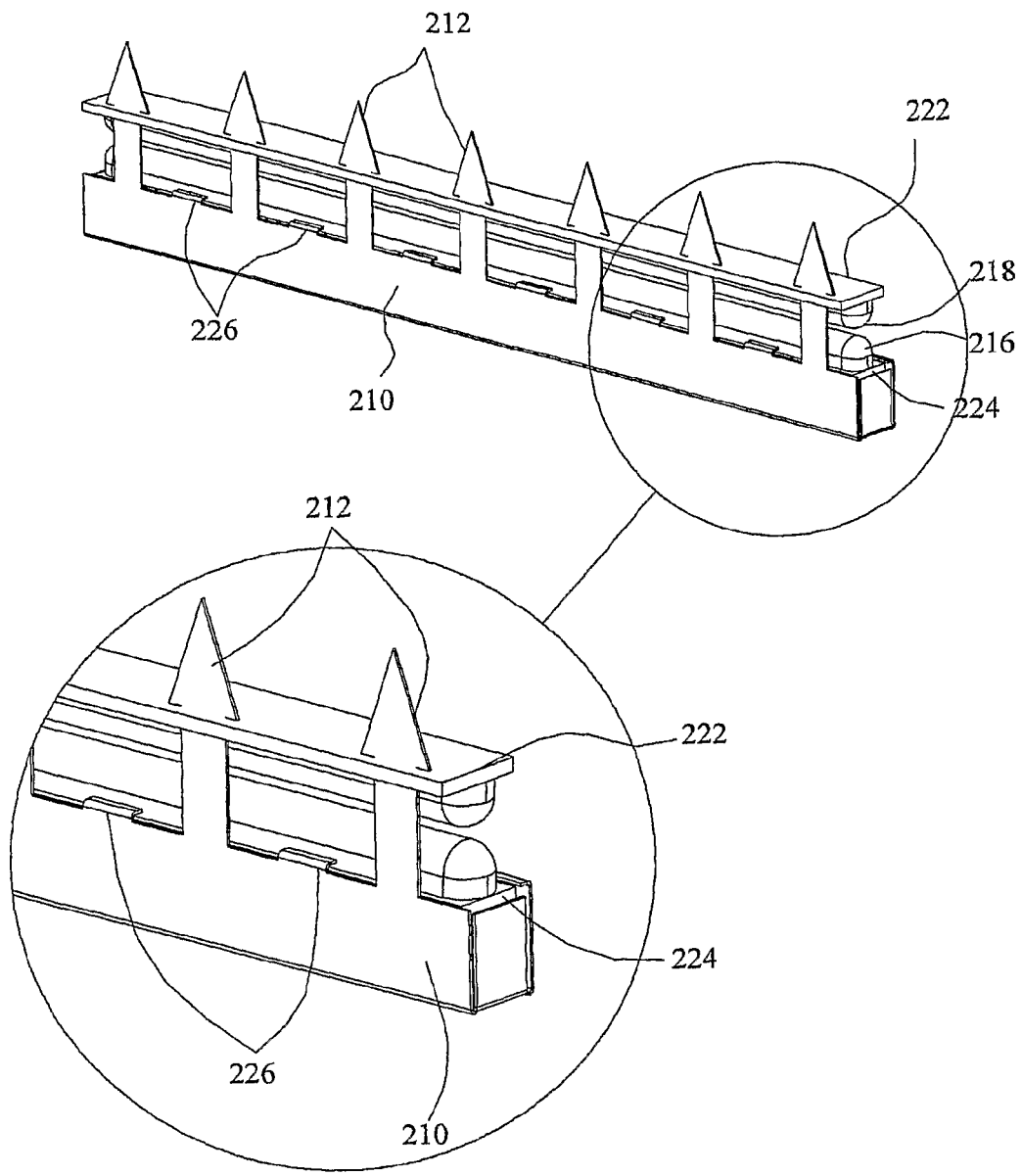
FIG. 20 shows a schematic isometric view of the assembly of FIG. 15 in its substantially closed configuration from the side where the needles are proximate to the viewer.

Needle support 210 and the plurality of barbed needles 212 are typically, but without intending to be limiting, formed from any of a large number of metals or plastics known to those skilled in the art. The one or more spring element 214 is made from a shape-memory material, typically, but again without intending to be limiting, Ni—Ti alloy. Also typically, but without intending to be limiting, spring element 214, when in its unloaded austenite state, typically has a rippled shape. Spring element 214 is positioned to lie within and generally on the floor of hollow U-shaped needle support 210. The top of rippled spring element 214 contacts the adjacent side of lower element support 224. When the shape-memory material from which spring element 214 is formed is in its loaded state, spring element 214 lies in a flatter, but still rippled, configuration within needle support 210. Spring element 214 is positioned within needle support 210 so that its ends can move when going from the spring element's compressed rippled shape to the spring elements' flatter uncompressed but still rippled shape and vice versa. FIGS. 18 and 19 illustrate the effects the shape of spring element 214 has on the compression exerted by it on lower element support 224 and compression element 216.

Spring element 214 has been described herein as having a flatter but still rippled configuration (FIG. 19) when not exerting compression and a more rippled configuration when exerting compression (FIG. 18) on compression element 216. The present invention also contemplates other possible spring forms and configurations, including conventional coiled configurations.

Spring element 214 is movable on needle support 210 and it is capable of moving from its compressed to uncompressed configurations/shapes and vice versa. Spring element 214 is typically, but without intending to be limiting, deployed in its non-compressed austenitic state.

The discussion above, in conjunction with FIGS. 14A and 14B, relating to the characteristics of spring elements formed of shape memory alloys is valid, mutatis mutandis, with respect to the shape memory elements in the linear compression assembly 200.

It should be noted that the use of the terms "bottom", "lower", and "upper" herein as descriptors for various elements in the linear compression assembly 200 should not be deemed as denoting anything about the specific spatial and functional relationship between these elements. The spatial and functional relationship of the elements of assembly 200 (and between the elements and the tissue being compressed) are defined by the description and the drawings. Additionally, in other places in this specification and claims the following elements of linear compression assembly 200 may be referred to in other terms: upper element 230 as first portion, lower element 250 as second portion, needle support 210 may be referred to as needle bearing support, compression element 218 as a first compression element, and compression element 216 as a second compression element. Other elements in assembly 200 may similarly have different, but essentially equivalent, terminology.

Linear compression assembly 200 described above may be used, typically, but without being limiting, to effect compression closure of resected or excised tissues and naturally occurring or surgically produced perforations. In other embodiments, linear compression assembly 200, with some modification, may be used to effect anastomosis.

The mode of operation of linear compression assembly 200 shown in FIGS. 15-20 is as follows. Assembly 200 is joined to an applicator (not shown) one member of which attaches to lower element 250 while another member attaches to upper element 230. The applicator delivers these elements to the tissue site requiring compression.

The applicator and assembly are typically, but without intending to be limiting, delivered via a secondary lumen of a multi-lumen sleeve. The sleeve's primary lumen encases an endoscope. The applicator and assembly may also be introduced using rigid tools in an open or laparoscopic surgical procedure.

In another secondary lumen of the sleeve, a grasper assembly is advanced to the site requiring compression. The grasper assembly grasps the tissue to be compressed bringing it between the upper 230 and lower 250 elements of linear compression assembly 200 that have already been positioned near the site.

The specific construction of the applicator can be one of many and varied depending on, among other things, the required mode of attachment to upper 230 and lower 250 elements of linear compression assembly 200.

With the tissue to be compressed still grasped and held between upper 230 and lower 250 elements of assembly 200, the applicator moves the upper element toward the lower element and the tissue held therebetween. Alternatively, the applicator may be constructed to move the lower element toward the upper element with the tissue held therebetween. Alternatively, the applicator may be constructed to move both the upper and lower elements toward each other with the tissue held therebetween.

When the upper 230 and lower 250 elements are sufficiently close to each other, needles 212 first pierce the tissue and then the upper element support 222 resulting in the joining of upper 230 and lower 250 elements. The spacing between the elements should be such that the tissue is securely held and firmly compressed between upper compression element 218 and lower compression element 216.

It should be noted that the side of the closed linear compression assembly with the needles should be oriented distally from the organ wall of the tissue to be compressed. This allows for compression elements 216 and 218 to be closer to the organ wall than needles 212, thereby better able to prevent leakage of fluids during the process of compression, necrosis and healing.

After the tissue is held by needles 212 and compressing elements 216 and 218 begin compressing the tissue, the grasper assembly and the applicator are withdrawn through the secondary lumens of the multi-lumen sleeve through which they were inserted.

If required, resection can be effected at this stage by introducing a severing device into a secondary lumen of the sleeve, or through the endoscope's working channel; the severing device is then advanced to the tissue being compressed. When the severing device reaches the compressed tissue, severing of the tissue occurs on the side of the needle support 210 proximal to needles 212. After severing is completed the severing device may be withdrawn through the secondary lumen through which it was advanced.

After compression is effected so that necrosis and then healing of the region around the necrosed tissue occurs, the clip is evacuated naturally through a body orifice.

Figure 21:
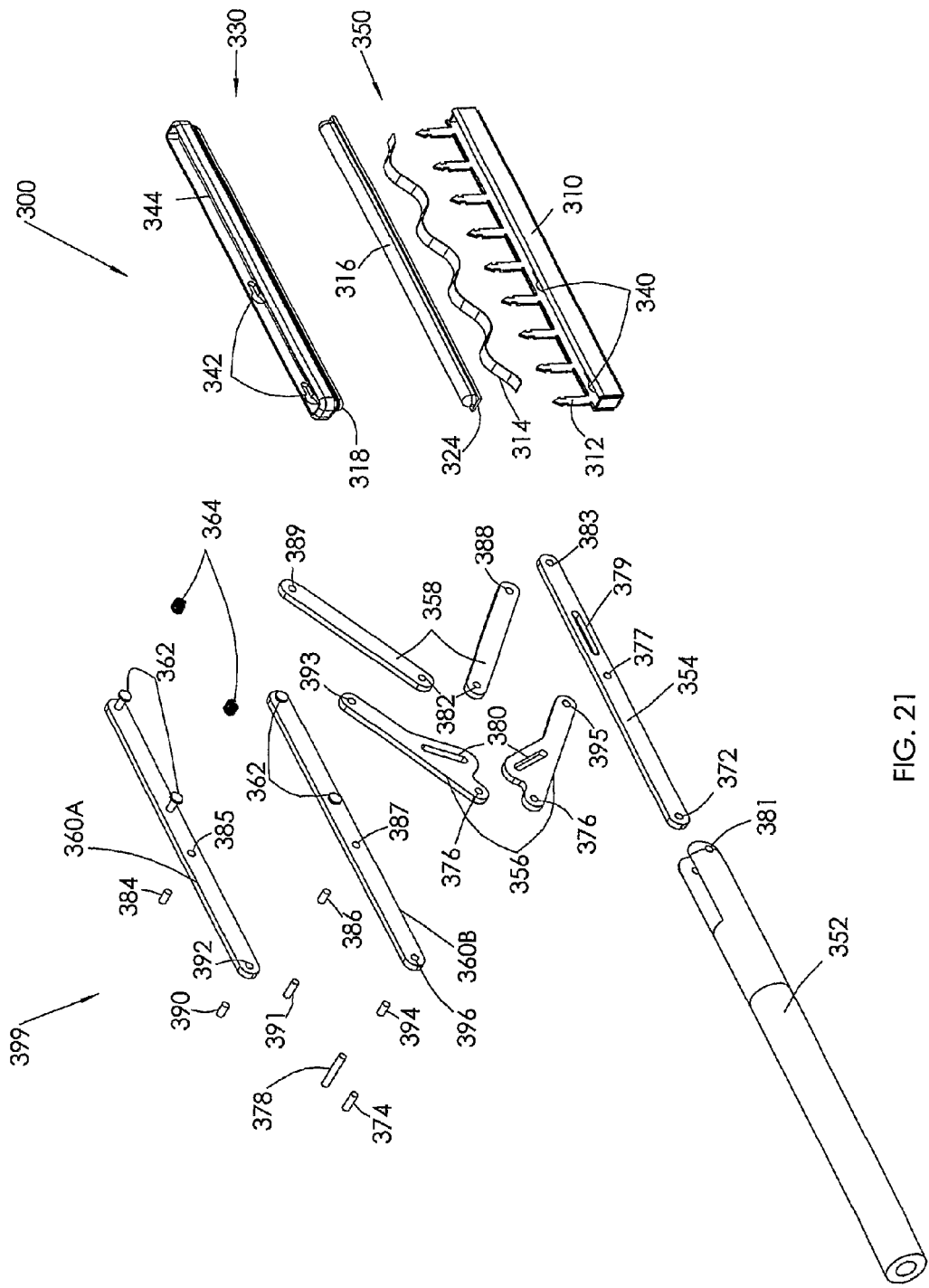
FIG. 21 shows an exploded view of a linear compression assembly constructed according to an embodiment of the present invention and an exploded view of an exemplary applicator to be used with the linear compression assembly in the Figure.
Figure 23A:
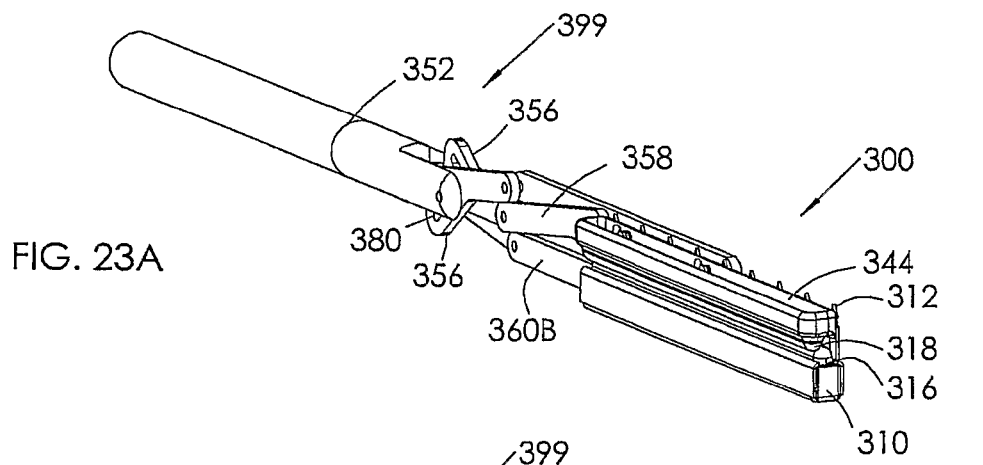
FIG. 23A shows the applicator of FIG. 21 attached to the linear compression assembly with the latter in its closed position and where the assembly is advanced by the applicator to the tissue (not shown) to be compressed.
Figure 23B:
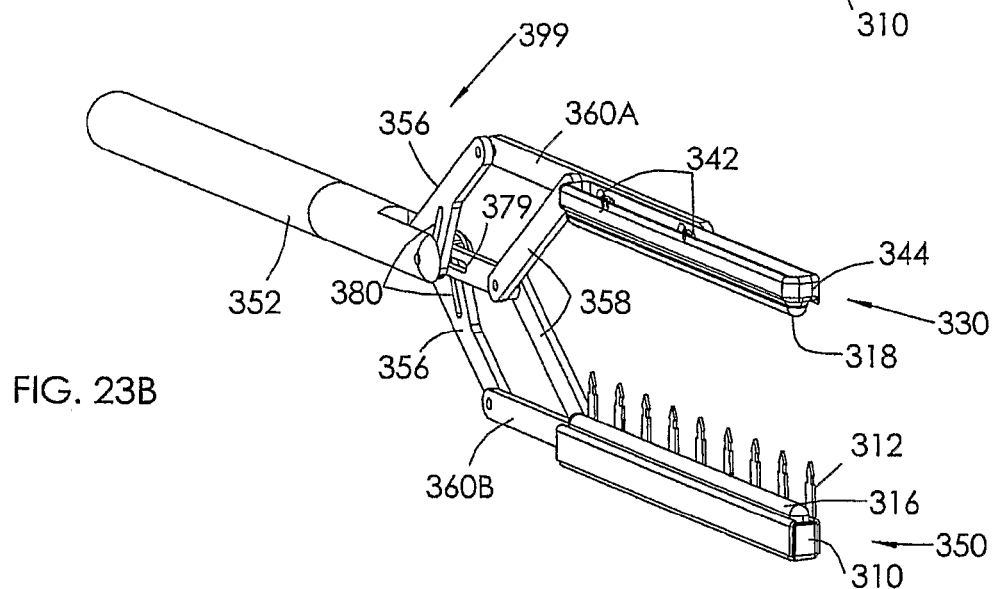
FIG. 23B shows the assembly in its open position and attached to the applicator of FIG. 21.
Figure 23C:
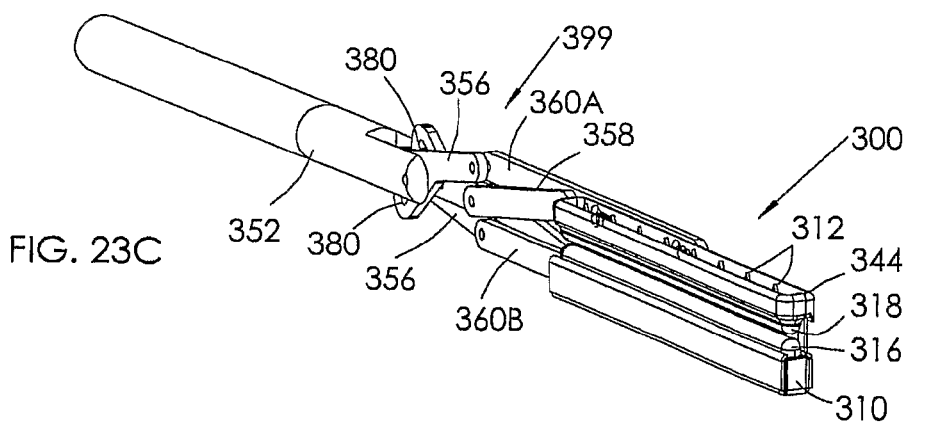
FIG. 23C shows the assembly in its closed position with tissue (not shown) to be compressed held between the assembly's compression elements.
Figure 24A:
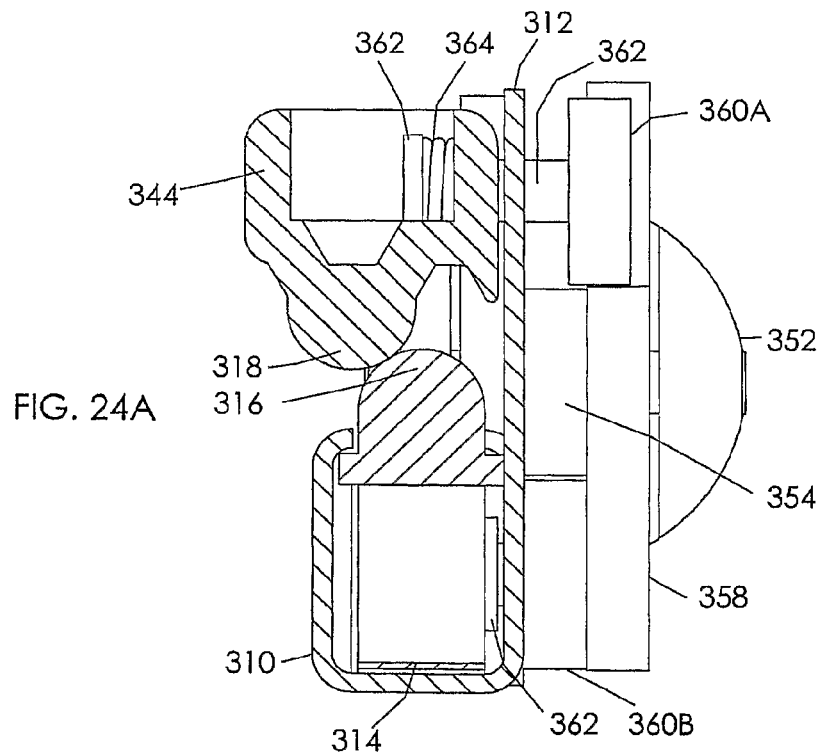
FIGS. 24A-24B show cross-sectional views of the linear compression assembly shown in FIGS. 23A and 23C, respectively.
Figure 24B:
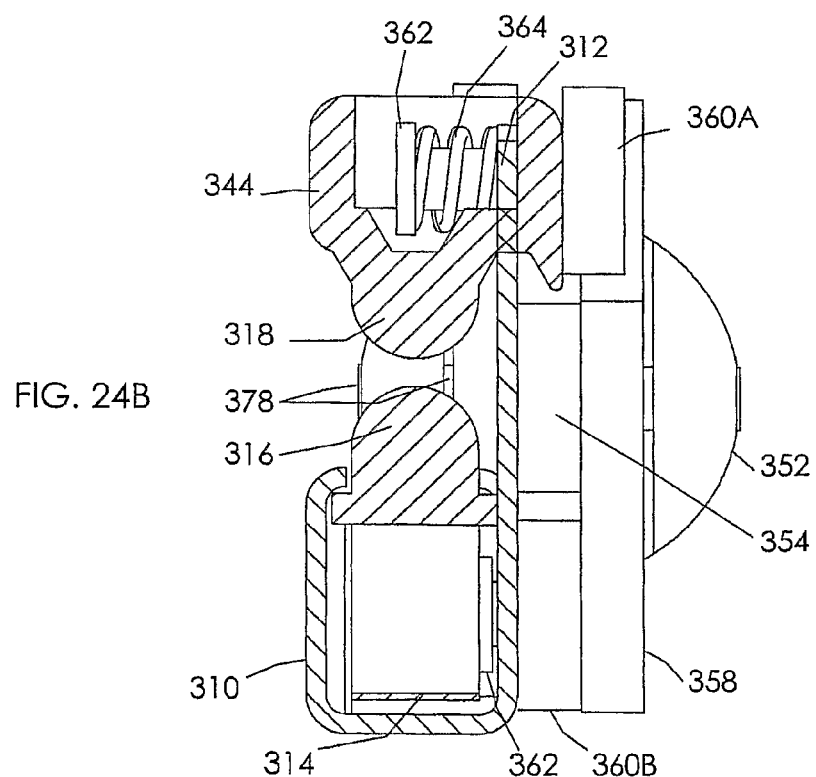

FIGS. 21-24B, to which reference is now made, illustrate a linear compression assembly constructed according to an embodiment of the present invention. In addition, FIGS. 21 and 23A-24B show an applicator which can be used to position the linear compression assembly around tissue to be compressed and joined, including, but not limited to, tissue around a resected gastrointestinal polyp. FIG. 21 shows exploded views of a linear compression assembly and an exploded view of a non-limiting example applicator for use with the assembly. FIGS. 22A-22E show various views of the linear compression assembly beginning with a view of separated upper and lower elements of the assembly (FIG. 22A); two views including a partial cut-away view of the assembly as it holds tissue (not shown) between its upper and lower elements (FIGS. 22B-22C); and two views including a partial cut-away view of the assembly as its upper and lower elements are moved together and closed around tissue (not shown) to be compressed (FIGS. 22D-22E). FIG. 23A shows the linear compression assembly attached to the applicator shown in FIG. 21 as it is advanced toward tissue (not shown) to be compressed; FIG. 23B shows the compression assembly being opened by the applicator after it is brought adjacent to the tissue to be compressed with the tissue (not shown) brought between the upper and lower elements of the assembly by a second instrument (also not shown); and FIG. 23C shows the linear compression assembly closed around the tissue (not shown) to be compressed by the assembly. FIGS. 24A and 24B show cross-sectional views of the linear compression assembly attached to the applicator as it is brought to the tissue to be compressed and as it is compressing the tissue (not shown) between the assembly's upper and lower elements.

The linear compression assembly 300 shown in FIGS. 21-24B is very similar to linear compression assembly 200 discussed in conjunction with FIGS. 15-20. Elements found both in assembly 200 and assembly 300 having similar construction and operation are numbered similarly with a first digit of "3" in assembly 300 replacing a first digit of "2" in assembly 200. Only elements in assembly 300 not found in assembly 200 will be discussed below.

Upper element 330 in addition to being comprised of an upper element support (not shown but best seen in FIGS. 16-18 as element 222) to which compression element 318 is affixed also contains an upper element casing 344 into which upper element support (not shown) and compression element 318 are positioned. Upper element casing 344 is formed, typically, of rigid plastic or metal, so as to contain attachment apertures 342 in one of its lateral walls i.e. the walls parallel to the upper element's long axis.

Needle bearing support 310 is also formed so as to contain attachment apertures 340 in one of its lateral walls, i.e. the walls parallel to the upper element's long axis.

Attachment apertures 340 and 342, positioned on needle support 310 and upper element casing 344, respectively, are sized and configured to receive attachment projections 362 on attachment arms 360A and 360B of applicator 399 (see discussion below).

Attachment apertures 340 and 342 are shown here as having keyhole shapes for ease of applicator engagement and disengagement. These, however, are exemplary shapes only; any other aperture configuration which allows for easy engagement and disengagement of the applicator's attachment projections (discussed below) may be used.

In the embodiment of FIGS. 21-24B, needle structures 312 are wider at their ends distal from the barb, and proximal to needle bearing support 310. This wider end acts as a stop when the needle structure pierces the tissue and then upper element 330. This mechanism prevents unnecessary crushing and damage to the tissue prior to complete joining and healing of the tissue during compression.

FIGS. 21 and 23A-23C, to which reference is now made, will be discussed together. FIG. 21 shows an exploded view of a typical, but non-limiting, example of an applicator 399 to be used with a linear compression assembly 300, such as the assembly in FIG. 21. FIGS. 23A-23C show applicator 399 attached to linear compression assembly 300 and advancing it to tissue (not shown) to be compressed (FIG. 23A), bringing assembly 300 to its open configuration so as to allow for positioning of tissue (not shown) to be compressed between compression elements 316 and 318 of assembly 300 (FIG. 23B) and then closing upper 330 and lower 350 elements of assembly 300 around the tissue (not shown) to be compressed (FIG. 23C).

In the exploded view of FIG. 21, applicator 399 is shown to include a cable casing 352 through which an operating cable (not shown) passes and which is attached to aperture 372 of control rod 354. Control rod 354 is in mechanical communication with two control links 356 via a pin 374 passing through aperture 377 on control rod 354 and through apertures 376 on control links 356. A pin 378 passes through aperture 381 on cable casing 352 and is concurrently slidable within control link slots 380 and control rod slot 379.

Control rod 354 is in mechanical connection via pin 391 with two connector links 358 via apertures 382 on the latter and aperture 383 on the former.

Attachment arm 360A is in mechanical communication with one of connector links 358 via pin 384 which passes through aperture 385 on attachment arm 360A and aperture 389 on the connector link 358. Attachment arm 360B is in mechanical communication with the other connector link 358 via pin 386 which passes through aperture 387 on attachment arm 360B and aperture 388 on the other connector link 358.

Attachment arm 360A is in mechanical communication with one of control links 356 via pin 390 which passes through aperture 392 on attachment arm 360A and aperture 393 on one of control links 356. Attachment arm 360B is in mechanical communication with the other control link 356 via pin 394 which passes through aperture 396 on attachment arm 360B and aperture 395 on the other control link 356.

Attachment arms 360A and 360B also include attachment projections 362 for engagement with attachment apertures 340 and 342 formed in needle bearing support 310 and upper element casing 344, respectively, of linear compression assembly 300. Projections 362 are also easily disengageable from apertures 340 and 342 once positioning and closing of the linear compression assembly 300 around the tissue to be compressed is effected.

Positioned on attachment projections 362 on attachment arm 360A are springs 364. As explained below in conjunction with FIGS. 24A and 24B, these springs are used to align upper and lower elements of assembly 300 vis-a-vis each other when the assembly is brought to its open configuration. Upper and lower elements are offset from each other when in their closed configuration such as when linear compression assembly 300 is advanced toward the tissue to be compressed.

Turning to FIG. 23A we see a closed linear compression assembly 300 attached to applicator 399 advancing to tissue (not shown) to be compressed. Upper 330 and lower 350 elements of assembly 300 when closed are held adjacent to each other. When closed for advancement towards the tissue to be compressed, elements 316 and 318 are slightly displaced from each other as will be seen more clearly below in FIG. 24A. The displacement ensures that there is no premature mechanical connection, i.e. penetration of needles 312 into the upper element support (not shown). This allows assembly 300 to be brought to its open configuration, i.e. upper and lower elements spaced apart from each other, once it has been brought close to the tissue to be compressed.

When linear compression assembly 300 is closed an operating cable (not shown) has maneuvered control rod 354 so that pin 378 is positioned at the end of slot 379 proximal to linear compression assembly 300. Similarly, pin 378 is positioned in slots 380 of control links 356 in a position proximal to assembly 300.

In FIG. 23B, linear compression assembly 300 is brought to its open configuration with the lower and upper elements spaced apart waiting for the introduction of tissue to be compressed between them. To bring the compression assembly to its open configuration, the operating cable (not shown) in cable casing 352 is pushed forward so that control rod 354 moves forward in a direction proximal to assembly 300. As a result, slot 379 moves forward over pin 378. At the end of the latter movement, pin 378 is located at the end of slot 379 distal from linear compression assembly 300. As control rod 354 is moved forward in a direction proximate to assembly 300, pin 374 moves forward thus forcing apertures 376 of control links 356 to move forward. Since control links 356 are fixed to cable casing 352 by pin 378 passing through slots 380, the only way for aperture 376 to move forward is by rotating around pin 378. This causes control links 356 and connector links 358 to rotate and move apart as shown when going from FIGS. 23A to 23B reaching their open configuration.

Turning to FIG. 23C, compression assembly 300 is closed around tissue (not shown) positioned between upper 330 and lower 350 elements of assembly 300. To close the assembly, the operating cable (not shown) connected to aperture 372 in control rod 354 is pulled back resulting in control rod 354 moving away, that is distally, from assembly 300. Slot 379 in rod 354 slides back over pin 378 so at the end of the movement pin 378 is located at the end of slot 379 proximal to linear compression assembly 300. As control rod 354 is moved in a direction distal from assembly 300, pin 374 moves backward. This forces apertures 376 of control links 356 to move in a direction distal from assembly 300. Since control links 356 are fixed to cable casing 352 by pin 378 passing through slots 380, the only way for aperture 376 to move backward in a direction distal from assembly 300 is by rotating around pin 378. This causes control links 356 and connector links 358 to rotate and move together as shown when going from FIGS. 23B to 23C reaching their closed configuration, compressing the tissue (not shown) held therebetween. When in this closed configuration, needle elements 312 are first forced to pierce the tissue and they then pierce the upper element support (best seen as element 222 in FIGS. 16-18). This holds upper element 330 to the lower element 350 with the tissue (not shown) held therebetween. It also allows the held tissue to be compressed by compression elements 316 and 318. Once mechanical connection between upper and lower elements is achieved, i.e. penetration of the needles into the upper element support, spring element 314 presses on compression element 316 keeping a relatively slowly decreasing force on the compressed tissue (not shown) during the greater part of the joining and healing process.

The mechanical connection, i.e. penetration of the needles into the upper element support, establishes a fixed, pre-determined gap between upper and lower element assembly 300. Spring element 314 then allows for a relatively slowly decreasing compression force to be applied to the compressed tissue during the greater portion of the tissue's healing process. Compression of the tissue is a result of the force applied by spring element 314 to compression element 316. The latter is free to move inside hollow U-shaped needle bearing support 310 towards compression element 318; compression element 318 is fixed relative to needle bearing support 310 by the mechanical connection described above. Utilizing the relatively slowly decreasing stress characteristic of shape memory materials, e.g Ni—Ti alloy, allows for a slowly decreasing force to be applied on the compressed tissue regardless of the decrease in the tissue thickness as it goes through the healing process.

The one or more spring elements 314 is made from a shape-memory material, typically, but again without intending to be limiting, Ni—Ti alloy. Also typically, but without intending to be limiting, spring element 314, when in its unloaded austenite state, typically has a rippled shape. Spring element 314 is positioned to lie within and generally on the floor of hollow U-shaped needle support 310. The top of rippled spring element 314 contacts the adjacent side of lower element support 324. When the shape-memory material from which spring element 314 is formed is in its loaded state, spring element 314 lies in a flatter, but still rippled, configuration within needle support 310. Spring element 314 is positioned within needle support 310 so that its ends can move when going from the spring element's compressed rippled shape to its flatter uncompressed but still rippled shape and vice versa. FIGS. 22C and 22E illustrate the effects the shape of spring element 314 has on the compression exerted by it on lower element support 324 and compression element 316.

Spring element 314 has been described herein as having a flatter but still rippled configuration (FIG. 22E) when not exerting compression and a more rippled configuration when exerting compression (FIG. 22C) on compression element 316. The present invention also contemplates other possible spring forms and configurations, including conventional coiled configurations and multiple spring elements.

As discussed above in conjunction with FIGS. 14A and 14B, the properties of the shape memory material used to form spring element 314 allow for a relatively slowly decreasing force being applied to the compressed tissue during the greater part of the healing process. This allows for better healing and stronger joins than spring elements formed from other materials.

In FIG. 23A, the offset of the upper and lower elements of linear compression assembly 300 is present but difficult to see. In FIG. 23C, where tissue (not shown) is positioned and held between compression elements 318 and 316 of upper 330 and lower 350 elements, respectively, the compression elements are aligned.

The offset and aligned positions are best seen in FIGS. 24A and 24B, respectively. The offset allows for advancing assembly 300 to the tissue to be compressed without needle structures 312 penetrating the upper element support, (not shown here but best seen in FIGS. 16-18 as element 222). This offset can be achieved in many ways, including manually by using the elasticity of the system to force upper element 330 to lean against needle structures 312 as shown in FIG. 24A. The misalignment triggers springs 364 which then apply a force pushing upper element 330 against needles 312 (FIG. 24A). As the compression assembly is brought to its open configuration, upper 330 and lower 350 elements move apart. Once upper element 330 reaches above needles 312, i.e. the needles no longer block the movement of upper element 330, springs 364 push upper element 330 so as to align it with lower element 350. Once upper element 330 is aligned with lower element 350, springs 364 are relaxed and no longer apply a force on upper element 330 (see FIG. 24B). These springs have been discussed previously as being positioned on attachment projections 362 of attachment arm 360A.

Again it should be noted that the use of the terms "bottom", "upper", and "lower" herein as descriptors for various elements in the linear compression assembly 300 should not be deemed as denoting anything about the specific spatial and functional relationship between these elements. The spatial and functional relationship of the elements of assembly 300 (and between the elements and the tissue being compressed) are defined by the description and the drawings. Additionally, in other places in this specification and claims the following elements of linear compression assembly 300 may be referred to in other terms: upper element 330 as first portion, lower element 350 as second portion, needle support 310 may be referred to as needle bearing support, compression element 318 as a first compression element, and compression element 316 as a second compression element. Other elements in assembly 300 may similarly have different, but essentially equivalent, terminology.

It should also be borne in mind that the applicator discussed herein with assembly 300 is only exemplary and not intended to be limiting. Other applicators may also be designed by persons skilled in the art that may be used with linear compression assembly 300.

Figure 25A:
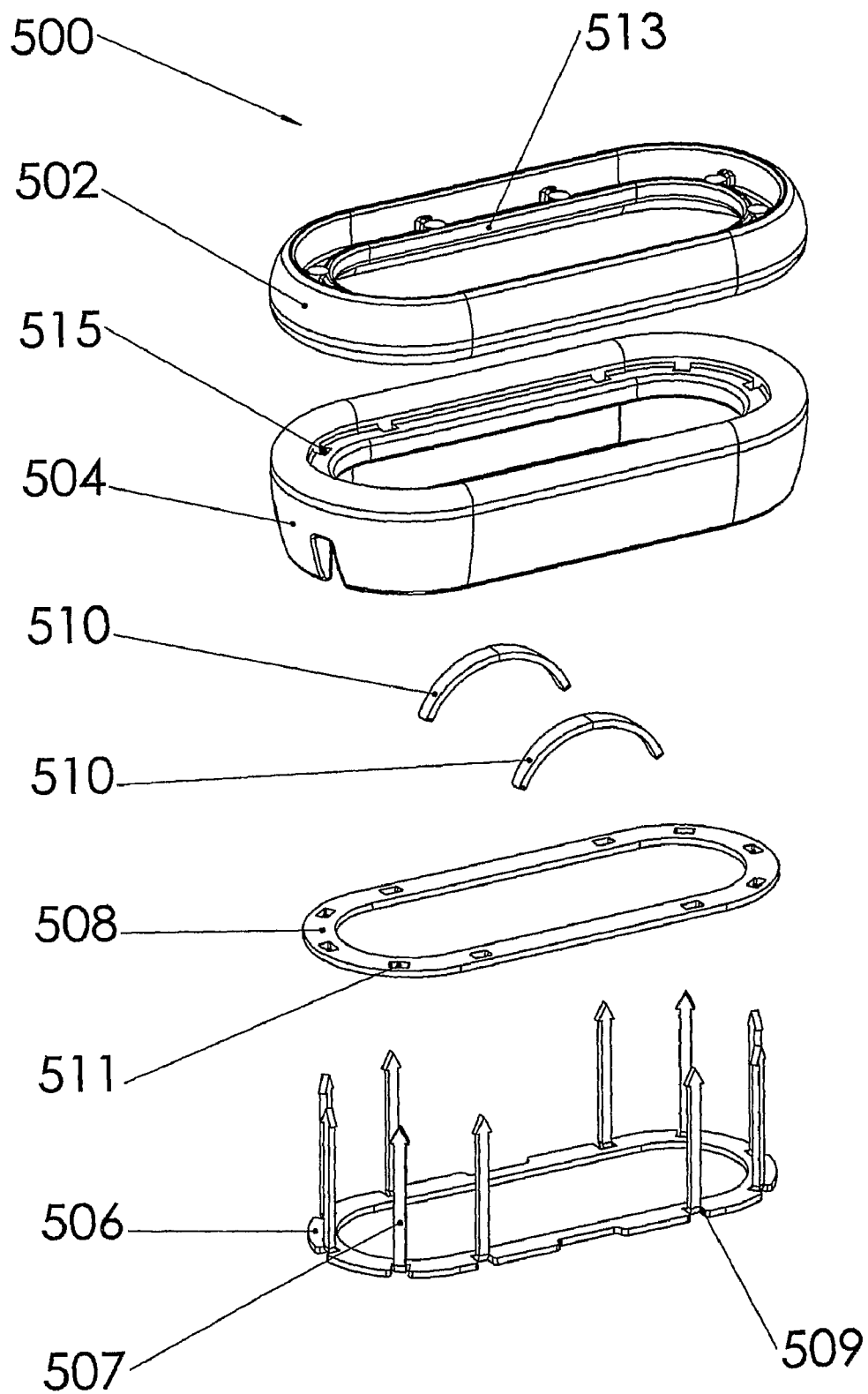
FIG. 25A shows an exploded view of an elliptical compression assembly constructed according to an embodiment of the present invention.
Figure 25B:
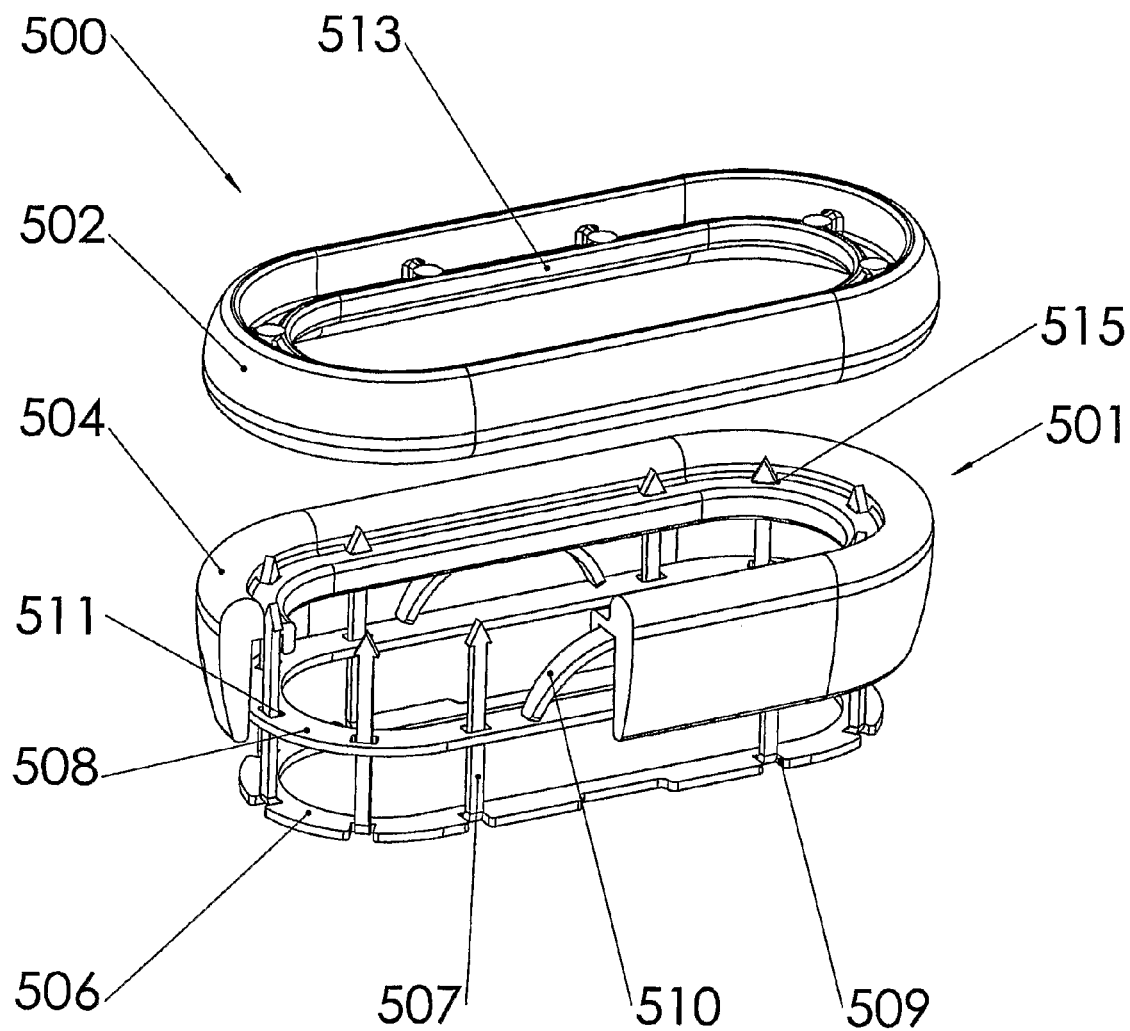
FIGS. 25B-25D show various views of the elliptical compression assembly shown in FIG. 25A in various stages of closure.
Figure 25C:
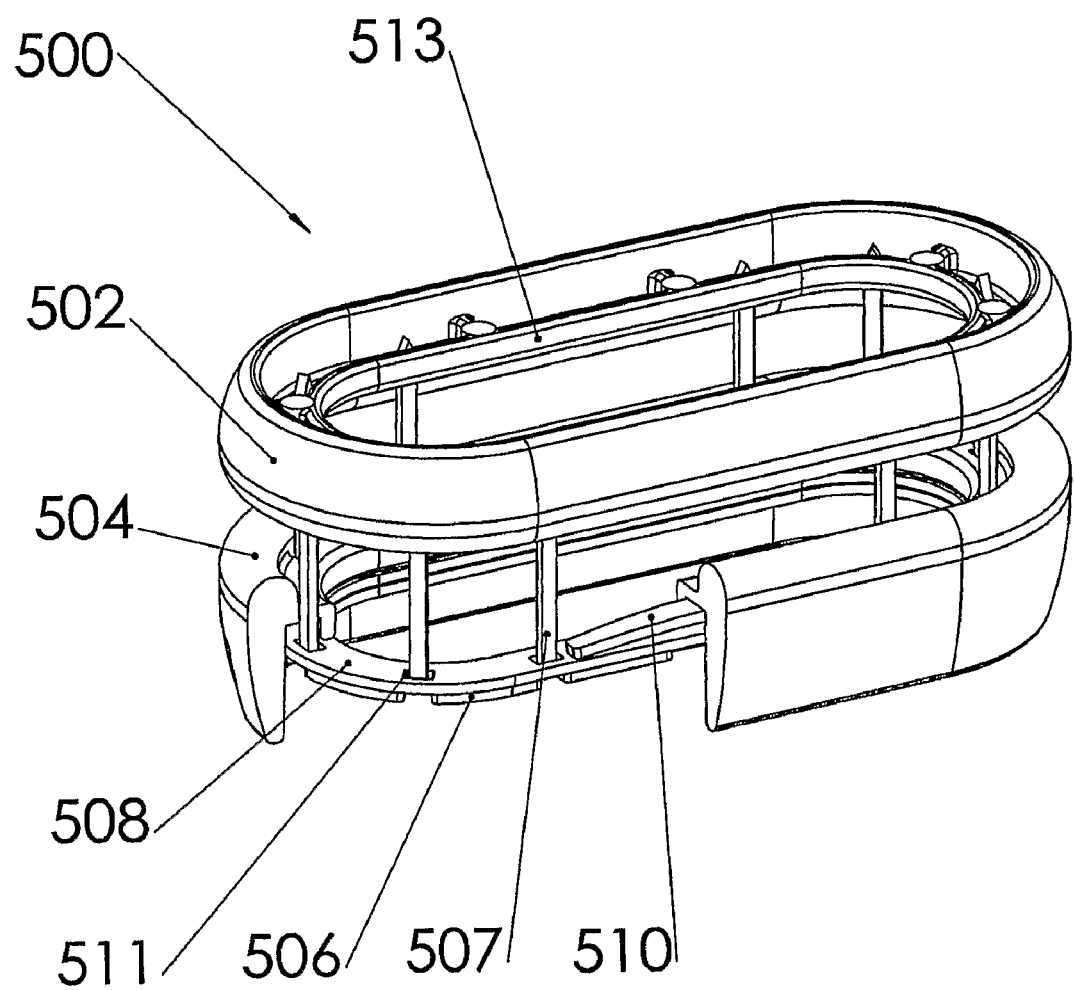
Figure 25D:
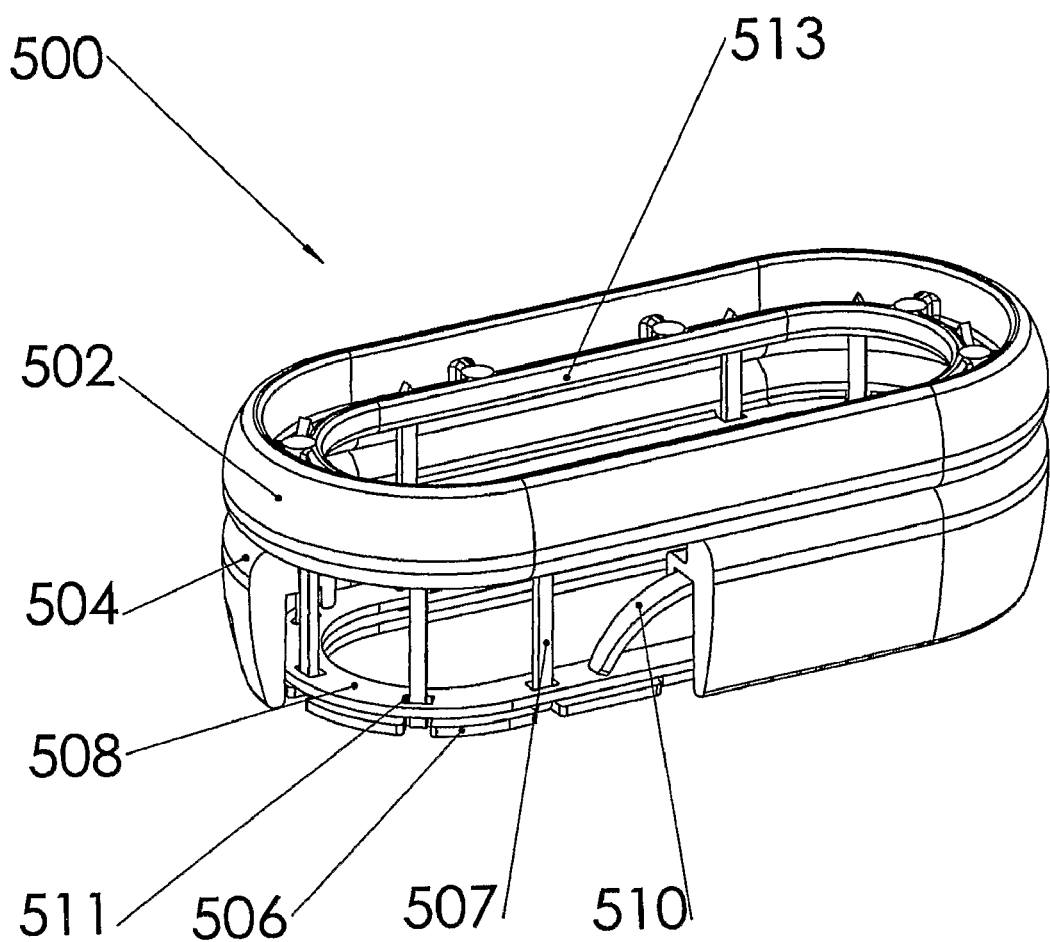

As noted previously, the present invention contemplates compression assemblies that may be constructed in many different shapes, including an elliptical shape. Reference is now made to FIGS. 25A-25D where various views, including an exploded view (FIG. 25A) and a partially cut-away view (FIG. 25B) of a compression assembly having an elliptical shape are shown. FIGS. 25B-25D show assembly 500 during various stages of joining the assembly's first 502 and second 501 portions. The tissue being compressed is not shown. The elements of this assembly are similar to those shown in the circular compression elements best seen in FIGS. 6 and 7. The operation and construction of the elliptical assembly 500 are identical to that of assembly 100 (FIGS. 6-13B). Elements that are essentially identical in both assemblies have been given the same identifying numerals with the replacement of the first digit "1" in assembly 100 by a first digit "5" in assembly 500.

Reference is now made to FIGS. 25A-25D where an exploded view and several partial cut-away isometric views of elliptical compression assembly 500 are shown.

Elliptical compression assembly 500 is comprised of a second portion 501 and a first portion 502. First portion 502 acts as a first compression element and, at times, will be denoted as such in the discussion below.

Second portion 501 is comprised of a second compression element 504, a needle bearing support 506 on which a plurality of several needle-like structures 507 are supported, a flange 508 and at least one spring element 510.

Second compression element 504 may, but do not necessarily have to, contain a plurality of apertures 515 that allow the plurality of needle-like structures 507 to easily pass through second compression element 504 on their way to pierce the tissue to be compressed and then pierce first portion 502. These apertures can best be seen in FIGS. 25A and 25B.

First portion 502 may be formed of any of a large number of rigid plastics known to those skilled in the art while bottom compression element 504 may be formed from any of a large number of plastics or metals known to those skilled in the art. First portion 502 is constructed with a body intended to function as a first compression element. It is also constructed with a skirt 513 intended to be pierced by needles 507 discussed below. Piercing of skirt 513 by needles 507 is best seen in FIGS. 25C and 25D. The skirt may be integrally formed with the body of first portion 502; alternatively, it may be joined to the body by any one of the many methods of joining plastic such as hot welding or solution welding known to those skilled in the art. Skirt 513 may include holes into which the ends of needles 507, to be discussed below, may enter. Alternatively, no such holes need be included in the plastic skirt and needles 507 themselves pierce and enter the skirt 513 when a closure force of sufficient magnitude is exerted on them.

As seen in the partially cut-away views of FIGS. 25B-25D, second compression element 504 girdles needle bearing support 506, flange 508 and one or more spring elements 510. Needle bearing support 506 includes a plurality of barbed needles 507. The spacing between needles may be as shown in FIGS. 25A-25D, but this is only a typical configuration. It is not intended to limit other possible spacings of needles 507.

Needles 507 may be formed integrally with needle bearing support 506. Alternatively, they may be joined to needle bearing support 506 by any of several methods known to those skilled in the art, such as welding, gluing, and pressure fitting. These methods are exemplary only and are not intended to be limiting. The shape of the barbs on the heads of needles 507 as shown in FIGS. 25A-25D is exemplary only. Any generally penetrating shape may be used as the head of needles 507, even sharp heads without barbs.

Flange 508 is typically, but without intending to be limiting, formed from any of a large number of metals or plastics known to those skilled in the art. Needle bearing support 506 and the plurality of barbed needles 507 are typically, but without intending to be limiting, formed from any of a large number of metals or plastics known to those skilled in the art.

The one or more spring elements 510 are made from a shape-memory alloy, typically, but again without intending to be limiting, nitinol. Also typically, but without intending to be limiting, spring elements 510, when in their unloaded austenite state, are arch-shaped. The spring elements are positioned to lie on flange 508 between flange 508 and second compression element 504. The top of the arch contacts the underside, that is the closest side, of second compression element 504. When the shape-memory alloy from which spring elements 510 are formed is in its loaded stress-induced martensite state (or stress-retained martensite state), spring elements 510 lie substantially flat along flange 508 below second compression element 504. Spring elements 510 are positioned on flange 508 so that their ends can move when going from the spring elements' uncompressed arched shape to the spring elements' flat compressed shape and vice versa.

Needle bearing support 506 is positioned below flange 508. Flange 508 has holes 511 along its inner generally elliptical circumference through which barbed needles 507 extend from needle bearing support 506 past flange 508.

Spring elements 510 have been described herein as having an arched uncompressed configuration when not compressed and a flat configuration when compressed; these are essentially leaf springs. The present invention also contemplates other possible spring forms and configurations, including conventional coiled configurations.

In what has been described herein throughout, elliptical compression assembly 500 has been described as having a separate flange 508 and a needle bearing support 506. In other embodiments, there may be only a single element, essentially the needle ring with needles 507 affixed thereon. The flange may be eliminated. In such an embodiment, spring elements 510 are positioned on the needle bearing support and they contact the bottom of second compression element 504. The spring elements are movable on needle bearing support 506 and they are capable of moving from their compressed to uncompressed configurations/shapes and vice versa. In this latter embodiment, spring elements 510 are typically, but without intending to be limiting, deployed in their non-compressed austenitic state. When a flange 508 is employed the spring elements 510 are typically deployed in their compressed martensitic state.

The discussion above, in conjunction with FIGS. 14A and 14B, relating to the characteristics of spring elements formed of shape memory alloys is valid with respect to the shape memory elements in the elliptical compression assembly 500.

It should also be noted that any use of the term "bottom compression element" as a term for element 504 should not be deemed as denoting anything about the specific spatial and functional relationship between this element and the other elements of the elliptical compression assembly 500. The spatial and functional relationship of element 504 and the other elements of assembly 500 are defined by the description and the drawings.

Reference will now be made to FIGS. 26A through 32B where the various stages of applying compression assembly 500 are effected by applicator 600. Applicator 600 here is to be considered exemplary only and not to be considered as limiting other possible applicator constructions.

Figure 26B:
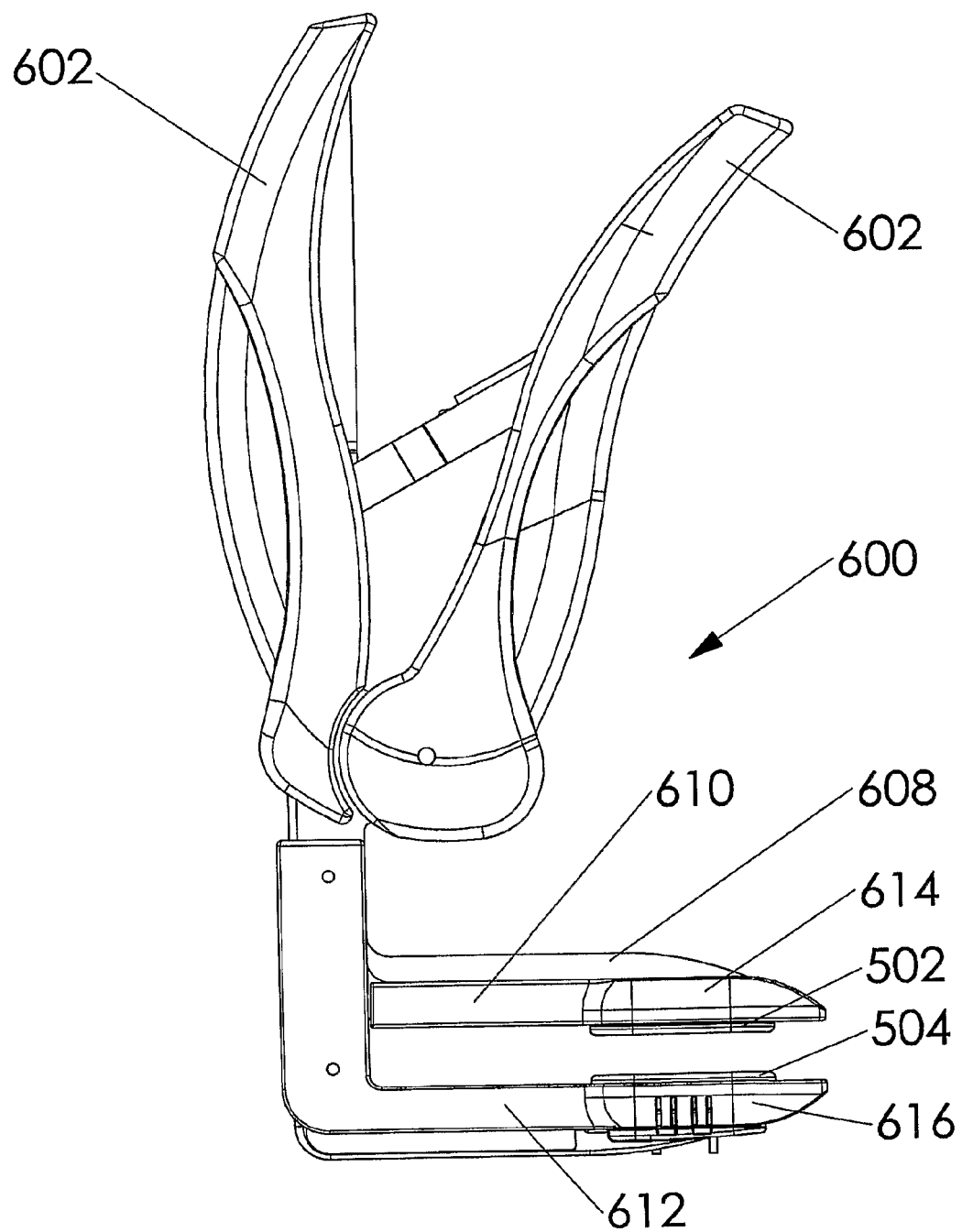
Figure 26C:
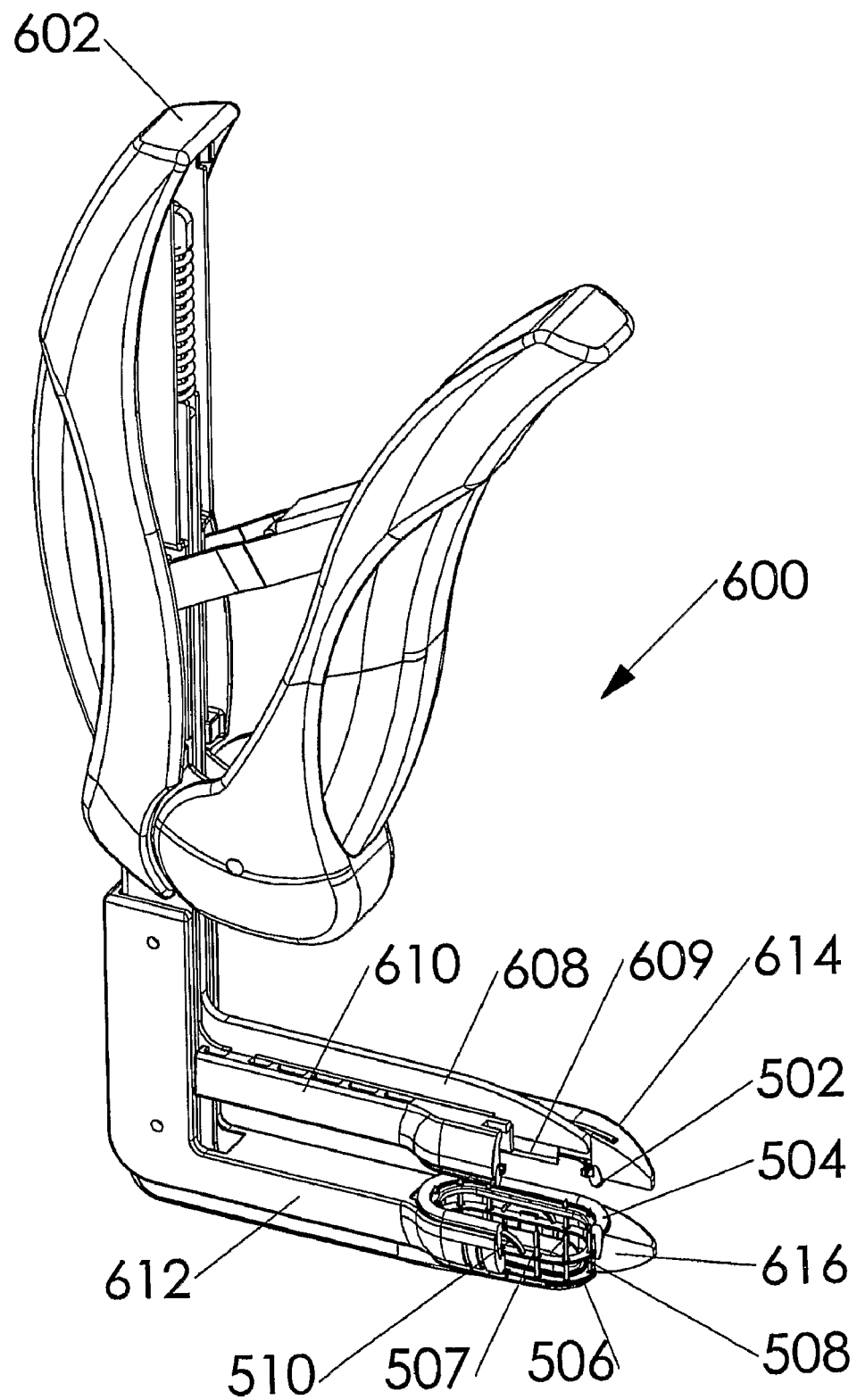

FIGS. 26A-26C show isometric and side views of applicator 600 with attached compression assembly 500 in its open configuration. In its open configuration applicator jaws 610 and 612 are spaced apart. At the end of jaws 610 and 612 distal from applicator handle 602 are receiving depressions 614 and 616, respectively. Receiving depression 614 is sized and configured to receive the first portion 502 of elliptical assembly 500; similarly, receiving depression 616 is sized and configured to receive the second portion 501 of elliptical assembly 500. First portion 502 of assembly 500 is snapped onto and held by connector element 630 (best seen in FIG. 31B), the latter positioned in receiving depression 614. The first 502 and second 501 portions (of which only second compression element 504 is visible) of assembly 500 are spaced apart at this stage. Also present in applicator 600 is blade connector element 608 positioned within jaw 610. Blade connector element 608 connects to blade element 609 discussed below and best seen in FIG. 26C. Element 608 is activated after jaws 610 and 612 are brought proximate to each other by partially squeezing handle 602; a resumption of the squeeze activates blade connector element 608.

FIG. 26C shows a cut-away view of second portion 501 of assembly 500 positioned in receiving depression 616 in jaw 612.

Figure 27:
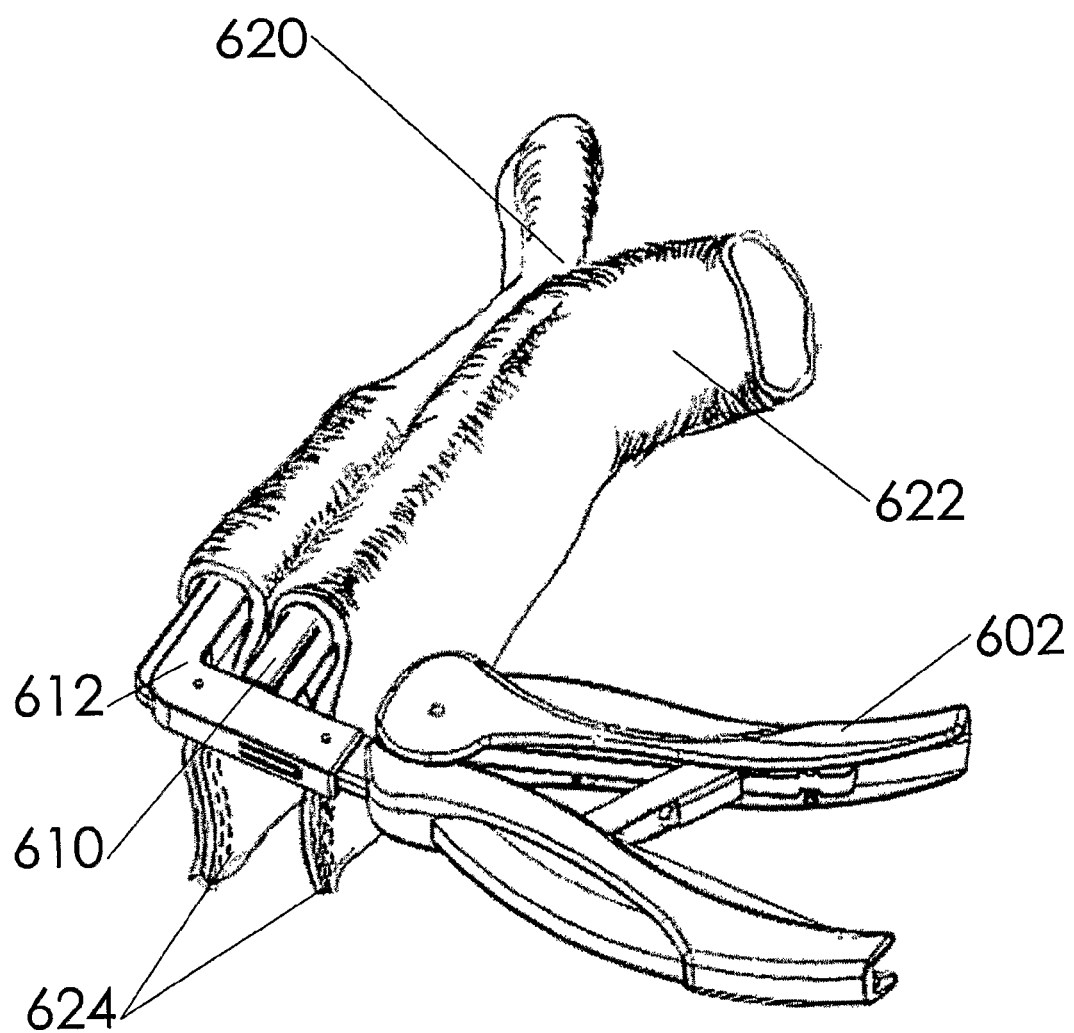
FIG. 27 shows severed tissue positioned over the two jaws of the applicator of FIGS. 26A-26C and the compression assembly positioned therein prior to effecting side-to-side anastomosis.

FIG. 27 shows two halves 620 and 622 of severed tissue, such as the two halves of severed bowel tissue, with one half draped over first jaw 610 and the second half draped over second jaw 612. The tissue portions have been sutured or stapled 624 at their ends. In FIG. 27, the tissue is positioned to allow side-to-side anastomosis. It should be remembered that other surgical joining procedures as well may be effected using elliptical compression assembly 500 shown and described herein. In the remaining FIGS. 28A-32B the tissue is not shown but all of these Figures should be viewed as having tissue positioned between first 502 and second 501 portions of assembly 500, even after ejection of assembly 500 from applicator 600 as in FIGS. 32A-32B.

Figure 28A:
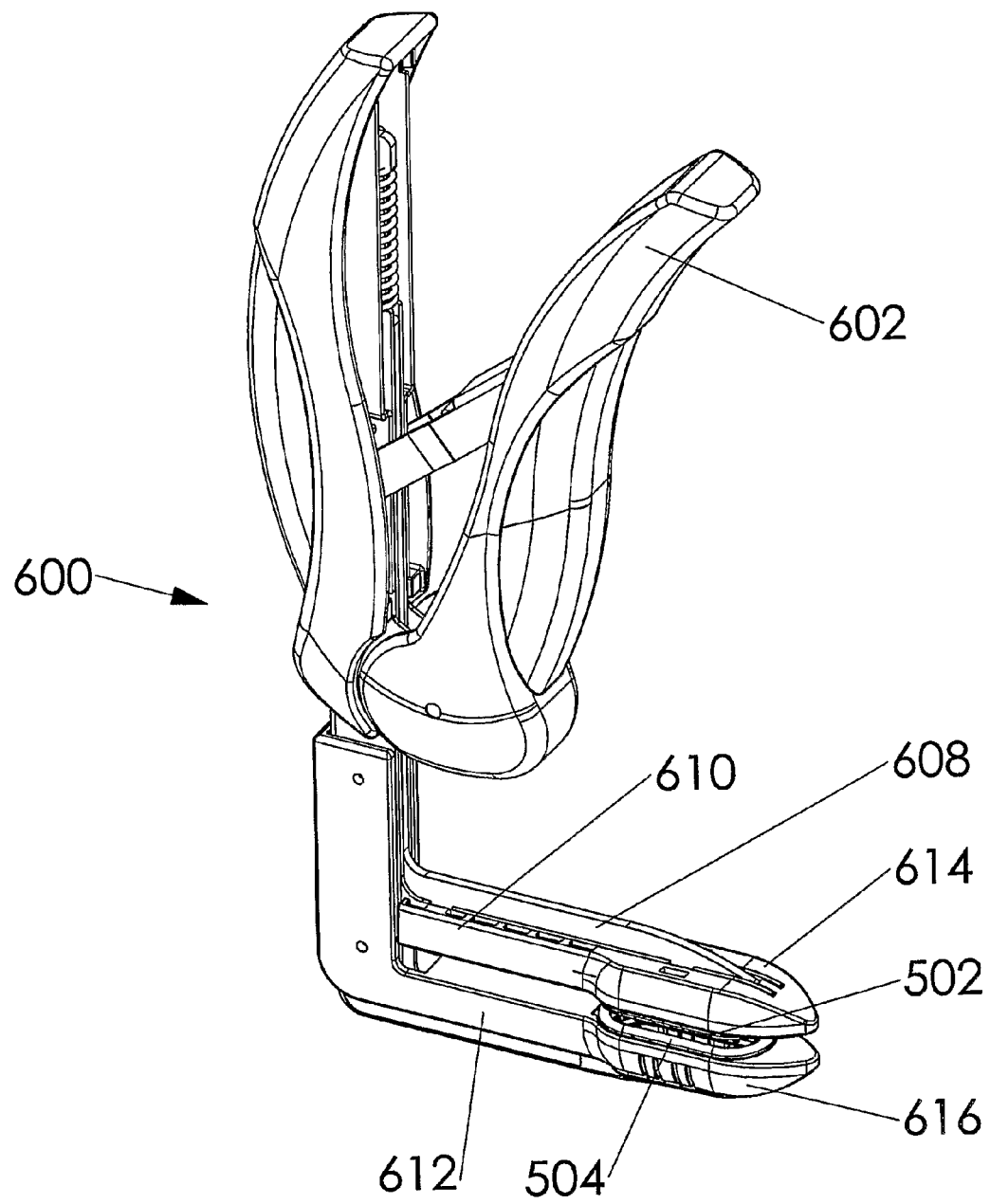
FIGS. 28A and 28B show isometric and side views of the elliptical compression assembly positioned on the applicator shown in FIGS. 26A-26C after proximation of the applicator's jaws.
Figure 28B:
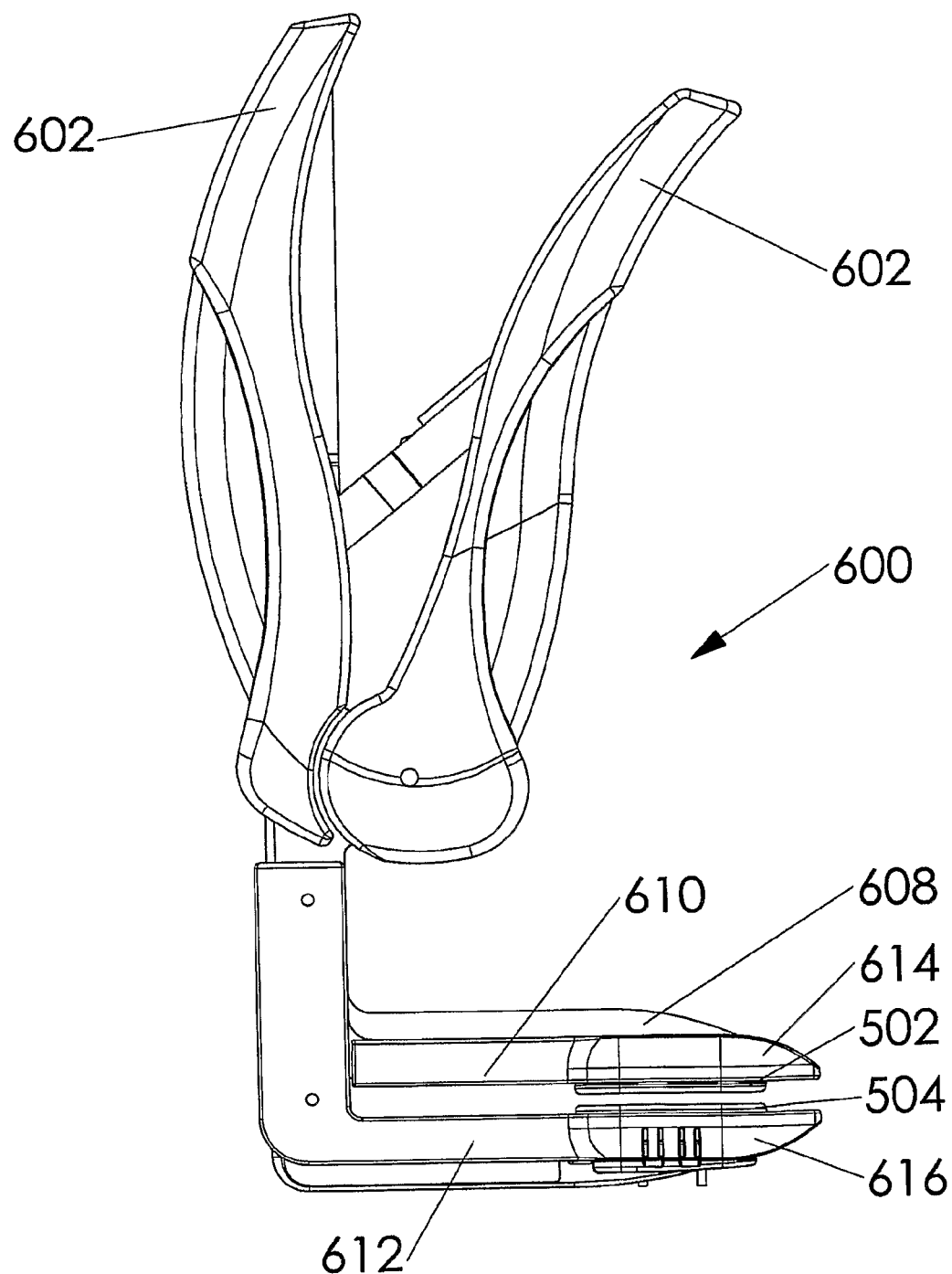

Proximation of the first 502 and second 501 portions (of which only second compression element 504 is visible) of assembly 500 is shown in FIGS. 28A and 28B. Handle 602 is in mechanical communication with jaws 610 and 612. Upon squeezing handle 602 of applicator 600, jaw 610 moves in the direction of jaw 612. Mechanical communication between handle 602 and jaws 610 and 612 may be effected in many different ways as is known to those skilled in the art.

Figure 29A:
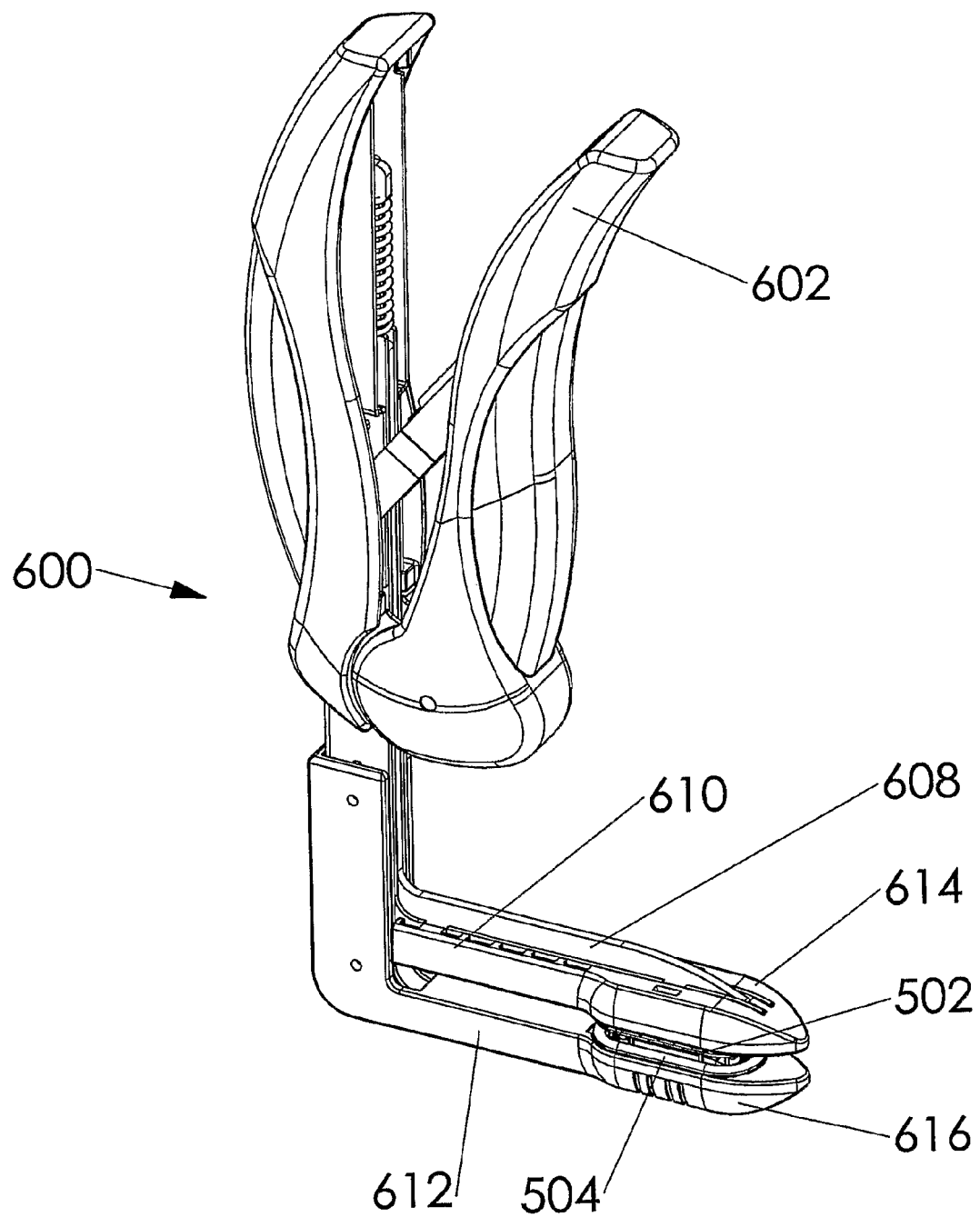
FIGS. 29A and 29B show isometric and side views of the elliptical compression assembly positioned on the applicator shown in FIGS. 26A-26C after the parts of the elliptical compression assemblies are connected via the needle elements.
Figure 29B:
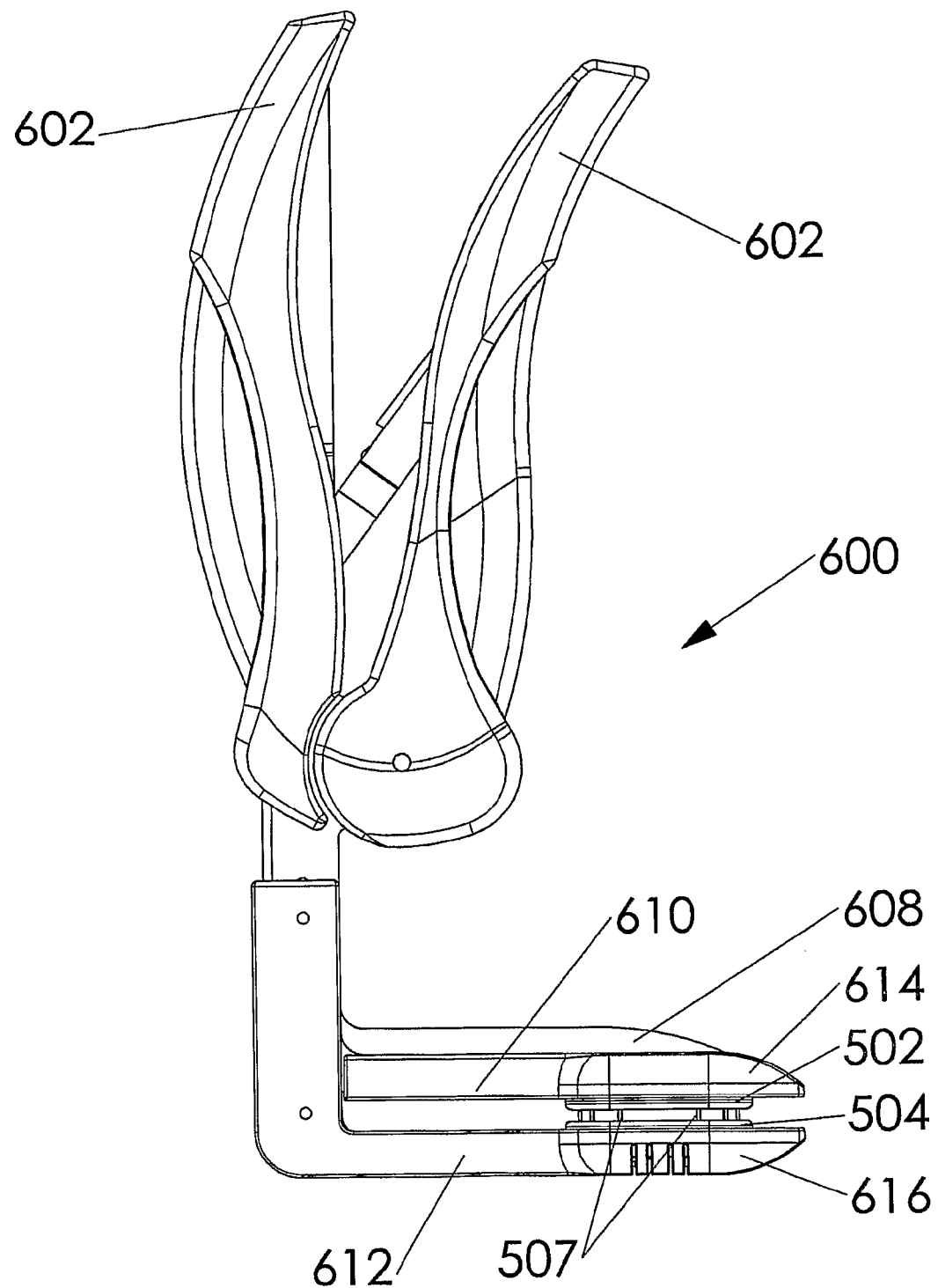

Upon continued pressure when the handle is squeezed, needles 507 of assembly 500 pierce the tissue held between the first 502 and second 501 portions of assembly 500. The tissue, while not shown in FIGS. 28A-32B, is to be viewed as situated on the jaws as shown in FIG. 27. After piercing the tissue, needles 507 then move on to pierce the first portion 502 of assembly 500, thereby bringing into mechanical connection first 502 and second 501 portions of assembly 500 (FIGS. 29A and 29B). Compression of the tissue held between first and second compression elements 502 and 504 then proceeds.

Figure 30A:
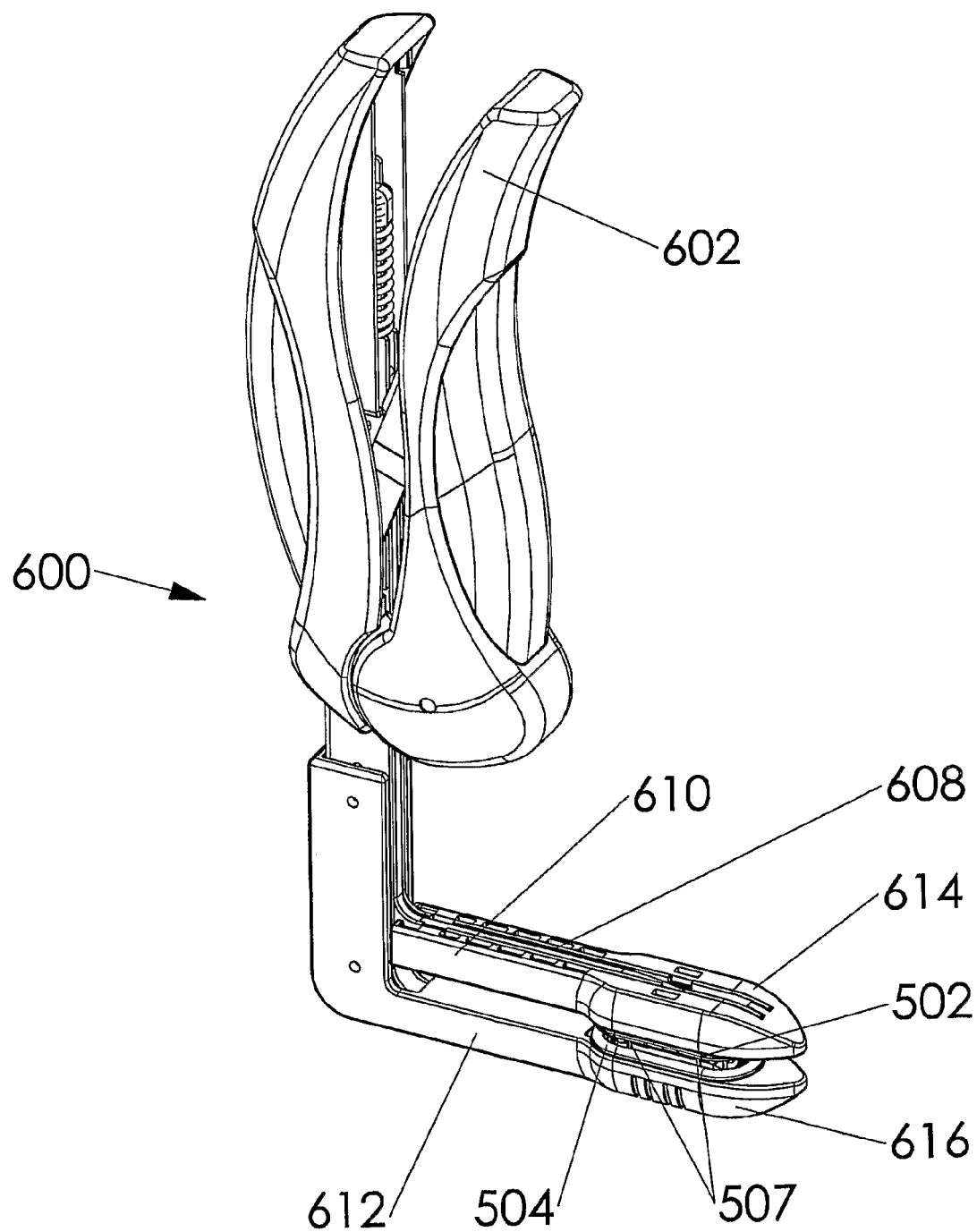
FIGS. 30A, 30B and 30C show isometric, side and partially cut away views, respectively, of the elliptical compression assembly positioned on the applicator shown in FIGS. 26A-26C after the blade element has been activated.
Figure 30B:
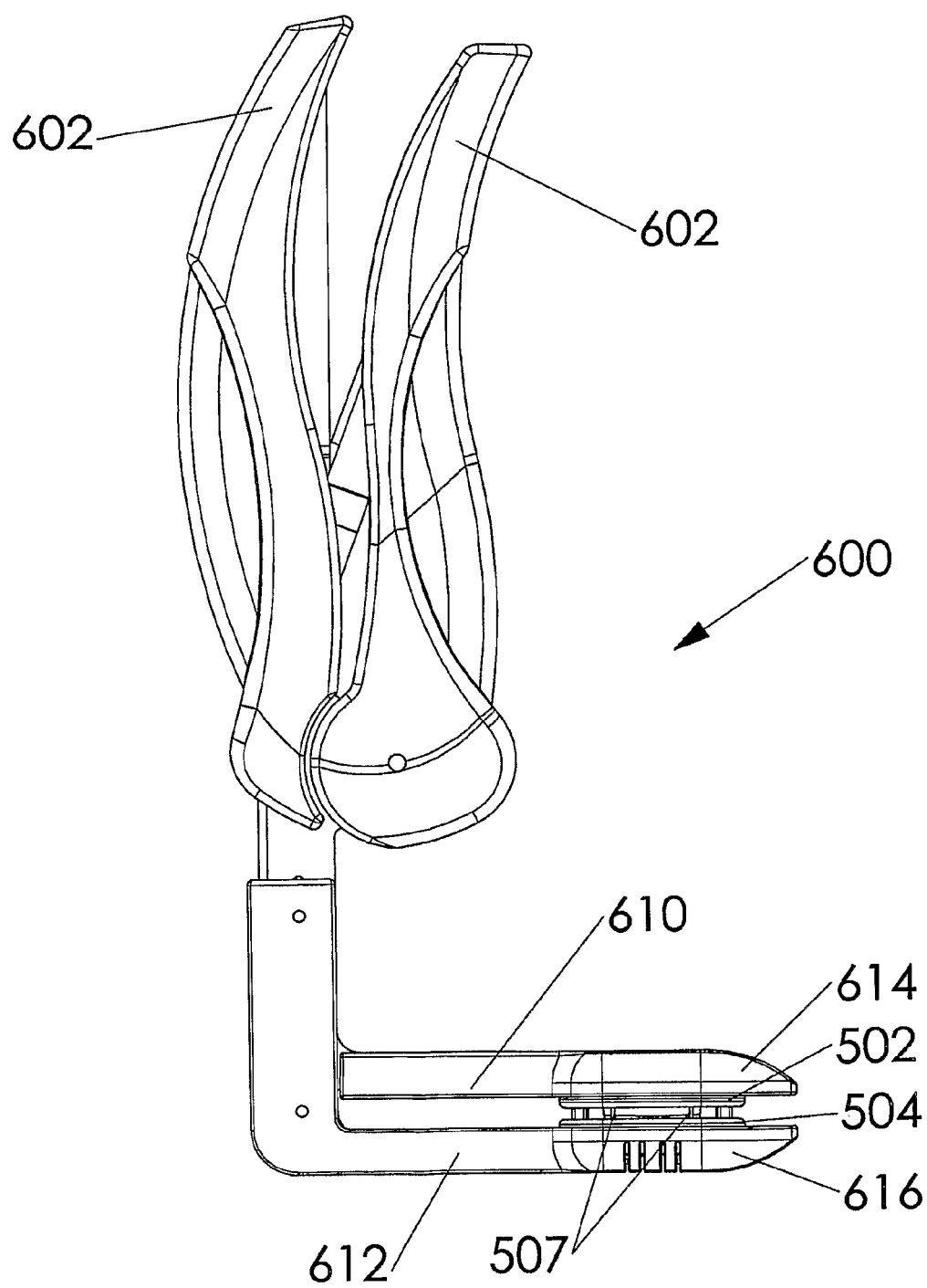
Figure 30C:
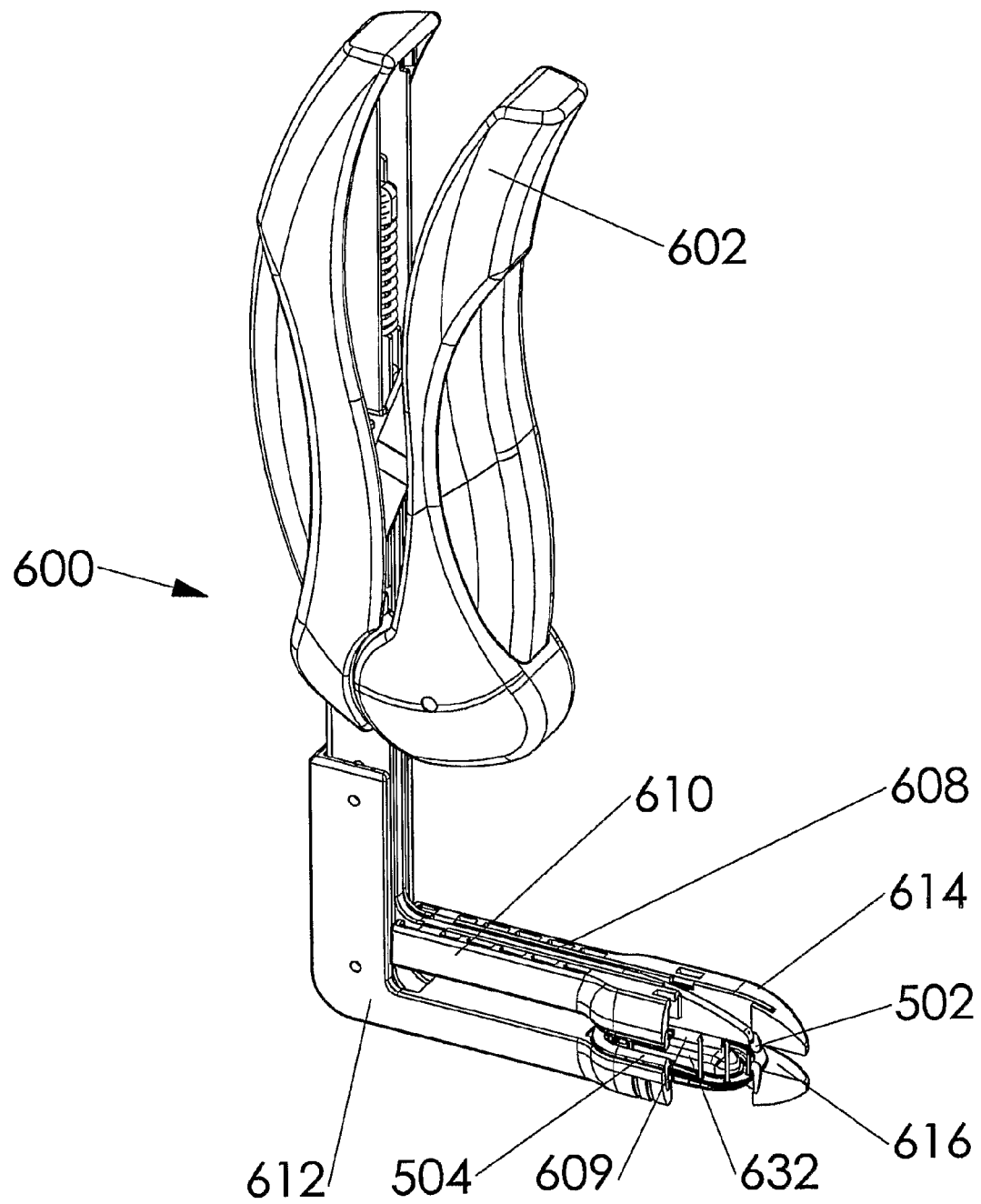

With handle 602 still squeezed, blade connector element 608 moves in the direction of jaw 612 cutting the tissue (not shown) held between the first 502 and second 501 portions of assembly 500 (FIGS. 30A and 30B). The opening in the held and compressed tissue formed by this operation allows for patency and continuity between the two portions of the severed bowel. The blade element 609 (FIG. 30C) is stopped by an anvil 632 best seen in FIG. 32A and FIG. 30C.

Figure 31B:
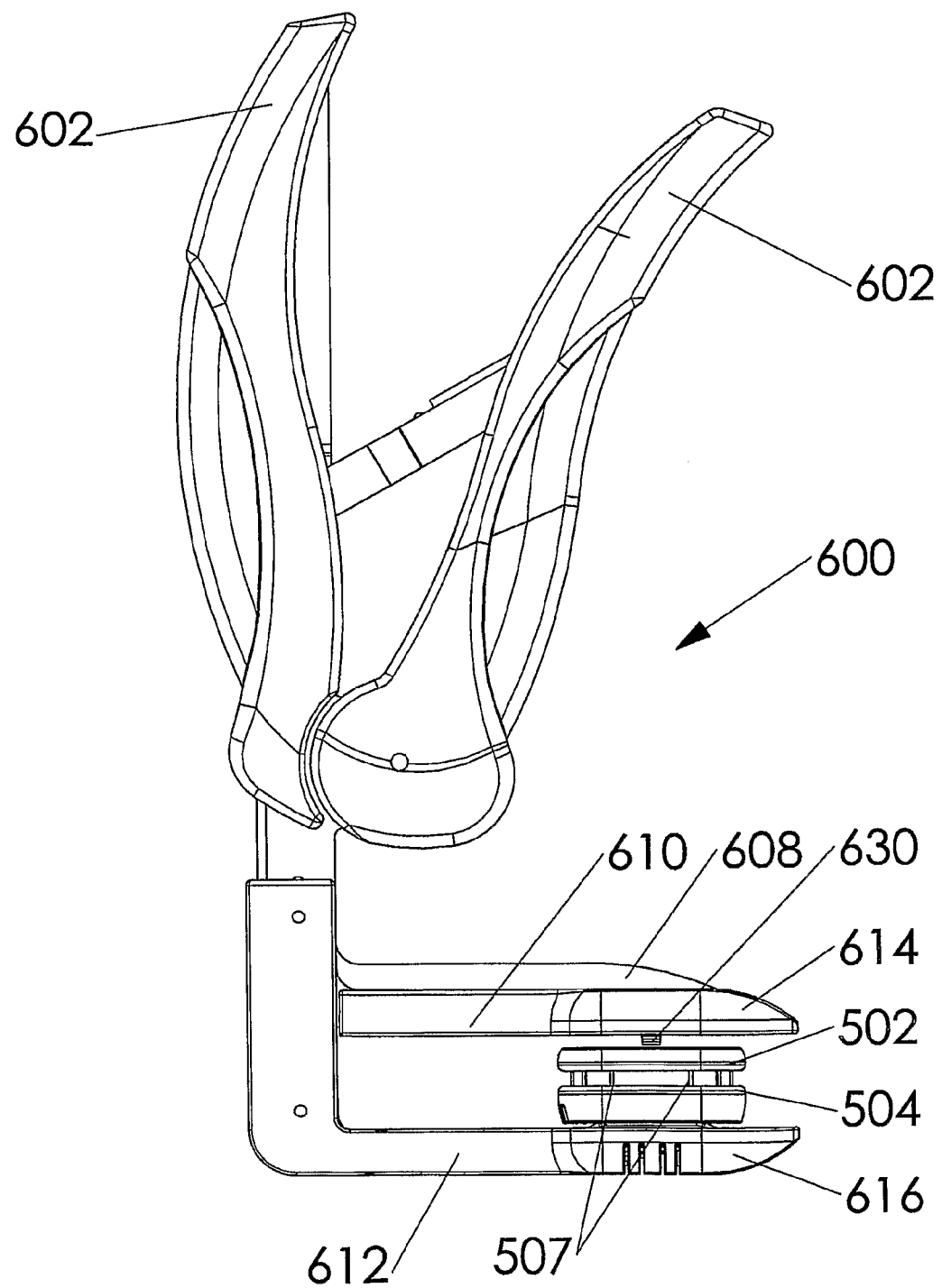

In FIGS. 31A and 31B to which reference is now made, mechanically connected first 502 and second 501 portions of elliptical compression assembly 500 joined together by needles 507 which have penetrated first compression element 502 and with tissue (not shown) held therebetween are released from receiving depressions 614 and 616, respectively. Blade connector element 608 is in contact with first portion 502 pushing it away and releasing it from connector element 630 during the cutting step and the second portion that is held in place by needle bearing support 506 is released from receiving depression 616. In FIG. 31B, the release of first portion 502 of assembly 500 from connector element 630 positioned in receiving depression 614 is recognizable. Connector element 630 holds first portion 502 of assembly 500 in receiving depression 614.

Figure 32B:
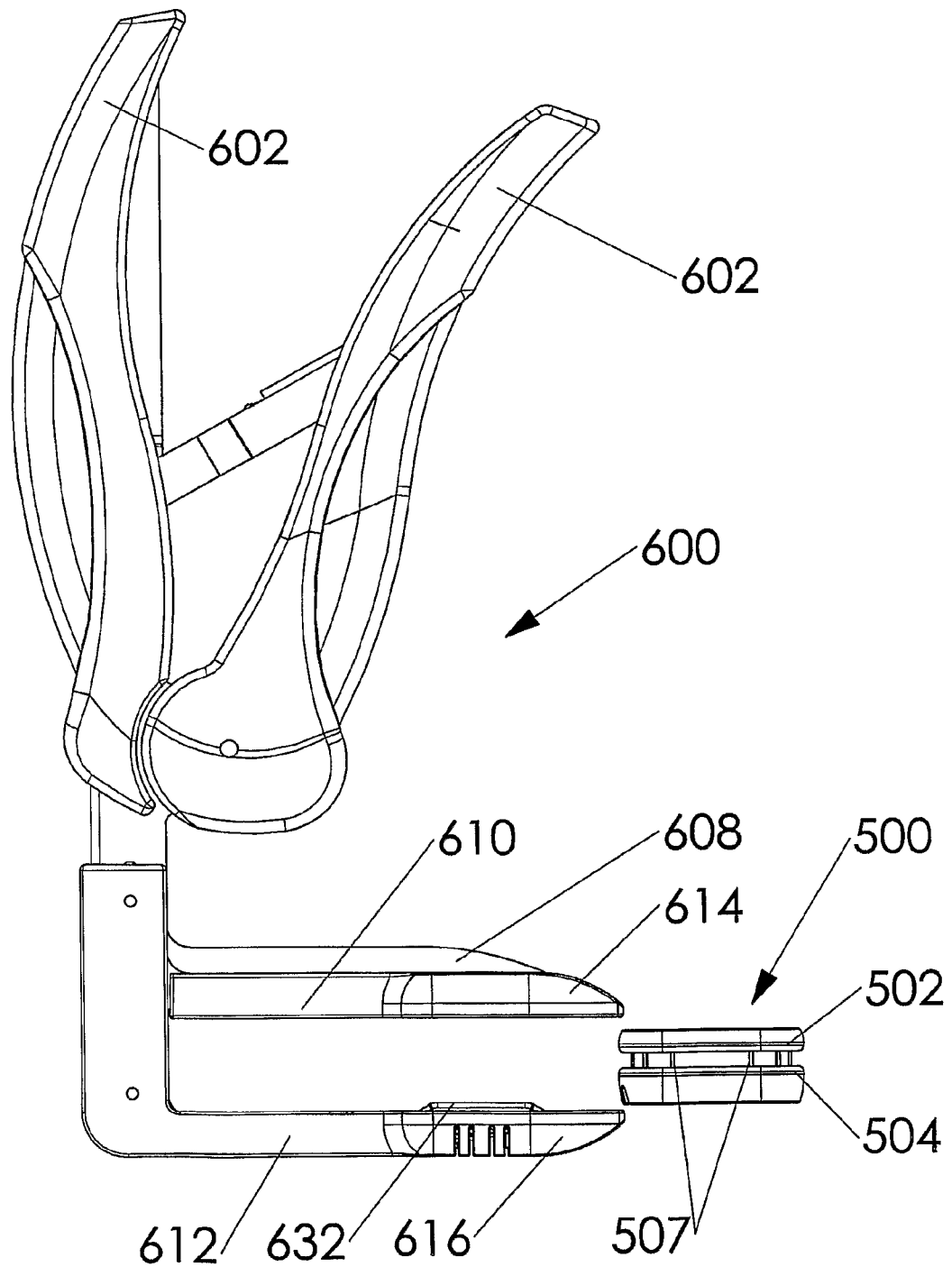

Finally, in FIGS. 32A and 32B, the complete elliptical compression assembly 500 with tissue (not shown) held therebetween is ejected from between jaws 610 and 612 of applicator 600. Elliptical compression assembly 500 remains attached to the tissue (not shown) being compressed until necrosis and healing are complete whereupon assembly 500 detaches from the newly joined tissue and is evacuated through the anus.

It should be borne in mind that applicator 600 discussed herein with elliptical compression assembly 500 is only exemplary and not intended to be limiting. Other applicators may also be designed by persons skilled in the art that may be used with elliptical compression assembly 500.

It will be appreciated by persons skilled in the art that the present invention is not limited by the drawings and description hereinabove presented. Rather, the invention is defined solely by the claims that follow.

The invention claimed is:

1. A compression assembly which comprises:
 a first portion which comprises:
  a first compression element; and
 a second portion which comprises:
  a second compression element positioned substantially parallel to and spaced apart from said first compression element, said first and second compression elements being adapted to be brought together in the presence of a closure force applied thereacross;
 at least one support element, where one of said at least one support elements is a needle bearing support element, said needle bearing support element having a plurality of needles extending generally transversely therefrom toward said first compression element; and at least one spring element positioned on one of said at least one support elements and being in compressive force transmissive contact with said second compression element, said spring element providing a non-Hooke's Law restorative force to said second compression element, wherein when said compression assembly is positioned so as to hold between said first and second compression elements tissue portions to be compressed therebetween, said needle bearing support is operative in response to the closure force to drive said plurality of needles through the tissue portions to be compressed and to anchor said plurality of needles in said first portion, and wherein when said first and second compression elements are brought together in the presence of the closure force holding the tissue portions therebetween, the restorative force provided by said at least one spring element is operative on said second compression element to compress the tissue portions.

2. A compression assembly as in claim 1 wherein said at least one spring element has a force-extension graph composed of a first region, a second region and an intermediate region lying between said first and second regions, and where in said intermediate region, the force-extension slope is substantially less than the force-extension slope of at least one of the two adjacent regions.

3. A compression assembly as in claim 1 wherein said at least one spring element is at least partially formed from a material which has a recoverable strain of at least about 4%.

4. A compression assembly as in claim 1 wherein said at least one spring element is at least partially formed from a shape memory material.

5. A compression assembly according to claim 1 wherein said first and second compression elements and said at least one support element are formed having the same shape, the shape selected from the group consisting of circular, elliptical, oval and linear shapes.

6. An assembly according to claim 1 wherein said first portion further comprises an upper element support made from a rigid polymeric material with said first compression element affixed to said upper element support.

7. An assembly according to claim 6 wherein said plurality of needles is operable to penetrate and pass through the tissue and said upper element support in response to a predetermined force applied to the needle bearing support element.

8. An assembly as in claim 1, wherein said at least one spring element is brought to its compressed configuration, and the material from which it is formed to its martensitic state, by applying thereto a compressive stress.

9. An assembly as in claim 1, wherein said at least one spring element is brought to its compressed configuration, and the material from which it is formed to its martensitic state, by cooling and then applying thereto a compressive stress.

10. A compression assembly according to claim 1 wherein said at least one support element is at least two support elements, where one of said at least two support elements is said needle bearing support element and another of said at least two support elements is a compression flange positioned inside said second compression element.

11. A compression assembly according to claim 10 wherein said compression flange is positioned between said needle bearing support element and said second compression element, and said at least one spring element is positioned on said compression flange so as to be in compressive force transmissive contact with said second compression element.

12. A compression assembly which comprises:
a first portion which comprises:
a first compression element; and
a second portion which comprises:
a second compression element positioned substantially parallel to and spaced apart from said first compression element, said first and second compression elements being adapted to be brought together in the presence of a closure force applied thereacross;
at least one support element, where one of said at least one support elements is a needle bearing support element, said needle bearing support element having a plurality of needles extending generally transversely therefrom toward said first compression element; and
at least one spring element positioned on one of said at least one support elements and being in compressive force transmissive contact with said second compression element, said spring element providing a non-Hooke's Law restorative force to said second compression element, and said at least one spring element exhibiting a force-extension graph composed of a first region, a second region and an intermediate region lying between said first and second regions, and wherein said intermediate region the force-extension slope is substantially less than the force-extension slope of at least one of the two adjacent regions, wherein when said compression assembly is positioned so as to hold between said first and second compression elements tissue portions to be compressed therebetween, said needle bearing support is operative in response to the closure force to drive said plurality of needles through the tissue portions to be compressed and to anchor said plurality of needles in said first portion, and wherein when said first and second compression elements are brought together in the presence of the closure force holding the tissue portions therebetween, the restorative force provided by said at least one spring element is operative on said second compression element to compress the tissue portions.

13. A compression assembly according to claim 12, wherein said at least one support element is at least two support elements, where one of said at least two support elements is said needle bearing support element and another of said at least two support elements is a compression flange positioned inside said second compression element.

14. A compression assembly according to claim 13 wherein said compression flange is positioned between said needle bearing support element and said second compression element, and said at least one spring element is positioned on said compression flange so as to be in compressive force transmissive contact with said second compression element.

15. A method for compressing tissue, said method comprising the steps of:
positioning the tissue to be compressed between first and second portions of a compression assembly operable for compressing tissue;
moving the first portion of the assembly into close proximity to the second portion so as to hold the tissue therebetween; and
compressing the tissue held between the first and second portions of the compression assembly with a force produced by at least one spring element which provides a non-Hooke's Law restorative force; and wherein the at least one spring element exhibits a force-extension graph composed of a first region, a second region and an intermediate region lying between the first and second regions, and wherein the intermediate region the force-extension slope is substantially less than the force-extension slope of at least one of the two adjacent regions.

16. A method according to claim 15 wherein the at least one spring element is at least partially formed from a material that is a shape memory material.

17. A method according to claim 16 further including the step of cooling the at least one spring element so that the shape memory material is brought to its martensitic state.

18. A method according to claim 17, further including the step of deploying the at least one spring element when in its compressed configuration, the material from which it is formed being in its martensitic state.

19. A method according to claim 17 further including the step of deploying the at least one spring element in its non-compressed configuration, the material from which the at least one spring element is at least partly formed being in its austenite state.

20. A compression system for compressing tissue, said system including:
   a) a compression assembly which comprises:
   a first portion which comprises:
      a first compression element; and
   a second portion which comprises:
      a second compression element positioned substantially parallel to and spaced apart from said first compression element, said first and second compression elements being adapted to be brought together in the presence of a closure force applied thereacross;
      at least one support element, where one of said at least one support elements is a needle bearing support element, said needle bearing support element having a plurality of needles extending generally transversely therefrom toward said first compression element; and
      at least one spring element positioned on one of said at least one support elements and being in compressive force transmissive contact with said second compression element, said spring element providing a non-Hooke's Law restorative force to said second compression element,
   wherein when said compression assembly is positioned so as to hold between said first and second compression elements tissue portions to be compressed therebetween, said needle bearing support is operative in response to the closure force to drive said plurality of needles through the tissue portions to be compressed and to anchor said plurality of needles in said first portion, and
   wherein when said first and second compression elements are brought together in the presence of the closure force holding the tissue portions therebetween, the restorative force provided by said at least one spring element is operative on said second compression element to compress the tissue portions; and b) an applicator for applying said compression assembly, said applicator having a proximal end and a distal end, said applicator comprising:
      i) attachment means including a first connecting member for attachment to said first portion of said compression assembly and a second connecting member for attachment to said second portion of said compression assembly, said connecting members operable to move said attached first portion toward said second portion of said assembly or vice versa until a predetermined distance is reached;
      ii) at least one deployment means positioned on said distal end of said applicator and operable to deploy said second portion of said compression assembly positioned thereon so that said plurality of needles may be brought to a position where they pierce said first portion and the tissue portions to be compressed, mechanically connecting said first and second portions of said assembly maintaining the predetermined distance therebetween; and
      iii) at least one activator operationally connected to said at least one deployment means and said attachment means for activating said attachment means and said deployment means.

21. A compression system according to claim 20 wherein said deployment means further comprises a load means so that when said at least one spring element is deployed, said load means exerts a load on said at least one spring element thereby bringing it to its compressed configuration and the alloy from which it is formed to its martensitic state.

22. A compression system according to claim 20, wherein said applicator further comprises a blade element positioned in spaced relationship to said deployment means, said blade element operable to cut through said first portion of said compression assembly.

23. A compression system according to claim 22, wherein said blade element is further operable to cut through the tissue portions held between said first and said second portions of said compression assembly.

24. A compression system as in claim 22, wherein when said blade element cuts through said first portion of said compression assembly, said first portion's outer part is severed from said inner core and detached from said attachment means, said outer part being mechanically connected to said second portion by said plurality of needles so that said outer part is in registration with, and serves as an anvil for, said second compression element when said at least one spring element presses on said second compression element compressing the tissue held therebetween.

25. A compression system according to claim 22 wherein said deployment means further comprises a load means so that when said at least one spring element is deployed, said load means exerts a load on said at least one spring element thereby bringing it to its compressed configuration and the alloy from which it is formed to its martensitic state.

26. A compression system according to claim 25, wherein said at least one spring element is cooled before said load means exerts a load on, and compresses, said at least one spring element.

* * * * *